United States Patent
Crawford et al.

(10) Patent No.: US 11,992,497 B2
(45) Date of Patent: May 28, 2024

(54) CANNABINOID DERIVATIVES AND THEIR USE

(71) Applicant: Demeetra AgBio, Inc., Lexington, KY (US)

(72) Inventors: John Crawford, Lexington, KY (US); Christopher Chengelis, Lexington, KY (US)

(73) Assignee: DEMEETRA AGBIO, INC., Lexington, KY (US)

( * ) Notice: Subject to any disclaimer, the term of this patent is extended or adjusted under 35 U.S.C. 154(b) by 0 days.

(21) Appl. No.: 18/299,511

(22) Filed: Apr. 12, 2023

(65) Prior Publication Data

US 2023/0322654 A1 Oct. 12, 2023

Related U.S. Application Data

(63) Continuation of application No. PCT/US2022/074534, filed on Aug. 4, 2022.

(60) Provisional application No. 63/229,442, filed on Aug. 4, 2021.

(51) Int. Cl.
| | |
|---|---|
| *C07C 39/19* | (2006.01) |
| *A61K 9/00* | (2006.01) |
| *A61K 31/00* | (2006.01) |
| *A61P 1/00* | (2006.01) |
| *A61P 1/04* | (2006.01) |
| *A61P 25/08* | (2006.01) |
| *A61P 29/00* | (2006.01) |
| *C07C 43/215* | (2006.01) |
| *C07C 43/23* | (2006.01) |

(52) U.S. Cl.
CPC .......... *A61K 31/658* (2023.05); *A61K 9/0053* (2013.01); *A61P 1/00* (2018.01); *A61P 1/04* (2018.01); *A61P 29/00* (2018.01); *C07C 39/19* (2013.01); *C07C 43/215* (2013.01); *C07C 43/23* (2013.01)

(58) Field of Classification Search
CPC ....... C07C 43/23; C07C 39/19; C07C 43/215; A61K 31/658; A61K 31/50
See application file for complete search history.

(56) References Cited

U.S. PATENT DOCUMENTS

| | | | |
|---|---|---|---|
| 6,630,507 B1 | 10/2003 | Hampson et al. | |
| 10,384,997 B2 | 8/2019 | Kavarana et al. | |
| 10,555,906 B2 | 2/2020 | Sacks et al. | |
| 10,918,608 B2 | 2/2021 | Guy et al. | |
| 11,040,932 B2 | 6/2021 | Smeltzer et al. | |
| 11,154,502 B2 | 10/2021 | Marangoni | |
| 11,273,122 B2 | 3/2022 | Mainella | |
| 11,298,336 B2 | 4/2022 | Modi | |
| 11,384,040 B2 | 7/2022 | Brumar et al. | |
| 11,446,278 B2 | 9/2022 | Guynn | |
| 2012/0172339 A1 | 7/2012 | Makriyannis et al. | |
| 2014/0271940 A1 | 9/2014 | Wurzer | |
| 2018/0296521 A1 | 10/2018 | Schrader | |
| 2019/0091198 A1 | 3/2019 | Bar-Lev Schleider | |
| 2019/0133966 A1 | 5/2019 | Koren | |
| 2021/0299081 A1 | 9/2021 | Yuan et al. | |
| 2021/0378950 A1 | 12/2021 | Mainella | |
| 2021/0393519 A1 | 12/2021 | Lucas et al. | |
| 2021/0393540 A1 | 12/2021 | Lucas et al. | |
| 2022/0064090 A1 | 3/2022 | Linciano et al. | |
| 2022/0127213 A1 | 4/2022 | Nahtigal | |
| 2022/0153670 A1 | 5/2022 | Gerlach et al. | |
| 2022/0186231 A1 | 6/2022 | Schuetz et al. | |
| 2022/0193003 A1 | 6/2022 | Alugupalli et al. | |
| 2022/0220089 A1 | 7/2022 | Abdur-Rashid et al. | |
| 2022/0235023 A1 | 7/2022 | Adair et al. | |
| 2022/0265601 A1 | 8/2022 | Heldreth, Jr. | |
| 2022/0290200 A1 | 9/2022 | Milne et al. | |
| 2022/0362169 A1 | 11/2022 | Metcalf | |
| 2022/0370402 A1 | 11/2022 | Thomas | |
| 2022/0387376 A1 | 12/2022 | Thomas et al. | |
| 2022/0396540 A1 | 12/2022 | Thomas et al. | |
| 2023/0000936 A1 | 1/2023 | Bryant et al. | |
| 2023/0023342 A1 | 1/2023 | Moustafa | |

(Continued)

FOREIGN PATENT DOCUMENTS

| | | |
|---|---|---|
| CA | 3044735 A1 | 8/2019 |
| WO | WO-2008107879 A1 | 9/2008 |

(Continued)

OTHER PUBLICATIONS

Appendino, et al., "Antibacterial Cannabinoids from Cannabis sativa: A Structure-Activity Study". J. Nat Prod. (Aug. 2008); 71(8): 1427-1430. Epub Aug. 6, 2008.
Blaskovich, Mark A. et all. "The antimicrobial potential of cannabidiol", Communications Biology (2021), 4(1), 18 pages.
Borrelli, et al., "Beneficial effect of the non-psychotropic plant cannabinoid cannabigerol on experimental inflammatory bowel disease". Biochem Pharmacol (May 1, 2013); 85(9): 1306-1316. Epub Feb. 12, 2013.

(Continued)

*Primary Examiner* — Rayna Rodriguez
(74) *Attorney, Agent, or Firm* — COOLEY LLP

(57) ABSTRACT

Provided herein are methods of using a compound of Formula (I) or pharmaceutically acceptable salt thereof, for example, in the treatment of a mental health disorder or chronic inflammatory disease.

(I)

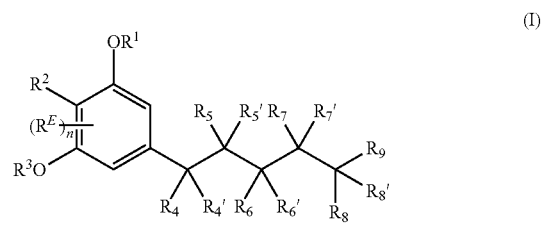

8 Claims, 48 Drawing Sheets

(56) References Cited

U.S. PATENT DOCUMENTS

| | | |
|---|---|---|
| 2023/0032113 A1 | 2/2023 | Noel |
| 2023/0047027 A1 | 2/2023 | Byrant et al. |
| 2023/0059087 A1 | 2/2023 | Zhou et al. |
| 2023/0089351 A1 | 3/2023 | Metcalf |
| 2023/0248748 A1 | 8/2023 | Crawford et al. |

FOREIGN PATENT DOCUMENTS

| | | |
|---|---|---|
| WO | WO 2011/022638 | 2/2011 |
| WO | WO-2013035114 A1 | 3/2013 |
| WO | WO-2014198993 A1 | 12/2014 |
| WO | WO-2016087649 A2 | 6/2016 |
| WO | WO-2018091551 A1 | 5/2018 |
| WO | WO-2019030762 A2 | 2/2019 |
| WO | WO-2019036243 A1 | 2/2019 |
| WO | WO-2019079677 A1 | 4/2019 |
| WO | WO-2020024056 A1 | 2/2020 |
| WO | WO-2020069214 A2 | 4/2020 |
| WO | WO-2020077153 A1 | 4/2020 |
| WO | WO-2020107119 A1 | 6/2020 |
| WO | WO-2021071967 A1 | 4/2021 |
| WO | WO-2021078412 A1 | 4/2021 |
| WO | WO-2021105996 A1 | 6/2021 |
| WO | WO-2021156839 A1 | 8/2021 |
| WO | WO-2021158575 A1 | 8/2021 |
| WO | WO-2021195517 A2 | 9/2021 |
| WO | WO-2021195751 A1 | 10/2021 |
| WO | WO-2021222288 A1 | 11/2021 |
| WO | WO-2021243467 A1 | 12/2021 |
| WO | WO-2021243468 A1 | 12/2021 |
| WO | WO-2021245658 A1 | 12/2021 |
| WO | WO-2022006498 A1 | 1/2022 |
| WO | WO-2022036462 A1 | 2/2022 |
| WO | WO-2022091080 A1 | 5/2022 |
| WO | WO-2022099078 A1 | 5/2022 |
| WO | WO-2022113071 A2 | 6/2022 |
| WO | WO-2022133544 A1 | 6/2022 |
| WO | WO-2022147470 A1 | 7/2022 |
| WO | WO-2022182523 A1 | 9/2022 |
| WO | WO-2022182527 A1 | 9/2022 |
| WO | WO-2022183292 A1 | 9/2022 |
| WO | WO-2022187973 A1 | 9/2022 |
| WO | WO-2022213120 A1 | 10/2022 |
| WO | WO-2022221367 A1 | 10/2022 |
| WO | WO-2022254425 A1 | 12/2022 |
| WO | WO-2022266765 A1 | 12/2022 |
| WO | WO-2022266767 A1 | 12/2022 |
| WO | WO-2023004414 A1 | 1/2023 |
| WO | WO-2023010083 A2 | 2/2023 |
| WO | WO-2023023621 A1 | 2/2023 |

OTHER PUBLICATIONS

Borrelli F et al. Cannabidiol, a safe and non-psychotropic ingredient of marijuana plant Cannabis sativa, is protective in murine model of colitis, J. Mol. Med. 2009:87:1111-1121.

CAPLUS RN 55824-15-2 REGISTRY Entered STN: Nov. 16, 1984, 1 page.

Chianese, Giuseppina et al. "A Nrf-2 Stimulatory Hydroxylated Cannabidiol Derivative from Hemp (Cannabis sativa)", Journal of Natural Products (2022), 85(4), 1089-1097.

Consroe et al. "Antiepileptic Potential of Cannabidiol Analogs", J Clin Pharmacol. 1981; 21 :428S-436S.

Costa et al. "Antiseizure Effects of Fully Characterized Non-Psychoactive Cannabis sativa L. Extracts in the Repeated 6-Hz Corneal Stimulation Test", Pharmaceuticals 2021, 14(12), 1259.

Crombie, Leslie et al. "Cannabinoid bis-homologs: Miniaturized synthesis and GLC study", Phytochemistry (Elsevier) (1975), 14(1), 213-220.

Field "Cannabinoid compounds in South African Cannabis sativa L", Journal of Pharmacy and Pharmacology (1980), 32(1), 21-24.

Golliher, Alexandra E. et al. "Using (+)-carvone to access novel derivatives of (+)-ent-cannabidiol: The first asymmetric syntheses of (+)-ent-CBDP and (+)-ent-CBDV", Tetrahedron Letters (2021), 67, 152891, 4 pages.

Husni A. et al. "Evaluation of phytocannabinoids from high-potency Cannabis sativa using in vitro bioassays to determine structure-activity relationships for cannabinoid receptor 1 and cannabinoid receptor 2", Medicinal Chemistry Research (2014), 23(9), 4295-4300.

International Search Report and Written Opinion for International Application No. PCT/US2022/074534 dated Jan. 11, 2023, 18 pages.

Iseger et al. "A systematic review of the antipsychotic properties of cannabidiol in humans", Schizophrenia Research 162 (2015) 153-161.

Jamontt et al., "The effects of delta 9-tetrahydrocannabinol and cannabidiol alone and in combination on damage, inflammation and invitro motility disturbances in rat colitis," British Journal of Pharmacology, 2010, vol. 160, pp. 712-723.

Jones et al., "Cannabidiol Displays Antiepileptiform and Antiseizure Properties in Vitro and in Vivo," J Pharmacol Exp Ther., 332(2):559-577 (2010).

Kasteel E. et al. "Human variability in isoform-specific UDP-glucuronosyltransferases: markers of acute and chronic exposure, polymorphisms and uncertainty factors", Archives of Toxicology (2020) 94:2637-2661.

Kogan N.M., et al. "Novel CBG Derivatives Can Reduce Inflammation, Pain and Obesity," Molecules, Sep. 15, 2021, vol. 26(18), p. 1-16.

Lahat A et al. "Impact of Cannabis Treatment on the Quality of Life, Weight and Clinical Disease Activity in Inflammatory Bowel Disease Patients: A Pilot Prospective Study", Digestion 2012; 85:1-8.

Lal S. et al. "Cannabis use amongst patients with inflammatory bowel disease", Eur. J. Gastroenterol. Hepatol. 2011, 23(10):891-896.

Linciano, Pasquale et al. "Identification of a new cannabidiol n-hexyl homolog in a medicinal cannabis variety with an antinociceptive activity in mice: cannabidihexol", Scientific Reports (2020), 10(1), 22019, 11 pages.

Linciano, Pasquale et al. "The novel heptyl phorolic acid cannabinoids content in different Cannabis sativa L. accessions", Talanta (2021), 235, 122704, 8 pages.

Liu, Chang et al. "Identification of SARS-CoV-2 Main Protease Inhibitors from a Library of Minor Cannabinoids by Biochemical Inhibition Assay and Surface Plasmon Resonance Characterized Binding Affinity", Molecules (2022), 27(18), 6127, 16 pages.

Loscher et al., "The role of technical, biological and pharmacological factors in the laboratory evaluation of anticonvulsant drugs. III. Pentylenetetrazole seizure models", 1991 Epilepsy Res 8:171-189.

Marihuana '84 [Eighty-Four], Proc. Oxford Symp. Cannabis (1985), Meeting Date 1984, 713-719. Editor(s): Harvey, D. J. Publisher: IRL, Oxford, UK, Dep. Psychol., Univ. Vermont, Burlington, VT, 05405, USA.

Martin et al., "Structure-Anticonvulsant Activity Relationships of Cannabidiol Analogs," National Institute on Drug Abuse, Research Monograph Series, 1987, 79:48-58.

McGuire, P. et al., "Cannabidiol (CBD) as an Adjunctive Therapy in Schizophrenia: A Multicenter Randomized Controlled Trial," Am J Psychiatry (2018), 175:225-231.

Naftali T et al. "Treatment of Crohn's Disease with Cannabis: An Observational Study", Isr. Med. Assoc. J. 2011, 13:455-458.

Papahatjis, Demetris P. et al. "C1'-Cycloalkyl Side Chain Pharmacophore in Tetrahydrocannabinols", Journal of Medicinal Chemistry (2007), 50(17), 4048-4060.

Robson et al. "Cannabinoids and Schizophrenia: Therapeutic Prospects", Current Pharmaceutical Design, 2014; 20(13): 2194-2204.

Salbini, Maria et al. "Oxidative Stress and Multi-Organel Damage Induced by Two Novel Phytocannabinoids, CBDB and CBDP, in Breast Cancer Cells", Molecules (2021), 26(18), 5576, 19 pages.

Sampson, Peter B. "Phytocannabinoid Pharmacology: Medicinal Properties of Cannabis sativa Constituents Aside from the Big Two", Journal of Natural Products (2021), 84(1), 142-160.

Schicho R et al. "Topical and Systemic Cannabidiol Improves Trinitrobenzene Sulfonic Acid Colitis in Mice", Pharmacology 2012;89:149-155.

(56) References Cited

OTHER PUBLICATIONS

Schwarzenberg, Adrian et al. "Characterizing degradation of cannabidiol in e-liquid formulation", Scientific Reports (2022), 12(1), 20058.

U.S. Appl. No. 63/229,442, inventors Crawford; John et al., filed Aug. 4, 2021.

U.S. Appl. No. 63/032,771, filed Jun. 1, 2020.

Behrendt, H.-J. et al., "Characterization of the mouse cold-menthol receptor TRPM8 and vanilloid receptor type-1 VR1 using a fluorometric imaging platereader (FLIPR) assay," British Journal of Pharmacology, 141:737-745 (2004).

CAS Registry Record for 2-(3,7-Dimethylocta-2,6-dien-1-YL)-3-methoxy-5-pentylphenol {CAS#29106-17-0), entered Nov. 16, 1984, 3 pages.

CAS Registry Record for 2-[(2E)-3,7-dimethyl-2,6-octadien-1-yl]-1,3-dimethoxy-5-pentyl-benzene {CAS#29106-16-9), entered Nov. 16, 1984, 3 pages.

CELEBREX® (celecoxib) capsules, for oral use Initial U.S. Approval: 1998; product label; 23 pages.

Kimball et al., "Chemical Protection against Ionizing Radiation I. Sampling Methods for Screening Compounds in Radiation Protection Studies with Mice", Radiation Research Society, 1957, vol. 7, p. 1-12.

Litchfield, J.T. et al. "A Simplified Method of Evaluating Dose-Effect Experiments", J. Pharmacol. Exp. Ther., 1949, vol. 96, p. 99-113.

Löscher et al., "The role of technical, biological and pharmacological factors in the laboratory evaluation of anticonvulsant drugs. II. Maximal electroshock seizure models", Epilepsy Res. 1991, vol. 8, p. 79-94.

Ruhaak, et al., "Evaluation of the cyclooxygenase inhibiting effects of six major cannabinoids isolated from Cannabis sativa". Biol Pharm Bull. (2011); 34(5): 774-778.

Vanachayangkul et al. "Inhibition of Heme Peroxidases byMelamine", Hindawi Publishing Corporation Enzyme Research, vol. 2012, Article ID 416062, Jun. 5, 2012, 7 pages.

FIG. 10

| Sample ID | Time (hrs) | Animal 2001 | Animal 2002 | Animal 2003 | Animal 2004 | Animal 2005 | Animal 2006 | Animal 2007 | Mean Plasma Concentration (ng/ml) |
|---|---|---|---|---|---|---|---|---|---|
| Group 3 Pre-Dose 3001-3007 | 0 | < 0 | < 0 | < 0 | < 0 | < 0 | < 0 | < 0 | BQL |
| Group 3 30min An 3001-3003 | 0.5 | < 0 | < 0 | < 0 | | | | | BQL |
| Group 3 1HR An 3004-3006 | 1 | | | | < 0 | < 0 | < 0 | | BQL |
| Group 3 2HR An 3001-3003 | 2 | < 0 | < 0 | < 0 | | | | | BQL |
| Group 3 4HR An 3004-3006 | 4 | | | | < 0 | < 0 | < 0 | | BQL |
| Group 3 6HR An 3001-3003 | 6 | < 0 | < 0 | < 0 | | | | | BQL |
| Group 3 8HR An 3004-3006 | 8 | | | | < 0 | < 0 | < 0 | | BQL |
| Group 3 12HR An 3001-3003 | 12 | < 0 | < 0 | < 0 | | | | | BQL |
| Group 3 24HR An 3004-3006 | 24 | | | | < 0 | < 0 | < 0 | | BQL |

FIG. 13

| Peak ID | Mass | Formula | Proposed Assignment | | Human | Rat | Dog | Monkey | Minipig |
|---|---|---|---|---|---|---|---|---|---|
| | | | Biotransformation | Structure | | | | | |
| Parent | 316.2402 | C₂₀H₂₈O₂ | Parent | | ✓ | ✓ | ✓ | ✓ | ✓ |
| M1 | 302.2246 | C₁₉H₂₆O₂ | Demethylation | | ✗ | ✓ | ✗ | ✗ | ✗ |
| M2 | 306.1831 | C₁₇H₂₆O₄ | 2x Oxidation − C₃H₄ | | ✓ | ✗ | ✗ | ✗ | ✗ |
| M3 | 413.1872 | C₁₉H₃₁NO₆S | 2x Oxidation − C₃H₄ + Taurine conjugation | | ✗ | ✓ | ✗ | ✗ | ✗ |
| M4 | 482.2152 | C₂₃H₃₄O₁₀ | 2x Oxidation − C₃H₄ + Glucuronidation | | ✓ | ✓ | ✗ | ✗ | ✗ |
| M5 | 492.2723 | C₂₇H₄₀O₈ | Glucuronidation | | ✓ | ✓ | ✓ | ✓ | ✓ |
| M6 | 506.2515 | C₂₇H₃₈O₉ | Oxidation + Desaturation + Glucuronidation | | ✗ | ✗ | ✗ | ✓ | ✗ |

* = Glucuronide conjugations usually occurs on nucleophilic functional groups; these groups have been markushed on the metabolite as proposed sites of conjugation

FIG. 14

| Peak ID | Mass | Formula | Proposed Assignment | | Human | Rat | Dog | Monkey | Minipig |
|---|---|---|---|---|---|---|---|---|---|
| | | | Biotransformation | | | | | | |
| M7 | 508.2672 | C27H40O9 | Oxidation + Glucuronidation | | ✓ | ✓ | × | ✓ | ✓ |
| M8 | 508.2672 | C27H40O9 | Oxidation + Glucuronidation | | ✓ | ✓ | ✓ | ✓ | ✓ |
| M9 | 508.2672 | C27H40O9 | Oxidation + Glucuronidation | | × | ✓ | × | × | × |
| M10 | 522.2465 | C27H38O10 | 2x Oxidation + Desaturation + Glucuronidation | | ✓ | × | × | × | ✓ |
| M11 | 654.3251 | C33H50O13 | Glucuronidation + Glucose Addition | | × | × | ✓ | × | × |
| M12 | 668.3044 | C33H48O14 | 2 x Glucuronidation | | ✓ | ✓ | × | × | × |

* = Glucuronide conjugations usually occur on nucleophilic functional groups; these groups have been markushed on the metabolite as proposed sites of conjugation Latency to Onset of Clonic Seizure FIG. 31
Racine Scales
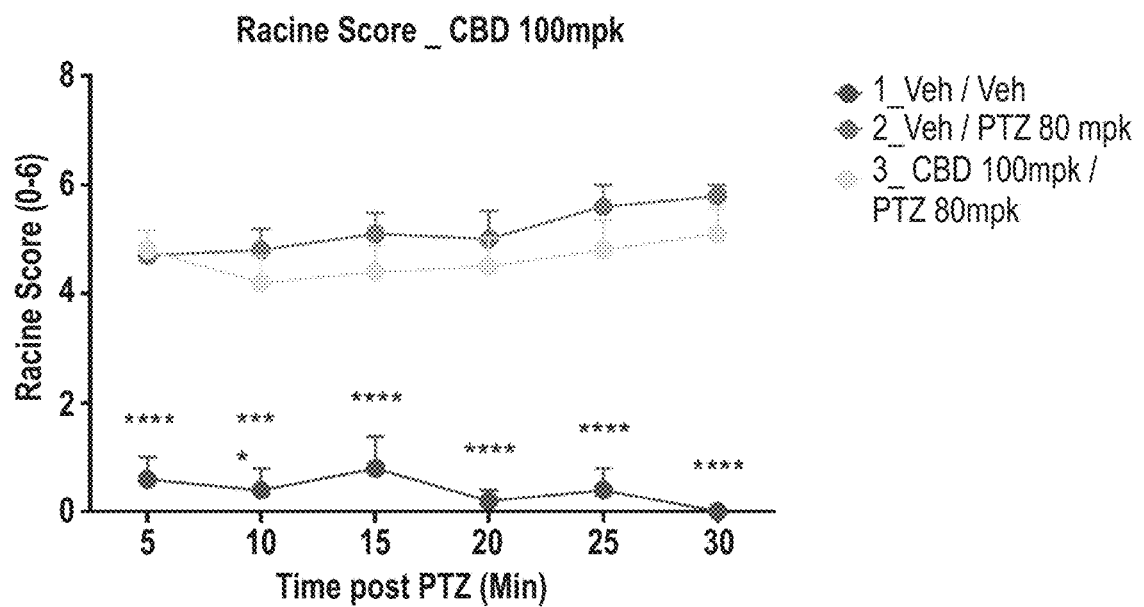
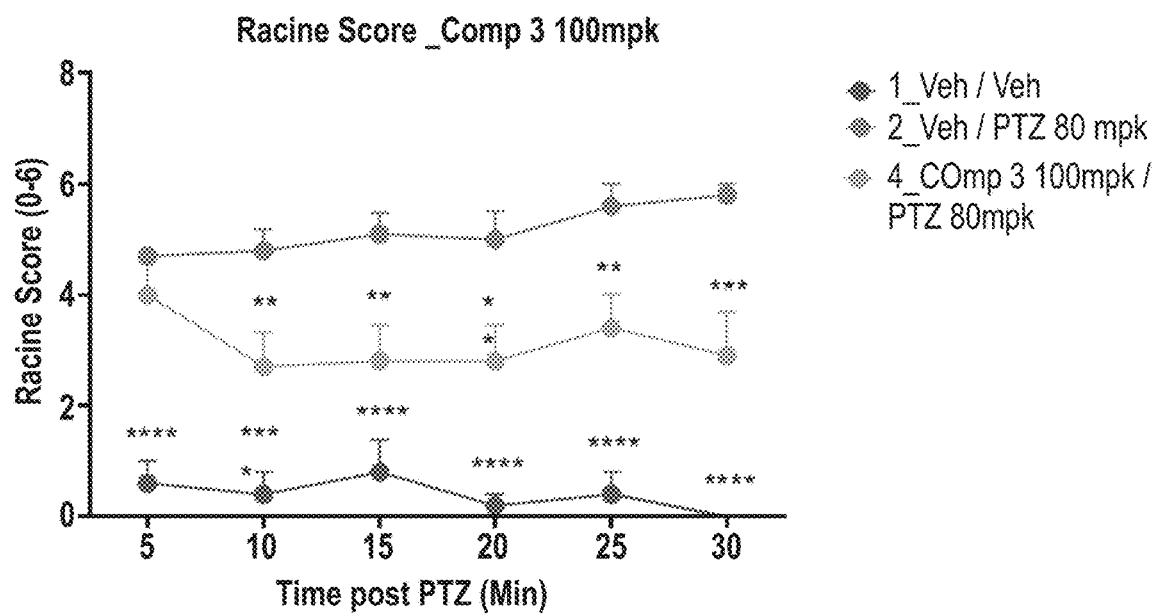

FIG. 33
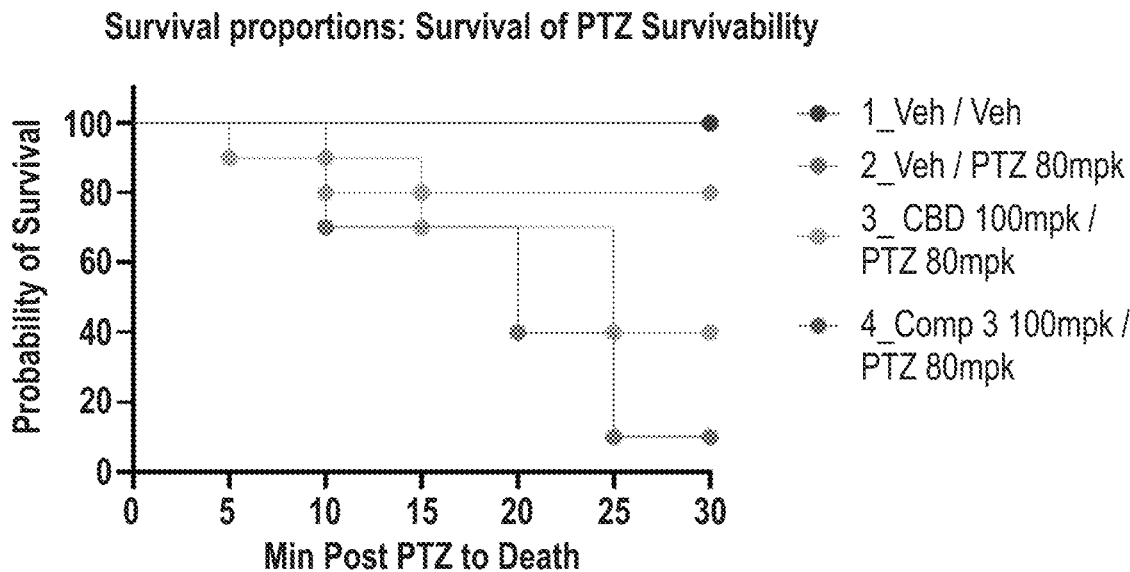
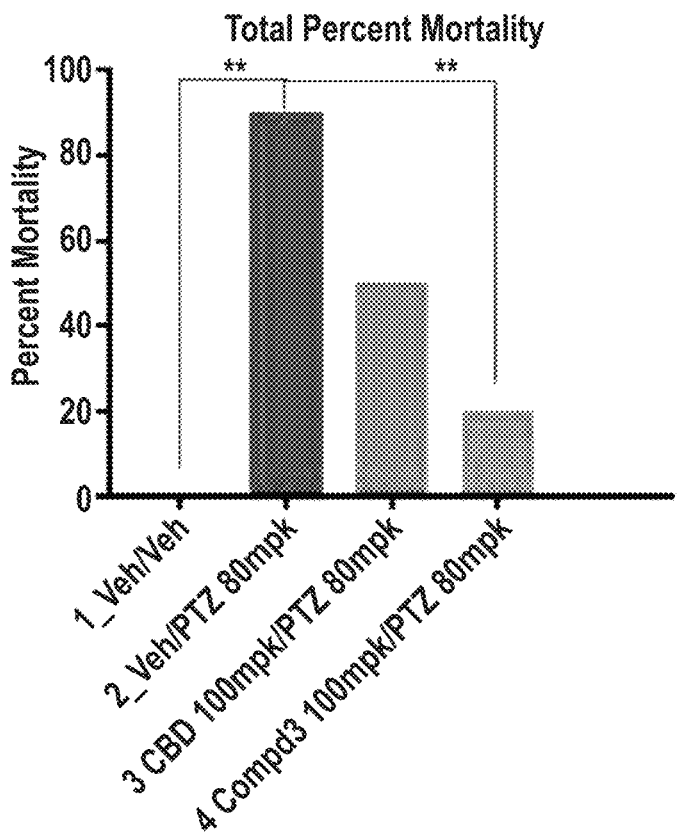

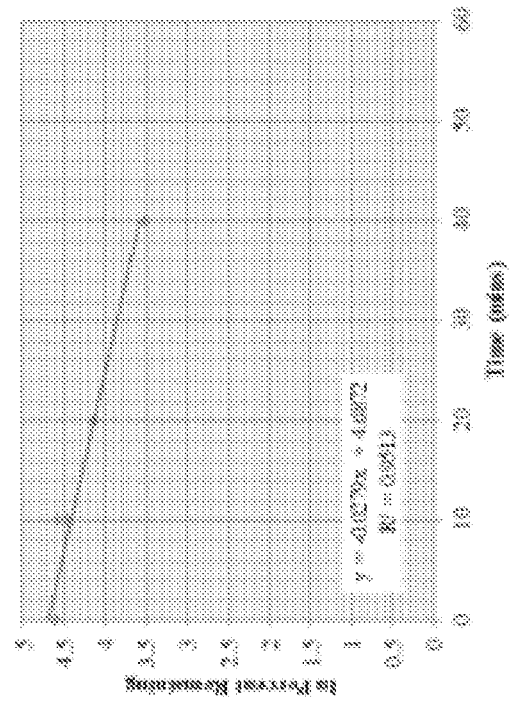
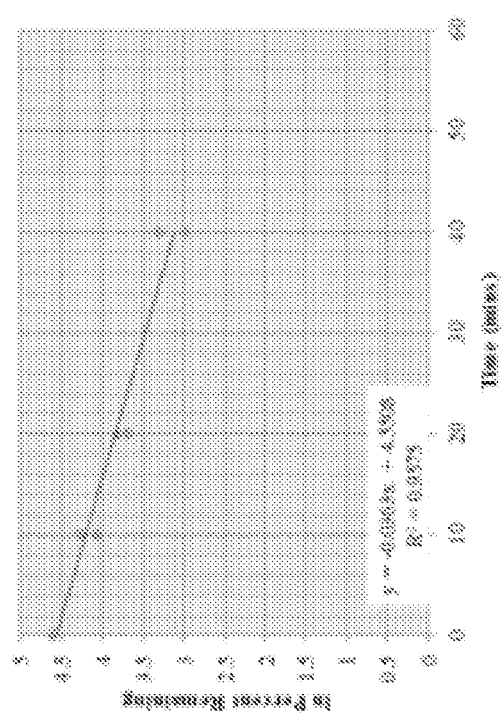
FIG. 35

CANNABINOID DERIVATIVES AND THEIR USE

CROSS-REFERENCE TO RELATED APPLICATIONS

This application is a Continuation of International Application No. PCT/US2022/074534, filed Aug. 4, 2022, which claims priority to U.S. Provisional Application No. 63/229,442 filed on Aug. 4, 2021, the contents of each of which are hereby incorporated by reference in their entireties for all purposes.

BACKGROUND

*Cannabis* plants contain various substances of medicinal interest, called cannabinoids, such as Δ9-tetrahydrocannabinol (D9-THC), Δ8-tetrahydrocannabinol (D8-THC), tetrahydrocannabinol acid (THC-A), tetrahydrocannabivarin (THCV), tetrahydrocannabivarin acid (THCV-A), cannabidiol (CBD), cannabidiol acid (CBD-A), cannabicromene (CBC), cannabidivarine (CBDV), canabidivine (CBDV)-A), cannabigerol (CBG), cannabigerol acid (CBG-A), cannabigerovarin (CBGV), cannabinol (CBN), cannabinovarin (CBNV), among others.

Their use has been intensively investigated for the treatment of epilepsy, nausea, vomiting, lack of appetite, pain and inflammatory diseases, and mental health disorders among other conditions.

Cannabinoids are primarily metabolized in the liver, especially by cytochrome P450 mixed-function oxidases. For example, CBD is extensively metabolized by the liver via CYP450 enzymes and the UGT enzymes. The major CYP450 isoforms responsible for the phase I metabolism of CBD are CYP2C19 and CYP3A4. The UGT isoforms responsible for the phase II conjugation of CBD are UGT1A7, UGT1A9 and UGT2B7.

There is a need for cannabinoid derivatives with increased bioavailability, especially oral bioavailability, and more efficient drug delivery and compositions and uses thereof for the treatment of various diseases or disorders, such as autoimmune diseases, chronic inflammatory diseases and mental health disorders. The need for increased oral bioavailability is evidenced by the oral dose levels and liver monitoring recommendations for Epidiolex (CBD), approved in the US in 2018 for the treatment of epilepsy disorders Lennox-Gastaut or Dravet syndrome. The typical oral dose is 2.5 mg/kg twice daily, which can be increased based upon tolerance and effect to 5 mg/kg twice daily and to a maximum of 10 mg/kg twice daily. There are numerous dose related side effects, hepatotoxicity markers are commonly elevated including 13% of patients exhibiting 3× or more the upper limit of normal (ULN) in prelicensure studies for Epidiolex®. The present invention discloses derivatives of cannabinoids that enhance oral bioavailability and efficacy in animal models compared to the natural cannabinoid molecule.

SUMMARY

In embodiments, the present disclosure relates to cannabinoid derivatives, such as alkylated derivatives of CBG and CBD, as well as pharmaceutical compositions thereof and uses thereof in treating various diseases and disorders.

In embodiments, the present disclosure provides a method of treating a chronic inflammatory disease, cancer, or mental health disorder in a subject in need thereof, comprising administering a compound of Formula (I), or a pharmaceutically acceptable salt thereof

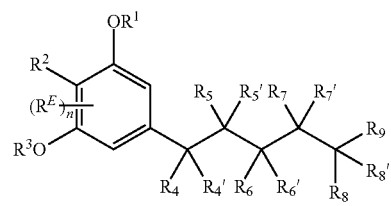

(I)

wherein:

$R^1$ and $R^3$ are independently a hydrogen, alkyl, alkyl-OH, or alkenyl; provided that at least one of $R^1$ and $R^3$ is not hydrogen;

$R^2$ is

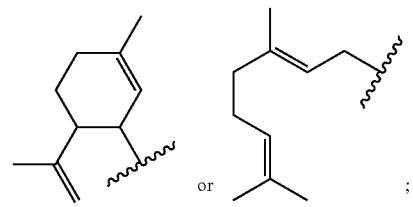 [SMILES: *C1C=C(C)CCC1C(=C)C ; *C/C=C(\C)CCC=C(C)C]

;

$R^E$ is hydroxy, halo, $-NR^A R^B$, cyano, nitro, alkyl, -haloalkyl, haloalkoxy or alkoxy;

$R^4$, $R^{4'}$, $R^5$, $R^{5'}$, $R^6$, $R^{6'}$, $R^7$, $R^{7'}$, $R^8$, $R^{8'}$, $R^9$ are each independently selected from the group consisting of hydrogen, $-OH$, alkyl, alkoxy, $-NR^A R^B$, and halogen;

$R^A$ and $R^B$ are each independently hydrogen or -alkyl; and n is 0, 1, or 2.

In embodiments of the methods of the present disclosure, the compound of Formula (I) is a compound of Formula (II):

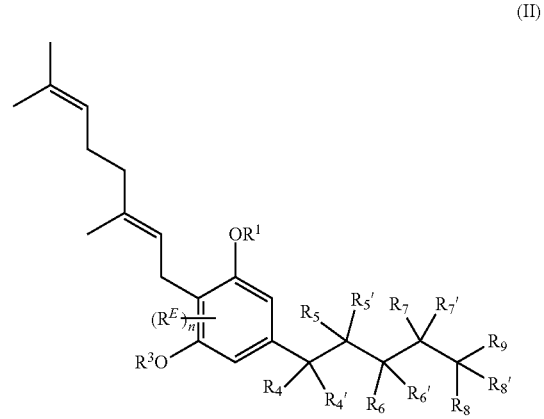

(II)

wherein the variables (i.e., $R^1$, $R^E$, n, $R^3$, $R^4$, $R^{4'}$, $R^5$, $R^{5'}$, $R^6$, $R^{6'}$, $R^7$, $R^{7'}$, $R^8$, $R^{8'}$, and $R^9$ are defined herein.

In embodiments of the methods of the present disclosure, the compound of Formula (I) is a compound of Formula (III):

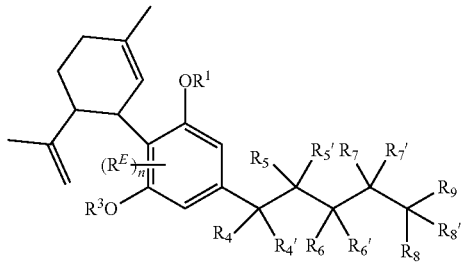

(III)

wherein the variables (i.e., $R^1$, $R^E$, n, $R^3$, $R^4$, $R^{4'}$, $R^5$, $R^{5'}$, $R^6$, $R^{6'}$, $R^7$, $R^{7'}$, $R^8$, $R^{8'}$, and $R^9$ are defined herein.

In embodiments, the present disclosure provides a method of treating a chronic inflammatory disease, cancer, or mental health disorder in a subject in need thereof, comprising administering a compound selected from the group consisting of

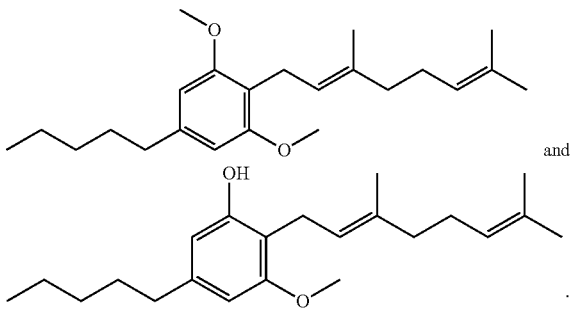

and

In embodiments, provided herein is pharmaceutical composition comprising a compound of Formula (I):

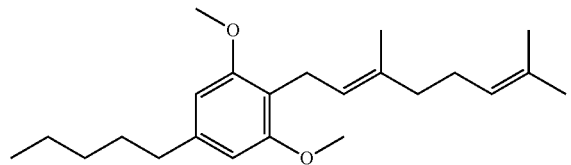

(I)

or a pharmaceutically acceptable salt thereof and a pharmaceutically acceptable carrier.

In embodiments, the present disclosure provides a method of treating a mental health disorder in a subject in need thereof, comprising administering a compound of the present disclosure (e.g., a compound of Formula (I)), or a pharmaceutical composition comprising a compound of the present disclosure.

In embodiments, the present disclosure provides a method of treating a chronic inflammatory disease in a subject in need thereof, comprising administering a compound of the present disclosure (e.g., a compound of Formula (I)), or a pharmaceutical composition comprising a compound of the present disclosure.

In embodiments, the present disclosure provides one or more compounds described in Table 1.

In embodiments, the present disclosure provides a pharmaceutical composition comprising one or more compounds described in Table 1, and a pharmaceutically acceptable carrier.

BRIEF DESCRIPTION OF THE DRAWINGS

FIG. 10 shows Group 3 Compound 2 glucuronide Plasma Concentration vs Time Profile from the PK study described in Example 5.

FIG. 13 shows a summary of metabolites M1-M6 of CBG in hepatocyte stability assay samples.

FIG. 14 shows a summary of metabolites M7-M12 of CBG in hepatocyte stability assay samples.

FIG. 31 is a graph showing Racine scores over 5 minute intervals for 30 minutes in the study described in Example 9.

FIG. 33 is a graph showing survival effects in the study described in Example 9.

FIG. 35 is a graph depicting the stability of Compound 1 in the presence of UGT1A9.

DEFINITIONS

Figure 1:
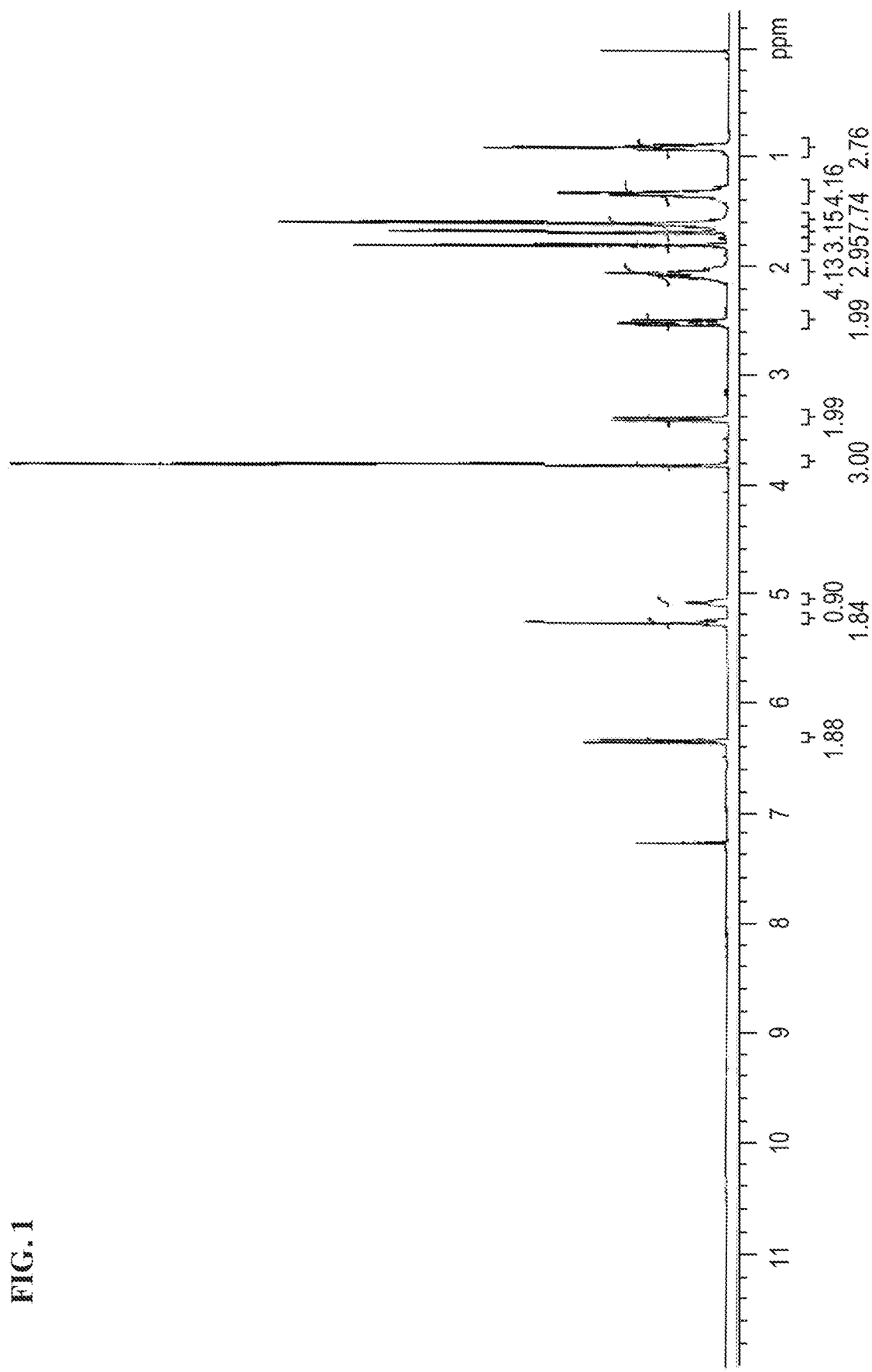
FIG. 1 shows a $^1$H NMR (CDCl$_3$) spectrum of Compound 1.

Throughout this disclosure, various patents, patent applications and publications are referenced. The disclosures of these patents, patent applications and publications in their entireties are incorporated into this disclosure by reference for all purposes in order to more fully describe the state of the art as known to those skilled therein as of the date of this disclosure. This disclosure will govern in the instance that there is any inconsistency between the patents, patent applications and publications cited and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs.

The term "about" when immediately preceding a numerical value means a range (e.g., plus or minus 10% of that value). For example, "about 50" can mean 45 to 55, "about 25,000" can mean 22,500 to 27,500, etc., unless the context of the disclosure indicates otherwise, or is inconsistent with such an interpretation. For example in a list of numerical values such as "about 49, about 50, about 55, . . . ", "about 50" means a range extending to less than half the interval(s) between the preceding and subsequent values, e.g., more than 49.5 to less than 50.5. Furthermore, the phrases "less than about" a value or "greater than about" a value should be understood in view of the definition of the term "about" provided herein. Similarly, the term "about" when preceding a series of numerical values or a range of values (e.g., "about 10, 20, 30" or "about 10-30") refers, respectively to all values in the series, or the endpoints of the range.

The term "pharmaceutically acceptable salts" includes both acid and base addition salts. Pharmaceutically acceptable salts include those obtained by reacting the active compound functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. Those skilled in the art will further recognize that acid addition salts may be prepared by reaction of the compounds with the appropriate inorganic or organic acid via any of a number of known methods.

As used herein, a "subject" can be a human, non-human primate, mammal, rat, mouse, cow, horse, pig, sheep, goat, dog, cat and the like.

"Mammal" includes humans and both domestic animals such as laboratory animals (e.g., mice, rats, monkeys, dogs, etc.) and household pets (e.g., cats, dogs, swine, cattle, sheep, goats, horses, rabbits), and non-domestic animals such as wildlife and the like.

The term "treating" as used herein with regard to a subject or patient, refers to improving at least one symptom of the patient's disorder. Treating can be improving, or at least partially ameliorating a disorder or an associated symptom of a disorder.

The terms "effective amount" and "therapeutically effective amount" are used interchangeably in this disclosure and refer to an amount of a compound, or a salt thereof, (or pharmaceutical composition containing the compound or salt) that, when administered to a patient, is capable of performing the intended result. The "effective amount" will vary depending on the active ingredient, the state, disorder, or condition to be treated and its severity, and the age, weight, physical condition and responsiveness of the mammal to be treated.

The term "therapeutically effective" applied to dose or amount refers to that quantity of a compound or pharmaceutical formulation that is sufficient to result in a desired clinical benefit after administration to a patient in need thereof.

The term "carrier" or "vehicle" as used interchangeably herein encompasses carriers, excipients, adjuvants, and diluents or a combination of any of the foregoing, meaning a material, composition or vehicle, such as a liquid or solid filler, diluent, excipient, solvent or encapsulating material involved in carrying or transporting a pharmaceutical agent from one organ, or portion of the body, to another organ or portion of the body. In addition to the adjuvants, excipients and diluents known to one skilled in the art, the carrier includes nanoparticles of organic and inorganic nature.

When a range of values is listed, it is intended to encompass each value and sub-range within the range. For example, "$C_1$-$C_6$ alkyl" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" or "alkyl group" refers to a fully saturated, straight or branched hydrocarbon chain having from one to twelve carbon atoms, and which is attached to the rest of the molecule by a single bond. Alkyls comprising any number of carbon atoms from 1 to 30 are included. For example, an alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{30}$ alkyl includes all the foregoing moieties, but also includes $C_{11}$-$C_{30}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

As used herein, the term "halo" refers to fluoro, chloro, bromo, or iodo.

"Haloalkyl" refers to an alkyl, as defined herein, that is substituted by one or more halo radicals, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group can be optionally substituted.

"Alkoxy" refers to a group of the formula —$OR_a$ where $R_a$ is an alkyl, alkenyl or alkynyl as defined above containing one to twelve carbon atoms. Unless stated otherwise specifically in the specification, an alkoxy group can be optionally substituted.

"Alkenyl" or "alkenyl group" refers to a straight or branched hydrocarbon chain having from two to twelve carbon atoms and having one or more carbon-carbon double bonds. Each alkenyl group is attached to the rest of the molecule by a single bond. Alkenyl group comprising any number of carbon atoms from 2 to 12 are included. An alkenyl group comprising up to 12 carbon atoms is a $C_2$-$C_{12}$ alkenyl, an alkenyl comprising up to 10 carbon atoms is a $C_2$-$C_{10}$ alkenyl, an alkenyl group comprising up to 6 carbon atoms is a $C_2$-$C_6$ alkenyl and an alkenyl comprising up to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_2$-$C_{12}$ alkenyl includes all the foregoing moieties, but also includes $C_{11}$ and $C_{12}$ alkenyls.

Non-limiting examples of $C_2$-$C_{12}$ alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Unless stated otherwise specifically in the specification, an alkyl group can be optionally substituted.

"haloalkoxy" refers to an alkoxy radical, as defined herein, that is substituted by one or more halo radicals, as defined above, e.g., —$OCF_3$, —$OCHF_2$, —$OCH_2F$, —$OCF_2CF_3$, or —$OCH_2CF_3$, and the like. Unless stated otherwise specifically in the specification, a haloalkyl group can be optionally substituted.

The term "substituted" used herein means any of the groups described herein (e.g., alkyl, haloalkyl, alkoxy and/or alkenyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted" also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents.

DETAILED DESCRIPTION

The present disclosure provides cannabinoid derivatives, such as cannabigerol (CBG), cannabidiol (CBD), derivatives for use in the treatment of various diseases or disorders.

There are a number of therapeutic conditions which may be treated effectively by cannabinoids including, for example, cancer pain, cancer, colorectal cancer, migraine, appetite stimulation, multiple sclerosis, spinal cord injury, peripheral neuropathy, other neurogenic pain, rheumatoid arthritis, inflammatory bowel diseases, psychotic disorders (schizophrenia), anxiety, epilepsy & movement disorders, neurodegenerative disorders, stroke, head injury, appetite suppression.

The activity of the endocannabinoid system (ECS) within the CNS is essential for normal mental health. $CB_1$ receptors are densely expressed in the cortex, hippocampus, amygdala, basal ganglia, and cerebellum. Of relevance to schizophrenia, $CB_1$ modulates release of dopamine and glutamate (as well as gamma-aminobutyric acid, serotonin, glycine, acetylcholine, and noradrenaline), and in participants their expression is increased in prefrontal cortex and anterior cingulate cortex. $CB_1$ knockout mice show increased emotional reactivity, hypersensitivity to stress, reduced responsiveness to rewarding stimuli, increased aggression to intruders, enhanced development of learned helplessness, impaired extinction of aversive memories, and social withdrawal (Robson et al, *Current Pharmaceutical Design*, 2014; 20(13): 2194-204).

An extensive review of the antipsychotic properties of CBD by lseger et al. in 2015 (*Schizophr. Res. Mar.* 2015; 162(1-3):153-61), which reviewed and referenced 29 studies incorporated by reference, concluded that CBD was an effective, safe and well tolerated antipsychotic compound, and thus may be a promising new agent in the treatment of schizophrenia. It has been postulated that CBD may have potential utility in schizophrenia, not only as an antipsychotic but also in the alleviation of the metabolic and inflammatory abnormalities associated with the disease. CBD has also demonstrated efficacy in anxiety. Unfortunately, CBD is not easily developable as an oral medication due to its poor bioavailability, which necessitates high oral doses leading to e.g., economic waste, risk of toxicity, and unpredictable responses. See for example, the clinical study described in McGuire et al. (Philip McGuire et al. *Am J Psychiatry* 2018; 175:225-231) where Schizophrenia patients were administered high doses of 1 gram of CBD.

Inflammatory bowel disease (IBD) comprises the chronic relapsing inflammatory disorders Crohn's disease (CD) and ulcerative colitis (UC). It is characterized by abdominal pain, diarrhoea, bleeding and malabsorption. Its incidence is increasing worldwide, and the disease remains incurable. The incidence and prevalence of IBD has increased in the past 50 years, up to 8-14/100,000 and 120-200/100,000 cases, respectively, for UC and 6-15/100,000 and 50-200/100,000 cases, respectively, for CD. Conventional therapies for IBD include antibodies treatments such as: ENTYVIO® (vedolizumab) and Stelara (ustekinumab), aminosalicylates, corticosteroids, thiopurines, methotrexate, and anti-tumor necrosis factor agents. Although these drugs may be effective, their long-term use can induce severe side effects that have detrimental impact on life quality of patients, and antibody treatments often require hospitalization and high treatment costs. Hence, new approaches with fewer side effects for the treatment of IBD are needed.

Studies have shown that *Cannabis* use is common in patients with IBD for symptom relief (Naftali T et al. *Isr. Med. Assoc. J.* 2011; 13:455-8; Lal S et al. *Eur. J. Gastroenterol. Hepatol.* 2011; 23:891-6). A pilot prospective study found that treatment with inhaled *Cannabis* improved quality of life in patients with long-standing CD and UC (Lahat A et al. *Digestion* 2012; 85:1-8). In Israel, inhaled *Cannabis* has been legally registered for palliative treatment of both CD and UC. D9-tetrahydrocannabinol (D9-THC), the main *Cannabis* psychotropic ingredient which activates cannabinoid (CB1 and CB2) receptors, and cannabidiol (CBD), the best studied among the so-called non-psychotropic cannabinoids, have been previously shown to ameliorate experimental colitis in rodents (Borrelli F et al. *J. Mol. Med.* 2009; 87:1111-21; Jamontt J M et al, *Br. J. Pharmacol.* 2010; 60:712-23; Schicho R et al. *Pharmacology* 2012; 89:149-55). A study by Borelli et al (*Biochemical Pharmacology*, 85 (2013) 1306-1316) demonstrated that cannabinoid CBG exerts protective effects in a murine experimental model of IBD.

In embodiments, the compounds of the present disclosure are designed to minimize glucuronidation. In embodiments, the compounds of the present disclosure are designed to minimize glucuronidation but do not convert to the parent compound e.g., cannabigerol (CBG), cannabidiol (CBD).

In embodiments, the cannabinoid derivatives of the present disclosure provide higher cannabinoid concentration in the plasma or target cells/organ such as the GI and colon and brain when compared to the parent cannabinoid. For example, CBG analogs of the present disclosure provide higher concentrations of the CBG analog in the plasma or target cells/organ such as the GI and colon when compared to CBG, or CBD analogs of the present disclosure provide higher CBD concentrations of the CBD analog in the plasma or target cells/organ such as the GI and colon when compared to CBD.

Compounds

In embodiments, provided herein is a compound of Formula (IV):

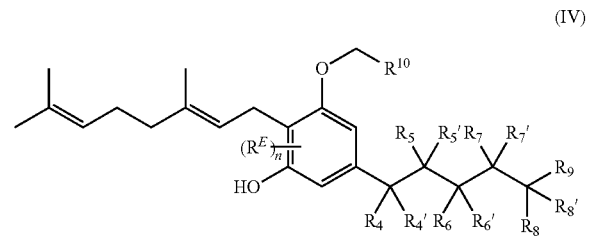

(IV)

wherein:
$R_{10}$ is $C_{2-6}$alkyl, $C_{1-6}$alkyl-OH, or $C_{2-6}$alkenyl;
$R^E$ is hydroxy, halo, $-NR^AR^B$, cyano, nitro, alkyl, -haloalkyl, haloalkoxy or alkoxy;
$R^4$, $R^{4'}$, $R^5$, $R^{5'}$, $R^6$, $R^{6'}$, $R^7$, $R^{7'}$, $R^8$, $R^{8'}$, $R^9$ are each independently selected from the group consisting of hydrogen, $-OH$, alkyl, alkoxy, $-NR^AR^B$, and halogen;
$R^A$ and $R^B$ are each independently hydrogen or alkyl; and n is 0, 1, or 2.

In embodiments, $R_{10}$ is $-CH_2CH_3$, $-CH_2CH_2CH_3$, $-CH=CH_2$, or $-CH_2OH$.

In embodiments, $R^4$, $R^{4'}$ are hydrogen. In embodiments, $R^5$, $R^{5'}$ are hydrogen. In embodiments, $R^6$, $R^{6'}$ are hydrogen. In embodiments, $R^7$, $R^{7'}$ are hydrogen. In embodiments, $R^8$, and $R^{8'}$.

In embodiments, $R^4$, $R^{4'}$, $R^5$, $R^{5'}$, $R^6$, $R^{6'}$, $R^7$, $R^{7'}$, $R^8$, and $R^{8'}$ are hydrogen.

In embodiments of the compounds of the present disclosure, $R^4$, $R^{4'}$, $R^5$, $R^{5'}$, $R^6$, $R^{6'}$, $R^7$, $R^{7'}$, $R^8$, and $R^{8'}$ are hydrogen and $R^9$ is $C_{1-6}$ alkyl.

In embodiments of the compounds of the present disclosure, $R^4$, $R^{4'}$, $R^5$, $R^{5'}$, $R^6$, $R^{6'}$, $R^7$, $R^{7'}$, $R^8$, and $R^{8'}$ are hydrogen and $R^9$ is —CH$_2$CH$_3$.

In embodiments, provided herein is a compound of Formula (V):

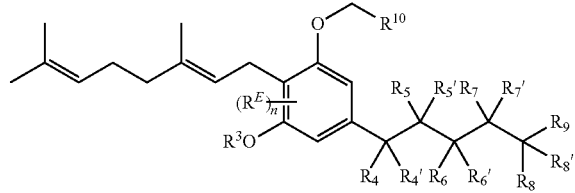

wherein:
$R_{10}$ is $C_{1-3}$ alkyl optionally substituted with —OH, or $C_{2-6}$ alkenyl;
$R^3$ is $C_{1-4}$ alkyl optionally substituted with —OH, or $C_{2-6}$ alkenyl;
$R^E$ is hydroxy, halo, —NR$^A$R$^B$, cyano, nitro, alkyl, -haloalkyl, haloalkoxy or alkoxy;
$R^4$, $R^{4'}$, $R^5$, $R^{5'}$, $R^6$, $R^{6'}$, $R^7$, $R^{7'}$, $R^8$, $R^{8'}$, $R^9$ are each independently selected from the group consisting of hydrogen, —OH, alkyl, alkoxy, —NR$^A$R$^B$, and halogen;
$R^A$ and $R^B$ are each independently hydrogen or alkyl; and
n is 0, 1, or 2.

In embodiments of the compounds of the present disclosure, $R^4$, $R^{4'}$, $R^5$, $R^{5'}$, $R^6$, $R^{6'}$, $R^7$, $R^{7'}$, $R^8$, and $R^{8'}$ are hydrogen.

In embodiments, $R^4$, $R^{4'}$ are hydrogen. In embodiments, $R^5$, $R^{5'}$ are hydrogen. In embodiments, $R^6$, $R^{6'}$ are hydrogen. In embodiments, $R^7$, $R^{7'}$ are hydrogen. In embodiments, $R^8$, and $R^{8'}$.

In embodiments of the compounds of the present disclosure, $R^4$, $R^{4'}$, $R^5$, $R^{5'}$, $R^6$, $R^{6'}$, $R^7$, $R^{7'}$, $R^8$, and $R^{8'}$ are hydrogen and $R^9$ is $C_{1-6}$ alkyl.

In embodiments of the compounds of the present disclosure, $R^4$, $R^{4'}$, $R^5$, $R^{5'}$, $R^6$, $R^{6'}$, $R^7$, $R^{7'}$, $R^8$, and $R^{8'}$ are hydrogen and $R^9$ is —CH$_2$CH$_3$.

In embodiments, $R_{10}$ is CH$_3$, $R_{10}$ is —CH$_2$CH$_3$, —CH$_2$CH$_2$CH$_3$, —CH=CH$_2$, or —CH$_2$OH.

In embodiments, $R^3$ is —CH$_2$CH$_3$, —CH$_2$CH$_2$CH$_3$, —CH$_2$CH$_2$CH$_2$CH$_3$, —CH$_2$—CH=CH$_2$, or —CH$_2$CH$_2$—OH.

In embodiments, provided herein is one or more compounds selected from Table 1.

In embodiments, provided herein is one or more pharmaceutically acceptable salts of a compound selected from Table 1.

TABLE 1-continued

Compounds

| No. | Structure |
|---|---|
| 16 | 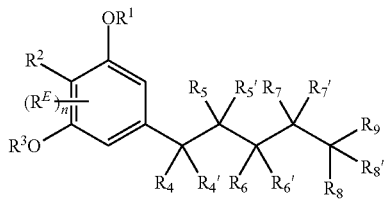 |
| 18 | 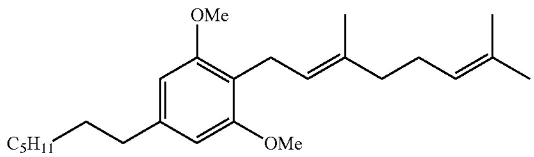 |
| 19 | 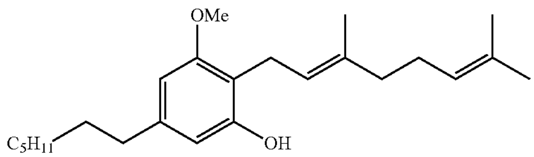 |

Compositions

In some embodiments of the present disclosure, a pharmaceutical composition comprises a therapeutically effective amounts of one or more compounds of the present disclosure (e.g., a compound of Formula (I), (II), (III), (IV), or (V), Table 1 or Table 2) or a pharmaceutically acceptable salt thereof and a pharmaceutically acceptable carrier.

In some embodiments of the present disclosure, a pharmaceutical composition comprises a therapeutically effective amounts of a compound of Formula (I) or a pharmaceutically acceptable salt thereof and a pharmaceutically acceptable carrier.

(I)

wherein:
$R^1$ and $R^3$ are independently a hydrogen, optionally substituted alkyl, or alkenyl;
$R^2$ is

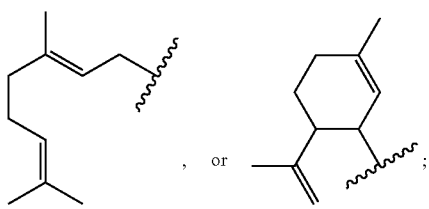 [SMILES: *C/C=C(\C)CCC=C(C)C ; *C1C=C(C)CCC1C(=C)C]

$R^E$ is hydroxy, halo, —$NR^AR^B$, cyano, nitro, alkyl, -haloalkyl, haloalkoxy or alkoxy;
$R^4$, $R^{4'}$, $R^5$, $R^{5'}$, $R^6$, $R^{6'}$, $R^7$, $R^{7'}$, $R^8$, $R^{8'}$, $R^9$ are each independently selected from the group consisting of hydrogen, —OH, alkyl, alkoxy, —$NR^AR^B$, and halogen;
$R^A$ and $R^B$ are each independently hydrogen or alkyl; and
n is 0, 1, or 2.

In some embodiments, a pharmaceutical composition, as described herein, comprises one or more compounds selected from Table 1, or a pharmaceutically acceptable salt thereof or stereoisomer thereof.

In some embodiments, a pharmaceutical composition, as described herein, comprises one or more compounds selected from Table 1, or a pharmaceutically acceptable salt thereof.

In some embodiments of the present disclosure, a pharmaceutical composition comprising one or more compounds of the present disclosure or a pharmaceutically acceptable salt thereof, and a pharmaceutically acceptable excipient or adjuvant is provided. The pharmaceutically acceptable excipients and adjuvants are added to the composition or formulation for a variety of purposes. In some embodiments, a pharmaceutical composition comprising one or more compounds disclosed herein, or a pharmaceutically acceptable salt thereof, further comprise a pharmaceutically acceptable carrier. In some embodiments, a pharmaceutically acceptable carrier includes a pharmaceutically acceptable excipient, binder, and/or diluent. In some embodiments, suitable pharmaceutically acceptable carriers include, but are not limited to, inert solid fillers or diluents and sterile aqueous or organic solutions. In some embodiments, suitable pharmaceutically acceptable excipients include, but are not limited to, water, salt solutions, alcohol, polyethylene glycols, gelatin, lactose, amylase, magnesium stearate, talc, silicic acid, viscous paraffin, and the like.

For the purposes of this disclosure, the compounds of the present disclosure can be formulated for administration by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters.

Generally, the compounds of the present disclosure are administered in a therapeutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

Therapeutic Use

In embodiments, the present disclosure provides a method of treating a chronic inflammatory disease, cancer, or a mental health disorder in a subject in need thereof, comprising administering a compound of Formula (I), or a pharmaceutically acceptable salt thereof

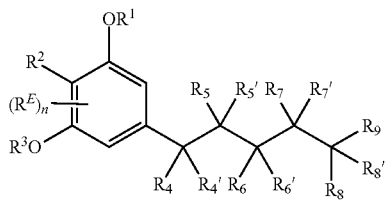

(I)

wherein:
R$^1$ and R$^3$ are independently a hydrogen, optionally substituted alkyl, or alkenyl;
R$^2$ is

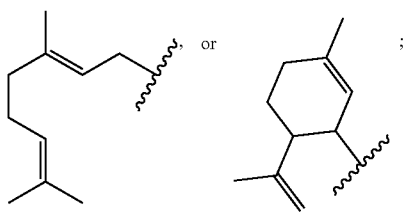 [SMILES: *C/C=C(\C)CCC=C(C)C ; *C1C=C(C)CCC1C(=C)C]

, or ;

R$^E$ is hydroxy, halo, —NR$^A$R$^B$, cyano, nitro, alkyl, -haloalkyl, haloalkoxy or alkoxy;
R$^4$, R$^{4'}$, R$^5$, R$^{5'}$, R$^6$, R$^{6'}$, R$^7$, R$^{7'}$, R$^8$, R$^{8'}$, R$^9$ are each independently selected from the group consisting of hydrogen, —OH, alkyl, alkoxy, —NR$^A$R$^B$, and halogen;
R$^A$ and R$^B$ are each independently hydrogen or alkyl; and
n is 0, 1, or 2.

In embodiments, the present disclosure provides a method of treating a chronic inflammatory disease, cancer, or a mental health disorder in a subject in need thereof, comprising administering a compound of Formula (I), or a pharmaceutically acceptable salt thereof

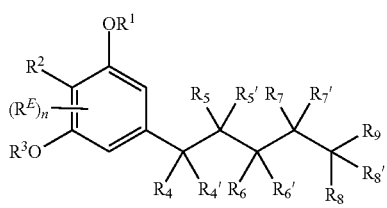

(I)

wherein:
R$^1$ and R$^3$ are independently a hydrogen, optionally substituted alkyl or alkenyl;
R$^2$ is

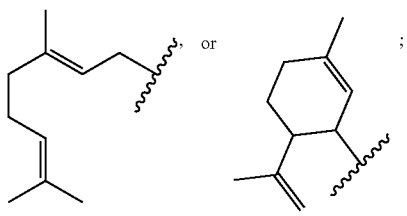 [SMILES: *C/C=C(\C)CCC=C(C)C ; *C1C=C(C)CCC1C(=C)C]

, or ;

R$^E$ is hydroxy, halo, —NR$^A$R$^B$, cyano, nitro, alkyl, -haloalkyl, haloalkoxy or alkoxy;
R$^4$, R$^{4'}$, R$^5$, R$^{5'}$, R$^6$, R$^{6'}$, R$^7$, R$^{7'}$, R$^8$, and R$^{8'}$ are each independently selected from the group consisting of hydrogen, —OH, alkyl, alkoxy, —NR$^A$R$^B$, and halogen; and
R$^9$ is alkyl;
R$^A$ and R$^B$ are each independently hydrogen or alkyl; and
n is 0, 1, or 2.

In embodiments of the methods of the present disclosure, the compound of Formula (I) is

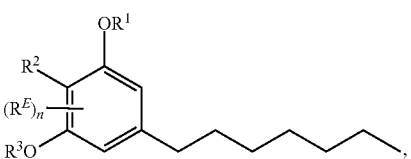

, or a pharmaceutically acceptable salt thereof wherein:
R$^1$ and R$^3$ are independently a hydrogen, optionally substituted alkyl or alkenyl;
R$^2$ is

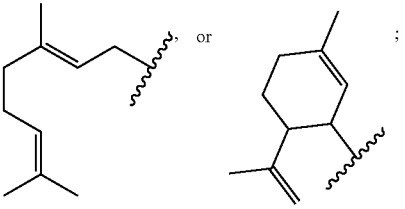 [SMILES: *C/C=C(\C)CCC=C(C)C ; *C1C=C(C)CCC1C(=C)C]

, or ;

R$^E$ is hydroxy, halo, —NR$^A$R$^B$, cyano, nitro, alkyl, -haloalkyl, haloalkoxy or alkoxy; and
n is 0, 1, or 2.

In embodiments, the present disclosure provides a method of treating a chronic inflammatory disease, cancer, or a mental health disorder in a subject in need thereof, comprising administering a compound of Formula (I), or a pharmaceutically acceptable salt thereof

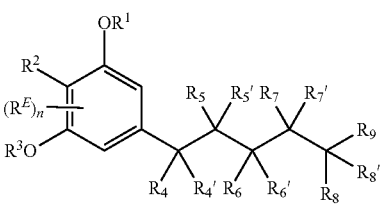

(I)

wherein:
R$^1$ and R$^3$ are independently a hydrogen, alkyl, alkyl-OH, or alkenyl; provided that at least one of R$^1$ and R$^3$ is not hydrogen;

$R^2$ is

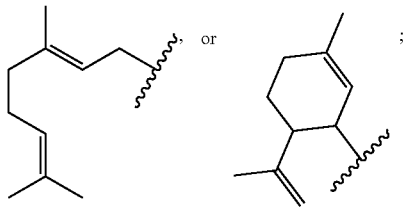

$R^E$ is hydroxy, halo, —$NR^AR^B$, cyano, nitro, alkyl, -haloalkyl, haloalkoxy or alkoxy;

$R^4$, $R^{4'}$, $R^5$, $R^{5'}$, $R^6$, $R^{6'}$, $R^7$, $R^{7'}$, $R^8$, $R^{8'}$, $R^9$ are each independently selected from the group consisting of hydrogen, —OH, alkyl, alkoxy, —$NR^AR^B$, and halogen;

$R^A$ and $R^B$ are each independently hydrogen or alkyl; and n is 0, 1, or 2.

In embodiments, the present disclosure provides a method of treating a chronic inflammatory disease, cancer, or a mental health disorder in a subject in need thereof, comprising administering a compound of Formula (I), or a pharmaceutically acceptable salt thereof

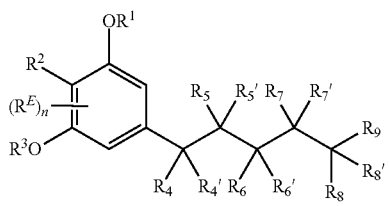

(I)

wherein:
$R^1$ and $R^3$ are independently a hydrogen or alkyl; provided that at least one of $R^1$ and $R^3$ is alkyl;
$R^2$ is

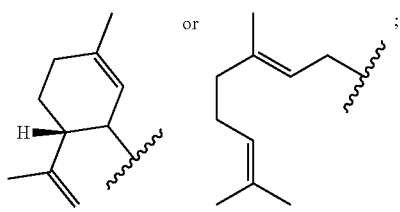 [SMILES: *C1C=C(C)CC[C@H]1C(=C)C ; *C/C=C(\C)CCC=C(C)C]

$R^E$ is hydroxy, halo, —$NR^AR^B$, cyano, nitro, alkyl, -haloalkyl, haloalkoxy or alkoxy;

$R^4$, $R^{4'}$, $R^5$, $R^{5'}$, $R^6$, $R^{6'}$, $R^7$, $R^{7'}$, $R^8$, $R^{8'}$, $R^9$ are each independently selected from the group consisting of hydrogen, —OH, alkyl, alkoxy, —$NR^AR^B$, and halogen;

$R^A$ and $R^B$ are each independently hydrogen or -alkyl; and n is 0, 1, or 2.

In embodiments, the present disclosure provides a method of treating a chronic inflammatory disease or mental health disorder in a subject in need thereof, comprising administering a compound of Formula (I), or a pharmaceutically acceptable salt thereof

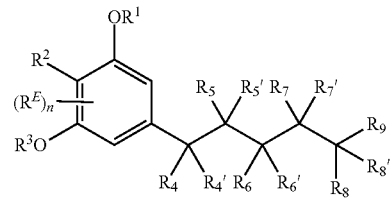

(I)

wherein:
$R^1$ and $R^3$ are independently a hydrogen or alkyl; provided that at least one of $R^1$ and $R^3$ is alkyl;
$R^2$ is

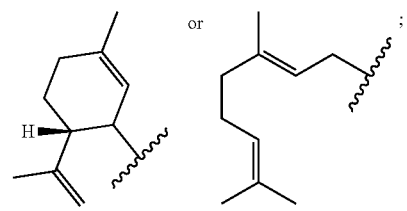 [SMILES: *C1C=C(C)CC[C@H]1C(=C)C ; *C/C=C(\C)CCC=C(C)C]

$R^E$ is hydroxy, halo, —$NR^AR^B$, cyano, nitro, alkyl, -haloalkyl, haloalkoxy or alkoxy;

$R^4$, $R^{4'}$, $R^5$, $R^{5'}$, $R^6$, $R^{6'}$, $R^7$, $R^{7'}$, $R^8$, $R^{8'}$, $R^9$ are each independently selected from the group consisting of hydrogen, —OH, alkyl, alkoxy, —$NR^AR^B$, and halogen;

$R^A$ and $R^B$ are each independently hydrogen or -alkyl; and n is 0, 1, or 2.

In embodiments of the compounds of Formula (I), $R^1$ and $R^3$ are each independently a hydrogen, alkyl optionally substituted with OH, or alkenyl.

In embodiments of the compounds of Formula (I), $R^1$ is hydrogen and $R^3$ is alkyl.

In embodiments of the compounds of Formula (I), $R^1$ is hydrogen and $R^3$ is —$C_{1-6}$alkyl.

In embodiments of the compounds of Formula (I), $R^1$ is hydrogen and $R^3$ is —$C_{2-6}$alkyl.

In embodiments of the compounds of Formula (I), $R^1$ is hydrogen and $R^3$ is —$C_{1-3}$alkyl.

In embodiments of the compounds of Formula (I), $R^1$ is hydrogen and $R^3$ is one or more substituents (e.g., 1, 2, 3, 4 5, or 6 substituents) selected from the group consisting of methyl, ethyl, propyl, butyl, —$CH_2$—CH=$CH_2$, and —$CH_2CH_2$—OH. In embodiments, $R^1$ is hydrogen and $R^3$ is methyl, ethyl, propyl, butyl, —$CH_2$—CH=$CH_2$, or —$CH_2CH_2$—OH.

In embodiments of the compounds of Formula (I), $R^1$ is hydrogen and $R^3$ is methyl.

In embodiments of the compounds of Formula (I), $R^1$ and $R^3$ are alkyl.

In embodiments of the compounds of Formula (I), $R^1$ and $R^3$ are independently —$C_{1-6}$alkyl.

In embodiments of the compounds of Formula (I), $R^1$ and $R^3$ are independently —$C_{1-3}$alkyl.

In embodiments of the compounds of Formula (I), $R^1$ and $R^3$ are each independently one or more substituents (e.g., 1, 2, 3, 4 5, or 6 substituents) selected from the group consisting of methyl, ethyl, propyl, butyl, —$CH_2$—CH=$CH_2$, and —$CH_2CH_2$—OH. In embodiments, $R^1$ and $R^3$ are each independently methyl, ethyl, propyl, butyl, —$CH_2$—CH=$CH_2$, or —$CH_2CH_2$—OH.

In embodiments of the compounds of Formula (I), $R^1$ and $R^3$ are methyl.

In embodiments of the compounds of Formula (I), $R^2$ is

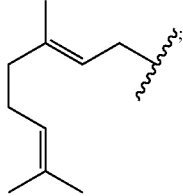 [SMILES: *C/C=C(\C)CCC=C(C)C]

In embodiments of the compounds of Formula (I), $R^2$ is

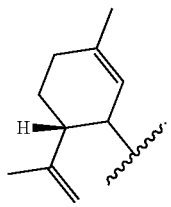 [SMILES: *C1C=C(C)CC[C@H]1C(=C)C]

In embodiments of the compounds of Formula (I), $R^2$ is

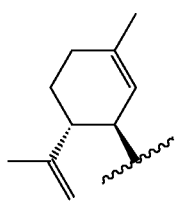 [SMILES: *[C@@H]1C=C(C)CC[C@H]1C(=C)C]

In embodiments of the compounds of Formula (I), $R^4$, $R^{4'}$, $R^5$, $R^{5'}$, $R^6$, $R^{6'}$, $R^7$, $R^{7'}$, $R^8$, $R^{8'}$, $R^9$ are each independently selected from the group consisting of hydrogen, —OH, alkyl, alkoxy, —$NR^AR^B$, and halogen.

In embodiments of the compounds of Formula (I), $R^4$, $R^{4'}$, $R^5$, $R^{5'}$, $R^6$, $R^{6'}$, $R^7$, $R^{7'}$, $R^8$, $R^{8'}$, $R^9$ are each hydrogen.

In embodiments of the compounds of Formula (I), $R^4$, $R^{4'}$, $R^5$, $R^{5'}$, $R^6$, $R^{6'}$, $R^7$, $R^{7'}$, $R^8$, and $R^{8'}$ are each hydrogen $R^9$ is —$CH_2CH_3$.

In embodiments of the compounds of Formula (I), $R^A$ and $R^B$ are each independently hydrogen or -alkyl.

In embodiments of the compounds of Formula (I), $R^A$ and $R^B$ are hydrogen. In embodiments, $R^A$ and $R^B$ are -alkyl.

In embodiments of the compounds of Formula (I), n is 0, 1, or 2. In embodiments, n is 0. In embodiments, n is 1. In embodiments, n is 2.

In embodiments of the methods of the present disclosure, the compound of Formula (I) is a compound of Formula (II):

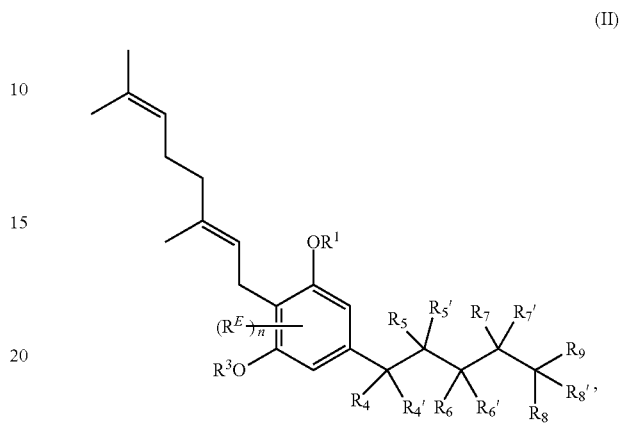

wherein $R^1$ and $R^3$ are independently a hydrogen, alkyl, alkyl-OH, or alkenyl; provided that at least one of $R^1$ and $R^3$ is not hydrogen;

$R^E$ is hydroxy, halo, —$NR^AR^B$, cyano, nitro, alkyl, -haloalkyl, haloalkoxy or alkoxy;

$R^4$, $R^{4'}$, $R^5$, $R^{5'}$, $R^6$, $R^{6'}$, $R^7$, $R^{7'}$, $R^8$, $R^{8'}$, $R^9$ are each independently selected from the group consisting of hydrogen, —OH, alkyl, alkoxy, —$NR^AR^B$, and halogen;

$R^A$ and $R^B$ are each independently hydrogen or alkyl; and n is 0, 1, or 2.

In embodiments of the compounds of Formula (II), $R^1$ is hydrogen and $R^3$ is alkyl.

In embodiments of the compounds of Formula (II), $R^1$ is hydrogen and $R^3$ is —$C_{1-6}$alkyl.

In embodiments of the compounds of Formula (II), $R^1$ is hydrogen and $R^3$ is methyl, ethyl, propyl, butyl, —$CH_2$—$CH$=$CH_2$, —$CH_2CH_2$—OH.

In embodiments of the compounds of Formula (II), $R^1$ and $R^3$ are alkyl.

In embodiments of the compounds of Formula (II), $R^1$ and $R^3$ are each independently —$C_{1-6}$alkyl.

In embodiments of the compounds of Formula (II), $R^1$ and $R^3$ are each independently methyl, ethyl, propyl, butyl, —$CH_2$—$CH$=$CH_2$, or —$CH_2CH_2$—OH.

In embodiments of the compounds of Formula (II), $R^4$, $R^{4'}$, $R^5$, $R^{5'}$, $R^6$, $R^{6'}$, $R^7$, $R^{7'}$, $R^8$, $R^{8'}$, $R^9$ are each hydrogen.

In embodiments of the compounds of Formula (II), $R^4$, $R^{4'}$, $R^5$, $R^{5'}$, $R^6$, $R^{6'}$, $R^7$, $R^{7'}$, $R^8$, and $R^{8'}$ are each hydrogen $R^9$ is —$CH_2CH_3$.

In embodiments of the compounds of Formula (II), n is 0, 1, or 2. In embodiments, n is 0. In embodiments, n is 1. In embodiments, n is 2.

In embodiments of the methods of the present disclosure, the compound of Formula (I) is a compound of Formula (III):

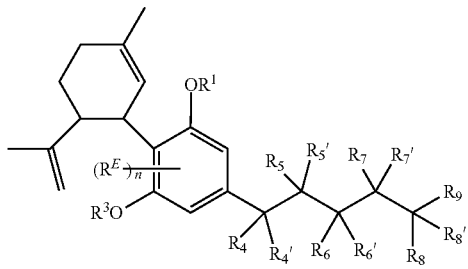

(III)

wherein
$R^1$ and $R^3$ are independently a hydrogen, alkyl, alkyl-OH, or alkenyl; provided that at least one of $R^1$ and $R^3$ is not hydrogen;
$R^E$ is hydroxy, halo, —$NR^AR^B$, cyano, nitro, alkyl, -haloalkyl, haloalkoxy or alkoxy;
$R^4$, $R^{4'}$, $R^5$, $R^{5'}$, $R^6$, $R^{6'}$, $R^7$, $R^{7'}$, $R^8$, $R^{8'}$, $R^9$ are each independently selected from the group consisting of hydrogen, —OH, alkyl, alkoxy, —$NR^AR^B$, and halogen;
$R^A$ and $R^B$ are each independently hydrogen or alkyl; and n is 0, 1, or 2.

In embodiments of the compounds of Formula (III), $R^1$ is hydrogen and $R^3$ is alkyl.

In embodiments of the compounds of Formula (III), $R^1$ is hydrogen and $R^3$ is —$C_{1-6}$alkyl.

In embodiments of the compounds of Formula (III), $R^1$ is hydrogen and $R^3$ is methyl.

In embodiments of the compounds of Formula (III), $R^1$ and $R^3$ are alkyl.

In embodiments of the compounds of Formula (III), $R^1$ and $R^3$ are independently —$C_{1-6}$alkyl.

In embodiments of the compounds of Formula (III), $R^1$ and $R^3$ are each independently methyl.

In embodiments of the compounds of Formula (III), $R^4$, $R^{4'}$, $R^5$, $R^{5'}$, $R^6$, $R^{6'}$, $R^7$, $R^{7'}$, $R^8$, $R^{8'}$, $R^9$ are each hydrogen.

In embodiments of the compounds of Formula (III), $R^4$, $R^{4'}$, $R^5$, $R^{5'}$, $R^6$, $R^{6'}$, $R^7$, $R^{7'}$, $R^8$, and $R^{8'}$ are each hydrogen and $R^9$ is —$CH_2CH_3$.

In embodiments of the compounds of Formula (III), n is 0, 1, or 2. In embodiments, n is 0. In embodiments, n is 1. In embodiments, n is 2.

In embodiments of the methods of the present disclosure, the methods comprise administering a compound of Formula (IV):

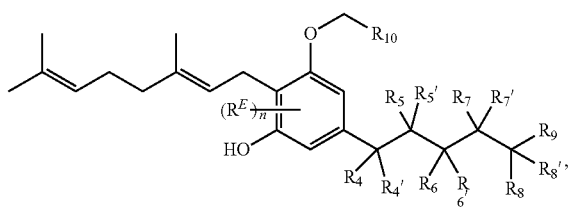

(IV)

or a pharmaceutically acceptable salt thereof
wherein:
$R_{10}$ is $C_{2-6}$alkyl, $C_{1-6}$alkyl-OH, or $C_{2-6}$alkenyl;
$R^E$ is hydroxy, halo, —$NR^AR^B$, cyano, nitro, alkyl, -haloalkyl, haloalkoxy or alkoxy;
$R^4$, $R^{4'}$, $R^5$, $R^{5'}$, $R^6$, $R^{6'}$, $R^7$, $R^{7'}$, $R^8$, $R^{8'}$, $R^9$ are each independently selected from the group consisting of hydrogen, —OH, alkyl, alkoxy, —$NR^AR^B$, and halogen;
$R^A$ and $R^B$ are each independently hydrogen or alkyl; and n is 0, 1, or 2.

In embodiments, $R_{10}$ is —$CH_2CH_3$, —$CH_2CH_2CH_3$, —$CH=CH_2$, or —$CH_2OH$.

In embodiments, $R^4$, $R^{4'}$ are hydrogen. In embodiments, $R^5$, $R^{5'}$ are hydrogen. In embodiments, $R^6$, $R^{6'}$ are hydrogen. In embodiments, $R^7$, $R^{7'}$ are hydrogen. In embodiments, $R^8$, and $R^{8'}$.

In embodiments, $R^4$, $R^{4'}$, $R^5$, $R^{5'}$, $R^6$, $R^{6'}$, $R^7$, $R^{7'}$, $R^8$, and $R^{8'}$ are hydrogen.

In embodiments of the compounds of the present disclosure, $R^4$, $R^{4'}$ $R^5$, $R^{5'}$, $R^6$, $R^{6'}$, $R^7$, $R^{7'}$, R, and $R^{8'}$ are hydrogen and $R^9$ is $C_{1-6}$ alkyl.

In embodiments of the compounds of the present disclosure, $R^4$, $R^{4'}$ $R^5$, $R^{5'}$, $R^6$, $R^{6'}$, $R^7$, $R^{7'}$, $R^8$, and $R^{8'}$ are hydrogen and $R^9$ is —$CH_2CH_3$.

In embodiments of the methods of the present disclosure, the methods comprise administerin a compound of Formula (V):

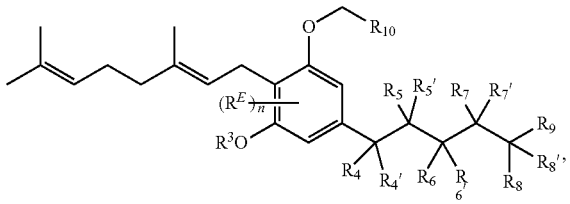

or a pharmaceutically acceptable salt thereof
wherein:
$R_{10}$ is $C_{1-3}$ alkyl optionally substituted with —OH, or $C_{2-6}$alkenyl;
$R^3$ is $C_{1-4}$ alkyl optionally substituted with —OH, or $C_{2-6}$alkenyl;
$R^E$ is hydroxy, halo, —$NR^AR^B$, cyano, nitro, alkyl, -haloalkyl, haloalkoxy or alkoxy;
$R^4$, $R^{4'}$, $R^5$, $R^{5'}$, $R^6$, $R^{6'}$, $R^7$, $R^{7'}$, $R^8$, $R^{8'}$, $R^9$ are each independently selected from the group consisting of hydrogen, —OH, alkyl, alkoxy, —$NR^AR^B$, and halogen;
$R^A$ and $R^B$ are each independently hydrogen or alkyl; and n is 0, 1, or 2.

In embodiments of the compounds of the present disclosure, $R^4$, $R^{4'}$, $R^5$, $R^{5'}$, $R^6$, $R^{6'}$, $R^7$, $R^{7'}$, $R^8$, and $R^{8'}$ are hydrogen.

In embodiments, $R^4$, $R^{4'}$ are hydrogen. In embodiments, $R^5$, $R^{5'}$ are hydrogen. In embodiments, $R^6$, $R^{6'}$ are hydrogen. In embodiments, $R^7$, $R^{7'}$ are hydrogen. In embodiments, $R^8$, and $R^{8'}$.

In embodiments, $R^4$, $R^{4'}$ $R^5$, $R^{5'}$, $R^6$, $R^{6'}$, $R^7$, $R^{7'}$, $R^8$, and $R^{8'}$ are hydrogen and $R^9$ is $C_{1-6}$ alkyl.

In embodiments e, $R^4$, $R^{4'}$ $R^5$, $R^{5'}$, $R^6$, $R^{6'}$, $R^7$, $R^{7'}$, $R^8$, and $R^{8'}$ are hydrogen and $R^9$ is —$CH_2CH_3$.

In embodiments, $R_{10}$ is $CH_3$, $R_{10}$ is —$CH_2CH_3$, —$CH_2CH_2CH_3$, —$CH=CH_2$, or —$CH_2OH$.

In embodiments, R³ is —CH₂CH₃, —CH₂CH₂CH₃, —CH₂CH₂CH₂CH₃, —CH₂—CH=CH₂, or —CH₂CH₂—OH.

In embodiments of the methods of the present disclosure, one or more compounds selected from Table 1 or 2 is administered to a subject in need thereof.

In embodiments of the methods of the present disclosure, one or more pharmaceutically acceptable salts of a compound selected from Table 1 or 2 is administered to a subject in need thereof.

TABLE 2

| No. | Compounds Structure |
|---|---|
| 1 | 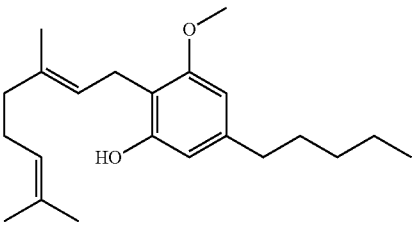 [SMILES: CCCCCc1cc(O)c(C/C=C(\C)CCC=C(C)C)c(OC)c1] |
| 2 | 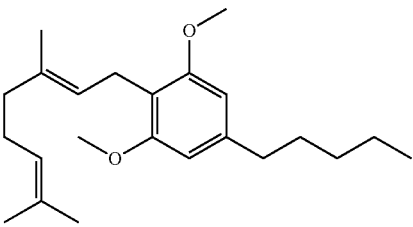 [SMILES: CCCCCc1cc(OC)c(C/C=C(\C)CCC=C(C)C)c(OC)c1] |
| 3 | 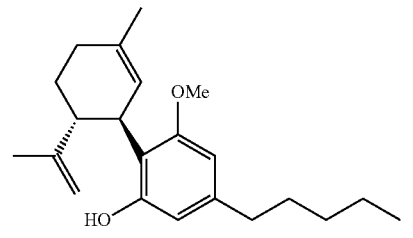 [SMILES: C=C(C)[C@@H]1CCC(C)=C[C@H]1c1c(O)cc(CCCCC)cc1OC] |
| 4 | 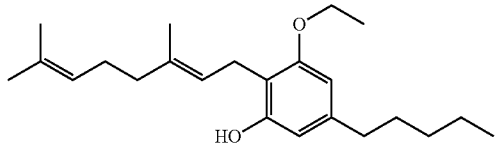 [SMILES: CCCCCc1cc(O)c(C/C=C(\C)CCC=C(C)C)c(OCC)c1] |
| 5 | 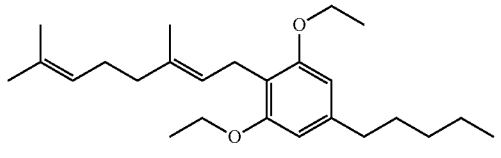 [SMILES: CCCCCc1cc(OCC)c(C/C=C(\C)CCC=C(C)C)c(OCC)c1] |
| 6 | 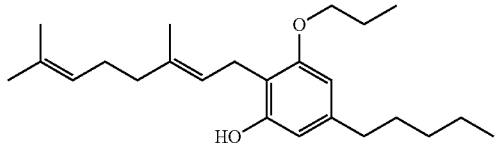 [SMILES: CCCCCc1cc(O)c(C/C=C(\C)CCC=C(C)C)c(OCCC)c1] |

TABLE 2-continued

| No. | Compounds Structure |
|---|---|
| 7 | 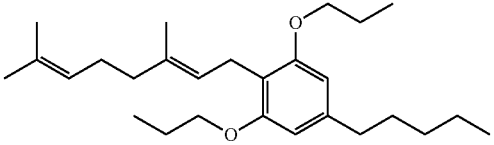 [SMILES: CCCCCc1cc(OCCC)c(C/C=C(\C)CCC=C(C)C)c(OCCC)c1] |
| 8 | 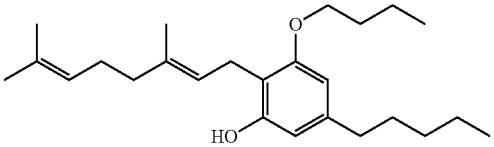 [SMILES: CCCCCc1cc(O)c(C/C=C(\C)CCC=C(C)C)c(OCCCC)c1] |
| 9 | 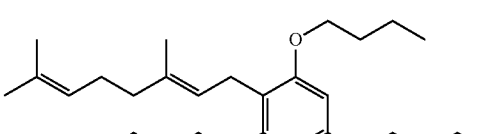 |
| 10 | 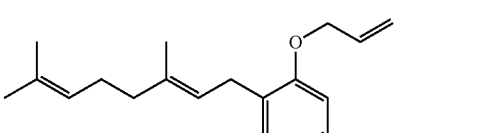 |
| 11 | 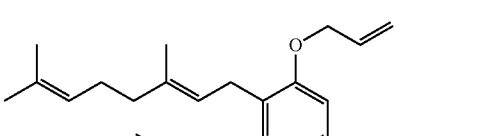 |
| 12 | 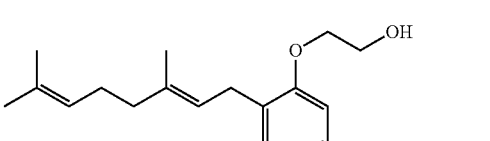 |
| 13 | 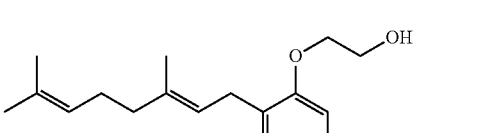 |
| 14 | 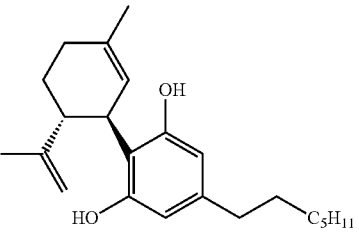 |

TABLE 2-continued

Compounds

| No. | Structure |
|---|---|
| 15 | 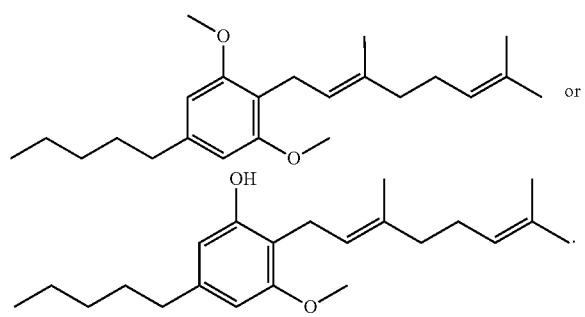 |
| 16 | 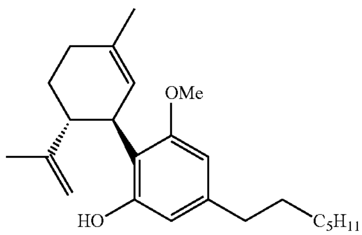 |
| 17 | |
| 18 | |
| 19 | |

In embodiments of the methods disclosed herein the compound is

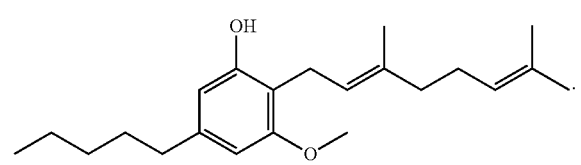 [SMILES: CCCCCc1cc(O)c(C/C=C(\C)CCC=C(C)C)c(OC)c1]

In embodiments of the methods disclosed herein, the compound is

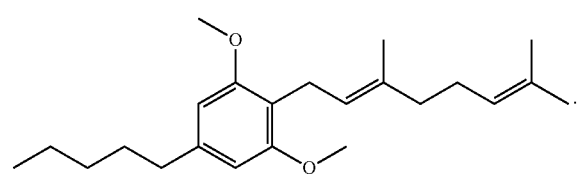 [SMILES: CCCCCc1cc(OC)c(C/C=C(\C)CCC=C(C)C)c(OC)c1]

In embodiments, the compound is

In embodiments of the methods of the present disclosure, the method comprises administering as an active agent a compound of the present disclosure (e.g., a compound of Formula (I), (II), (III), (IV), (V), Table 1 or Table 2) or a pharmaceutically acceptable salt thereof.

In embodiments of the methods of the present disclosure, the method comprises administering an effective amount of a compound consisting of a compound of the present disclosure (e.g., a compound of Formula (I), (II), (III), (IV), (V), Table 1 or Table 2) or a pharmaceutically acceptable salt thereof, and a pharmaceutically acceptable excipient or carrier. In embodiments of the methods of the present disclosure, the method comprises administering a composition consisting of a compound of the present disclosure (e.g., a compound of Formula (I), (II), (III), Table 1 or Table 2) or a pharmaceutically acceptable salt thereof, and a pharmaceutically acceptable excipient or carrier.

In embodiments of the methods of the present disclosure, the method comprises administering as an active agent a cannabinoid selected from a compound of the present disclosure (e.g., a compound of Formula (I), (II), (III), (IV), (V), Table 1 or Table 2) or a pharmaceutically acceptable salt thereof.

In embodiments, the present disclosure provides a method of treating a chronic inflammatory disease in a subject in need thereof, comprising administering a compound of the present disclosure (e.g., a compound of Formula (I), (II), (III), (IV), (V), Table 1, or Table 2) or a pharmaceutically acceptable salt thereof.

In embodiments, the present disclosure provides a method of treating pain in a subject in need thereof, comprising administering a compound of the present disclosure (e.g., a compound of Formula (I), (II), (III), (IV), (V), Table 1, or Table 2), or a pharmaceutically acceptable salt thereof.

In embodiments, the present disclosure provides a method of treating colon cancer in a subject in need thereof, comprising administering a compound of the present disclosure (e.g., a compound of Formula (I), (II), (III), (IV), (V), Table 1, or Table 2), or a pharmaceutically acceptable salt thereof.

In embodiments, the present disclosure provides a method of treating a mental health disorder in a subject in need thereof, comprising administering a compound of the present disclosure (e.g., a compound of Formula (I), (II), (III), (IV), (V), Table 1, or Table 2), or a pharmaceutically acceptable salt thereof.

In embodiments, the present disclosure provides a method of treating neurodegeneration in a subject in need thereof, comprising administering a compound of the present disclosure (e.g., a compound of Formula (I), (II), (III), (IV), (V), Table 1, or Table 2), or a pharmaceutically acceptable salt thereof. In some embodiments, methods of treating neurodegeneration in a subject with amyotrophic lateral sclerosis (ALS) is provided.

In embodiments, the mental health disorder is anxiety.

In embodiments, the mental health disorder is schizophrenia.

In embodiments, the present disclosure provides a method of treating epilepsy in a subject in need thereof, comprising administering a compound of the present disclosure (e.g., a compound of Formula (I), (II), (III), Table 1, (IV), (V), or Table 2), or a pharmaceutically acceptable salt thereof. Types of epilepsy can include, but are not limited to Angelman Syndrome, Lennox Gaustaux, Dravet, Tuberous sclerosis, Landau Kleffner, Otahara, or West's disease.

In embodiments, the present disclosure provides a method of treating seizure (e.g., seizures as disclosed herein) in a subject in need thereof, comprising administering a compound of the present disclosure (e.g., a compound of Formula (I), (II), (III), (IV), (V), Table 1, or Table 2), or a pharmaceutically acceptable salt thereof. Seizures as described herein can include epileptic seizures (e.g., as disclosed herein).

In embodiments, the compounds of the present disclosure are used for treating a chronic inflammatory disease in a subject in need thereof, comprising administering a compound of the present disclosure (e.g., a compound of Formula (I), (II), (III), (IV), (V), Table 1, or Table 2), or a pharmaceutical composition comprising a compound of the present disclosure (e.g., a compound of Formula (I), (II), (III), (IV), (V), Table 1, or Table 2).

In embodiments, the disease is an inflammatory bowel disease (IBD).

In embodiments, the inflammatory bowel disease is Crohn's disease.

In embodiments, the inflammatory bowel disease is ulcerative colitis.

In embodiments of any one of the methods described herein, the subject is human.

Compounds of the present disclosure can be formulated as a pharmaceutical composition. In embodiments, such a pharmaceutical composition comprises a compound of the present disclosure (e.g., a compound of Formula (I), (II), (III), (IV), (V), Table 1, or Table 2)) or a pharmaceutically acceptable salt thereof. In embodiments, the composition further comprises a pharmaceutically acceptable carrier.

In embodiments of the present disclosure, a pharmaceutical composition comprising one or more compounds of the present disclosure (e.g., a compound of Formula (I), (II), (III), (IV), (V), Table 1, or Table 2) or a pharmaceutically acceptable salt thereof, and a pharmaceutically acceptable excipient or adjuvant is provided. The pharmaceutically acceptable excipients and adjuvants are added to the composition or formulation for a variety of purposes. In embodiments, a pharmaceutical composition comprising one or more compounds disclosed herein, or a pharmaceutically acceptable salt thereof, further comprise a pharmaceutically acceptable carrier. In embodiments, a pharmaceutically acceptable carrier includes a pharmaceutically acceptable excipient, binder, and/or diluent. In embodiments, suitable pharmaceutically acceptable carriers include, but are not limited to, inert solid fillers or diluents and sterile aqueous or organic solutions. In embodiments, suitable pharmaceutically acceptable excipients include, but are not limited to, water, salt solutions, alcohol, polyethylene glycols, gelatin, lactose, amylase, magnesium stearate, talc, silicic acid, viscous paraffin, and the like.

In embodiments, the compositions of the present disclosure can provide therapeutic concentrations of a compound of the present disclosure (e.g., a compound of Formula (I), (II), (III), (IV), (V), Table 1, or Table 2) upon administration to a subject.

For the purposes of this disclosure, the compounds of the present disclosure can be formulated for administration by a variety of means including orally, parenterally, by inhalation spray, topically, or rectally in formulations containing pharmaceutically acceptable carriers, adjuvants and vehicles. The term parenteral as used here includes subcutaneous, intramuscular, and intraarterial injections with a variety of infusion techniques. In embodiments, the compounds of the present disclosure can be formulated for intraperitoneal administration. Intraarterial and intravenous injection as used herein includes administration through catheters.

Generally, the compounds of the present disclosure are administered in a therapeutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

EXAMPLES

The disclosure now being generally described, it will be more readily understood by reference to the following examples which are included merely for purposes of illustration of certain aspects and embodiments of the present disclosure and are not intended to limit the invention.

The compounds of the present disclosure can be synthesized using the methods as hereinafter described below, together with synthetic methods known in the art of synthetic organic chemistry or variations thereon as appreciated by those skilled in the art.

Example 1: Synthesis of (E)-2-(3,7-dimethylocta-2, 6-dien-1-yl)-3-methoxy-5-pentylphenol 1 and (E)-dimethylocta-2,6-dien-1-yl)-1,3-dimethoxy-5-pentyl-benzene (2)

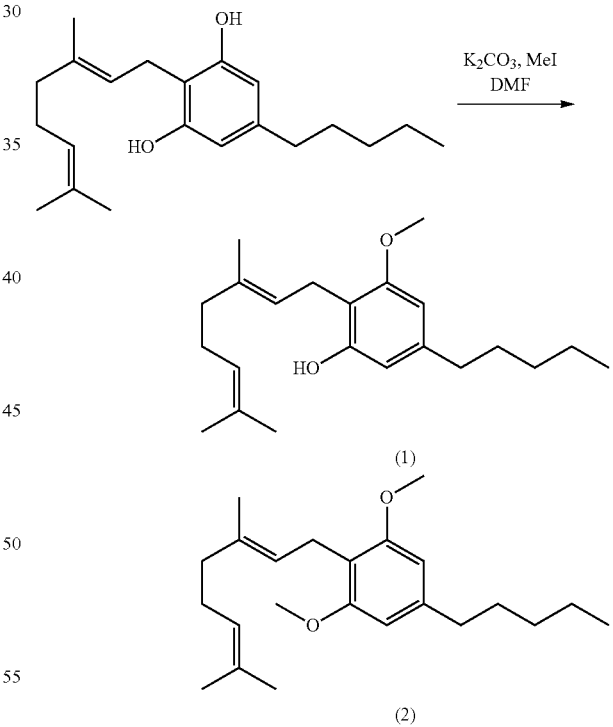

A 100 mL single neck round bottom flask was charged with cannabigerol (6.32 g; 20 mmol), DMF (50 mL), $K_2CO_3$ (5.0 g; 36.18 mmol) and were stirred at room temperature for 15 minutes. To this solution methyl iodide (2.84 g; 20 mmol) was added, the reaction mixture was stirred at room temperature for 18 hours. The reaction was monitored by LCMS and TLC (5% ethyl acetate in hexanes). LCMS shows 29% of cannabigerol, 38% of Compound 1, 32% of Compound 2. The reaction mixture was diluted with water (150 mL) and extracted with Ethyl acetate (2×100 mL). Combined organic layer was washed with brine. The organic layer was dried over Na$_2$SO$_4$ and evaporated solvent. The crude residue was chromatographed (ISCO system). Elution with 0-1% Ethyl acetate in Hexane, isolated Compound 2 (1.0 g, 14.54% yield) as colorless oil and purity>98% by LCMS and NMR. Further elution with 1-5% Ethyl acetate in Hexane, pure fractions were concentrated to obtain Compound 1 (1.5 g, 22.83% yield) as red oil and purity>98% by LCMS and NMR. Both compounds were characterized by $^1$H, $^{13}$C NMR (CDCl$_3$), and analyzed by LCMS.

Figure 2:
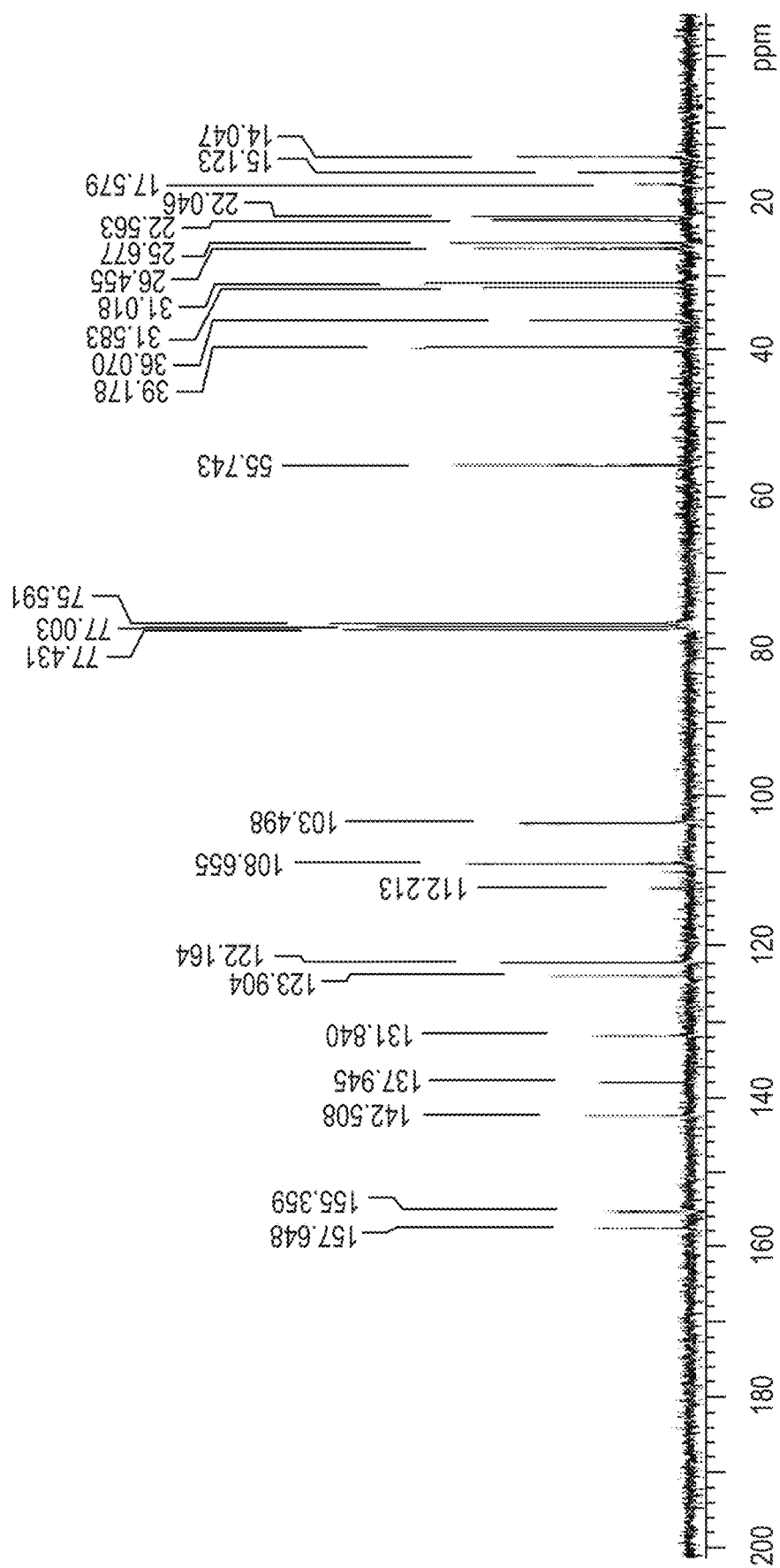
FIG. 2 shows a $^{13}$C NMR (CDCl$_3$) spectrum of Compound 1.

Compound 1: ESI LCMS [M+H]$^+$ C$_{22}$H$^{34}$O$_2$ calculated 331.26, found 331.90. FIG. 1 shows a $^1$H NMR (CDCl$_3$) spectrum of Compound 1. FIG. 2 shows a $^{13}$C NMR (CDCl$_3$) spectrum of Compound 1. $^1$H NMR and $^{13}$C NMR spectra were obtained 25° C. on a Merc200-mercury300 spectrometer.

Figure 3:
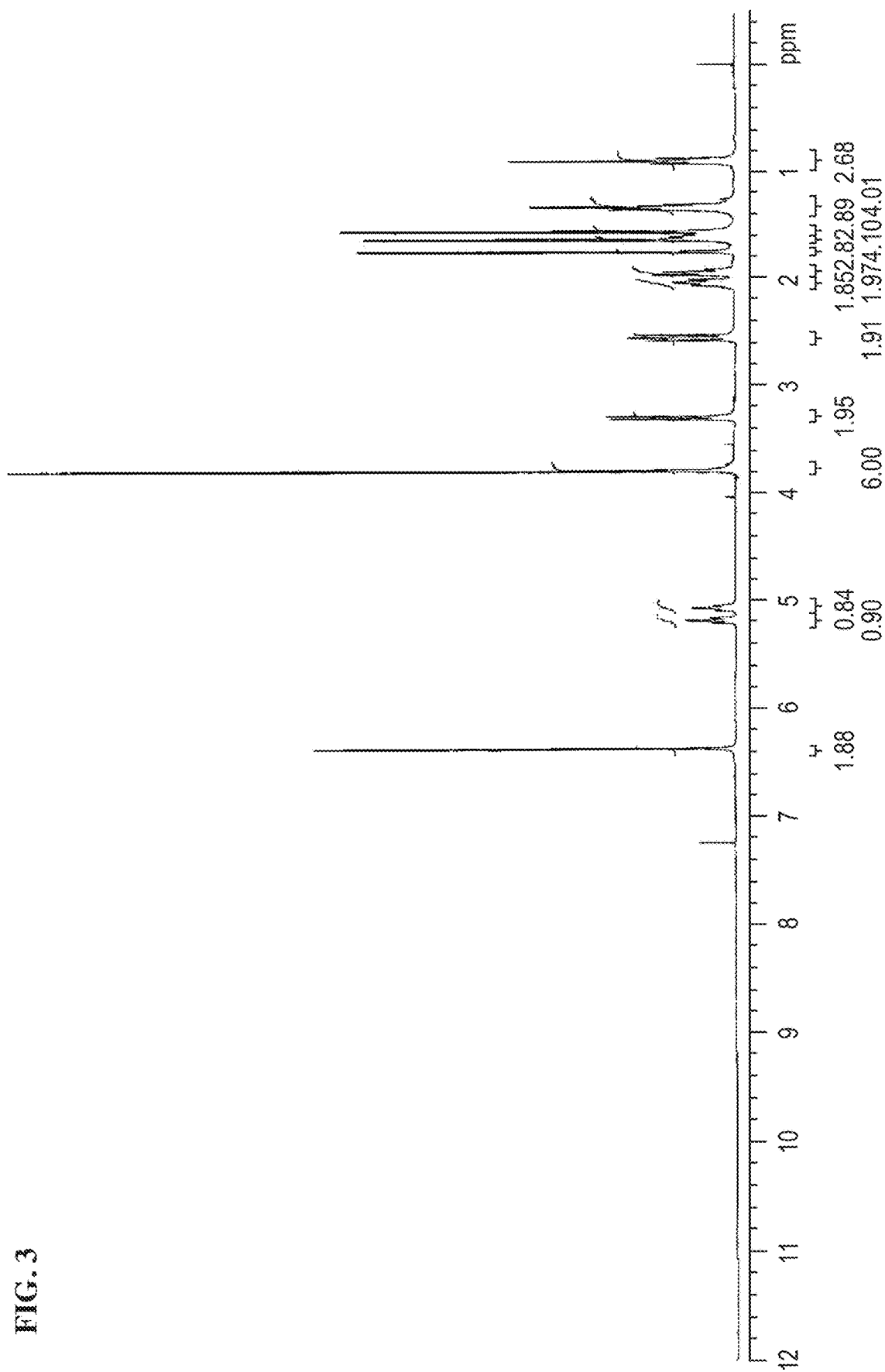
FIG. 3 shows a $^1$H NMR (CDCl$_3$) spectrum of Compound 2.
Figure 4:
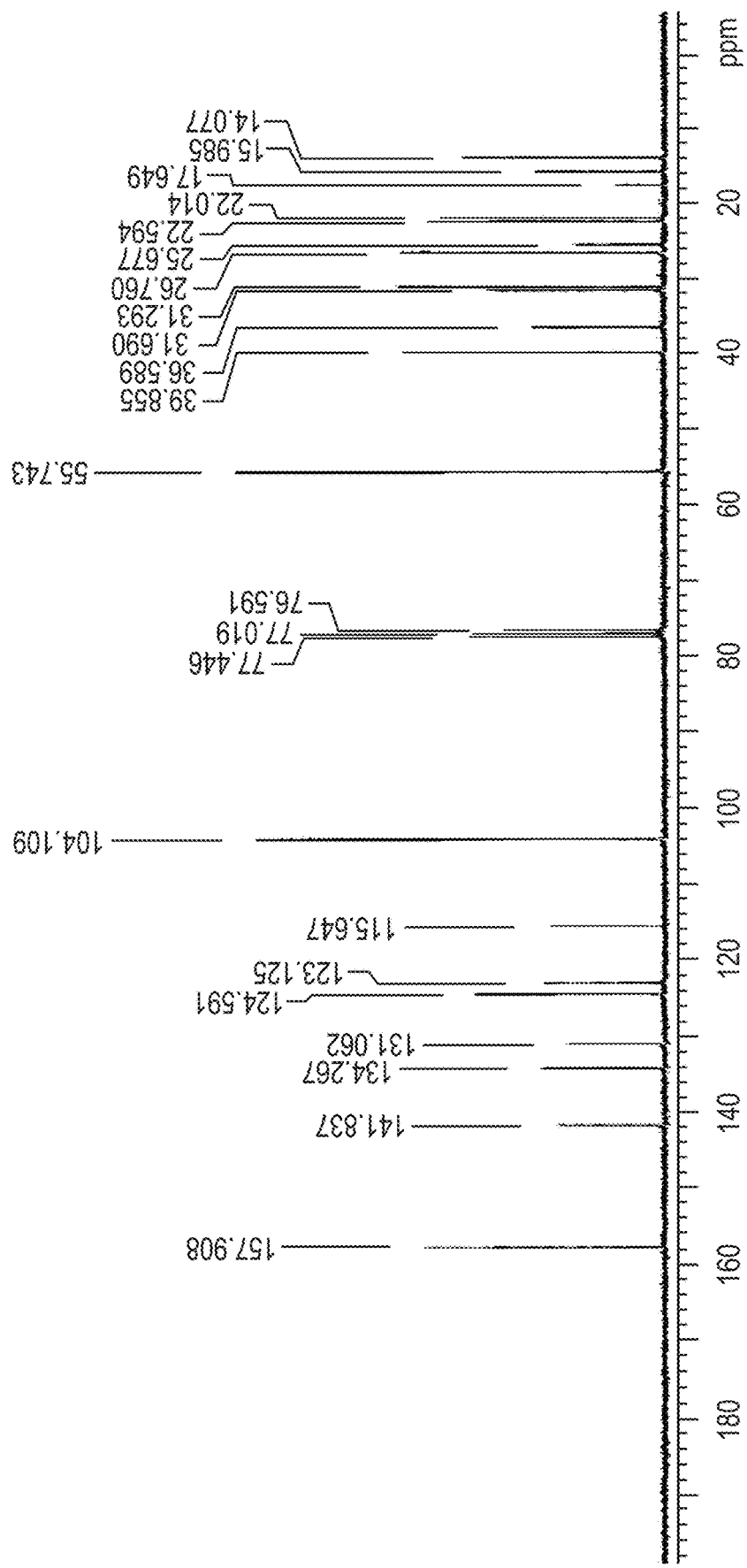
FIG. 4 shows a $^{13}$C NMR (CDCl$_3$) spectrum of Compound 2.
Figure 5:
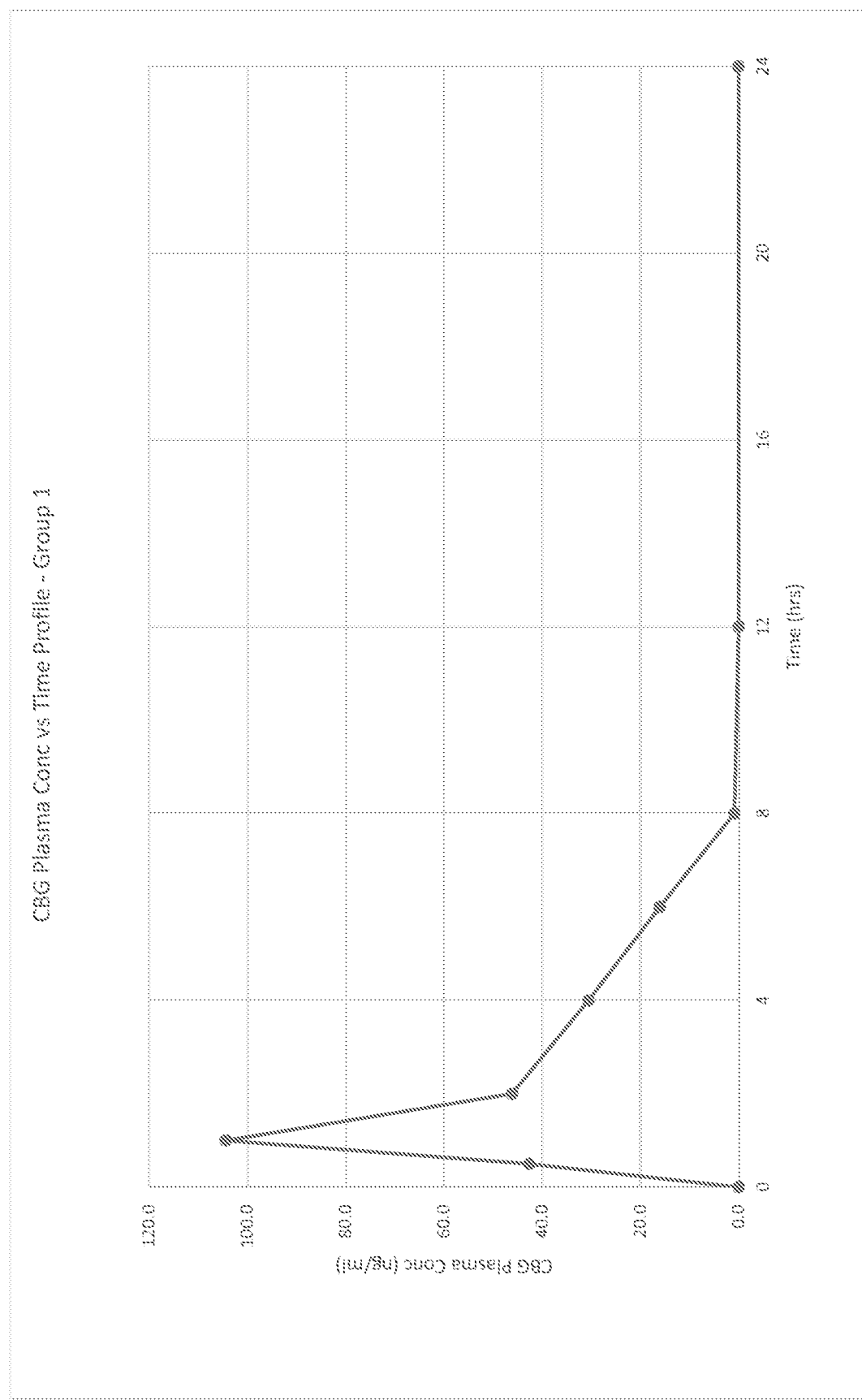
FIG. 5 is a graph showing Group 1 CBG Plasma Concentration vs Time Profile from the PK study described in Example 5.
Figure 6:
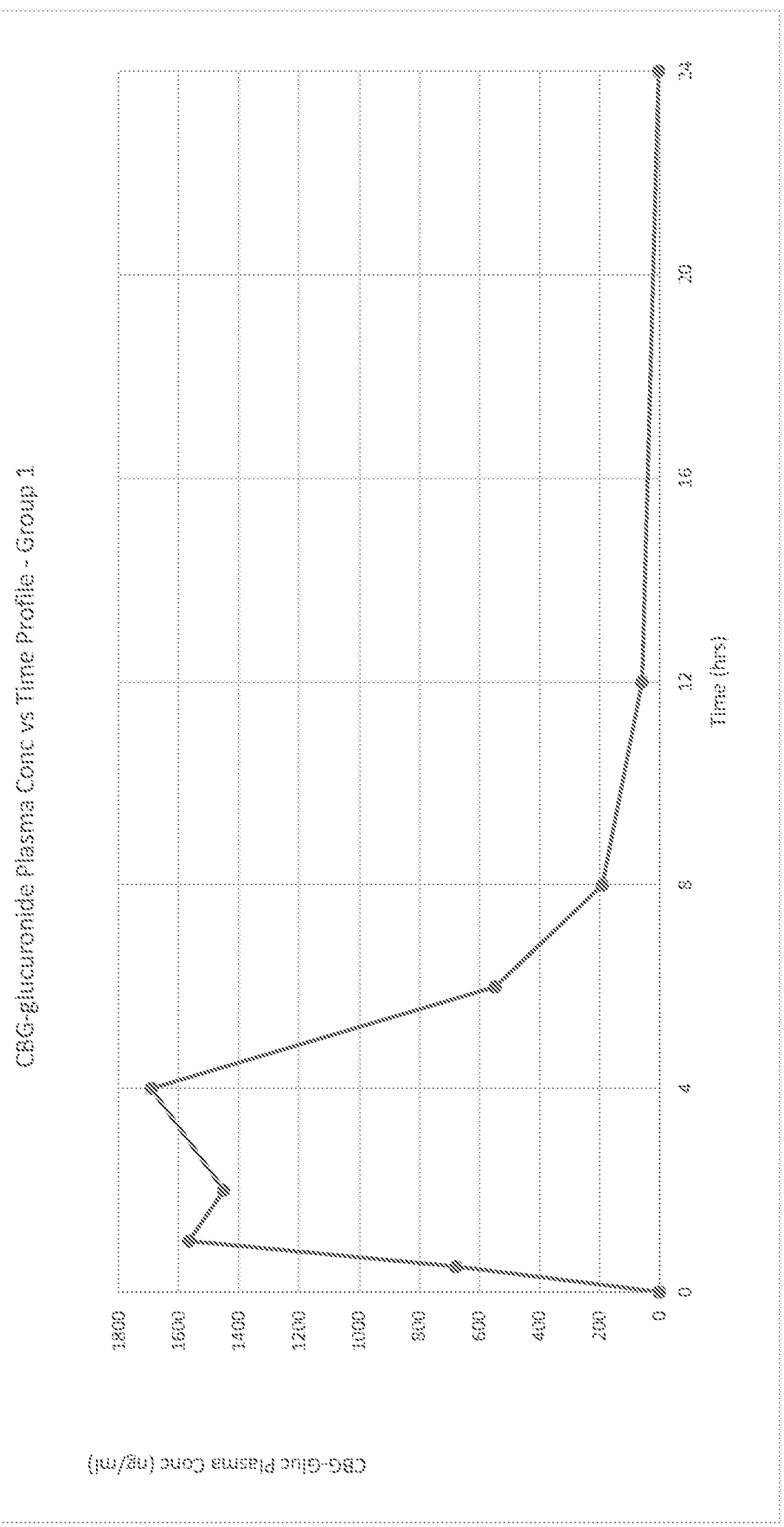
FIG. 6 is a graph showing Group 1 CBG-glucuronide Plasma Concentration vs Time Profile from the PK study described in Example 5.
Figure 7:
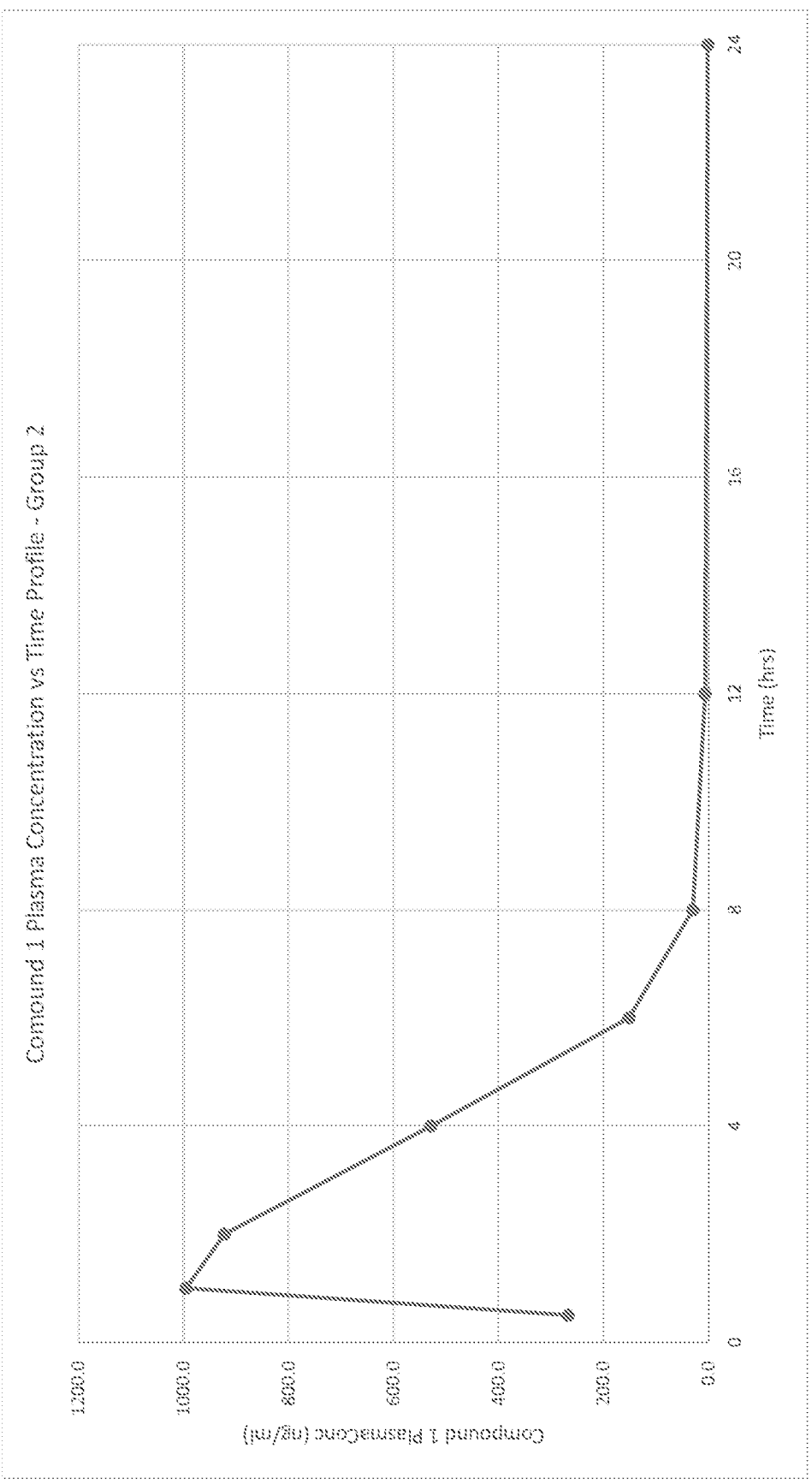
FIG. 7 is a graph showing Group 2 Compound 1 Plasma Concentration vs Time Profile from the PK study described in Example 5.
Figure 8:
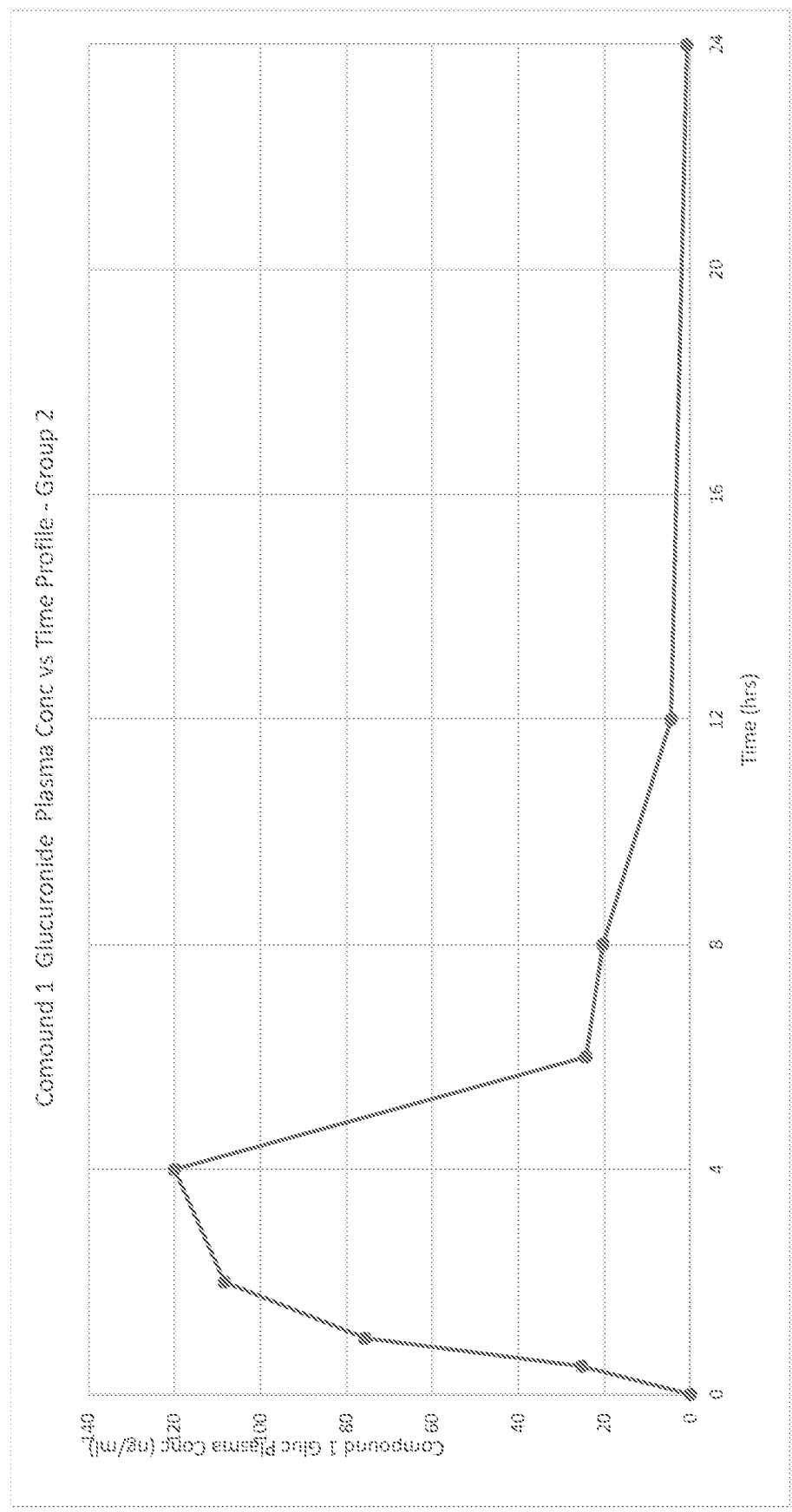
FIG. 8 is a graph showing Group 2 Compound 1 glucuronide Plasma Concentration vs Time Profile from the PK study described in Example 5.
Figure 9:
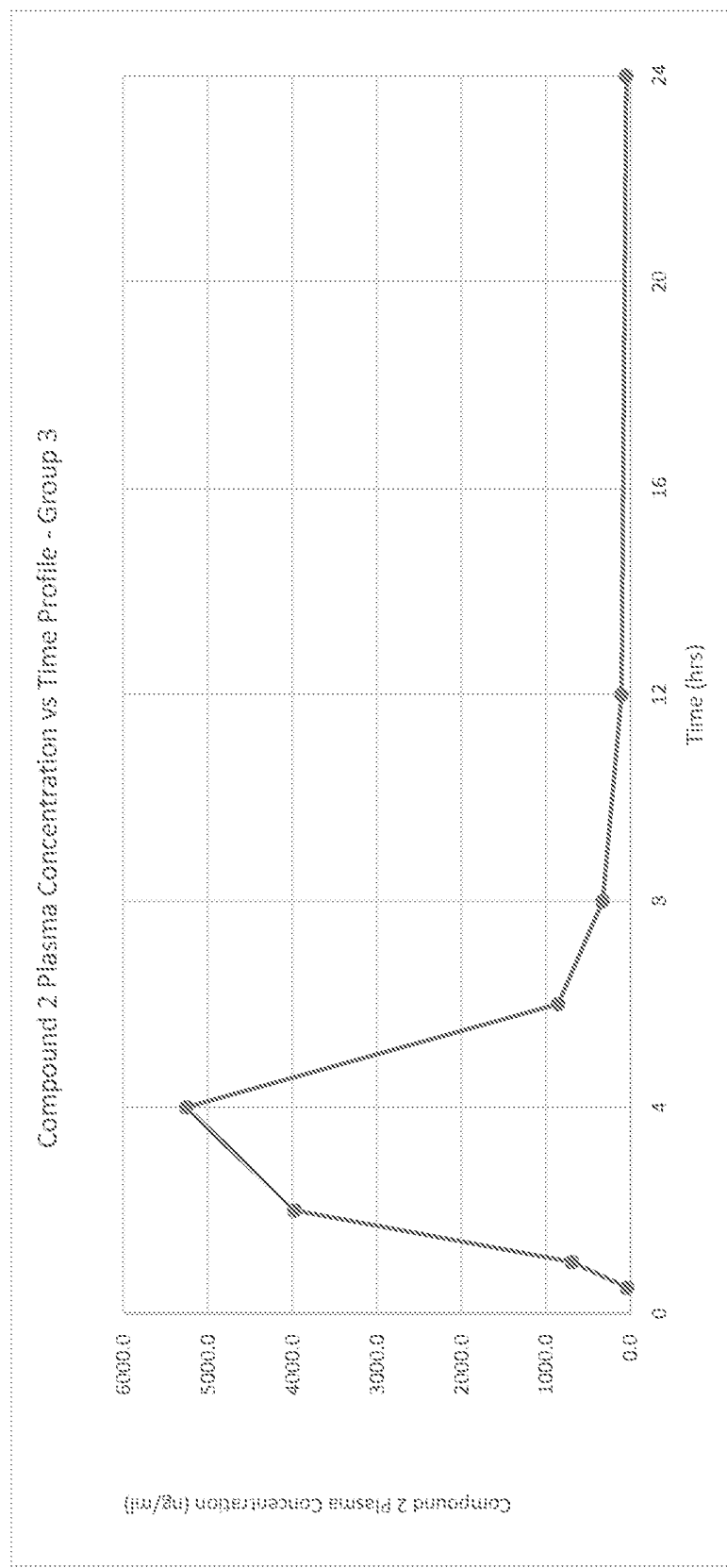
FIG. 9 is a graph showing Group 3 Compound 2 Plasma Concentration vs Time Profile from the PK study described in Example 5.
Figure 11:
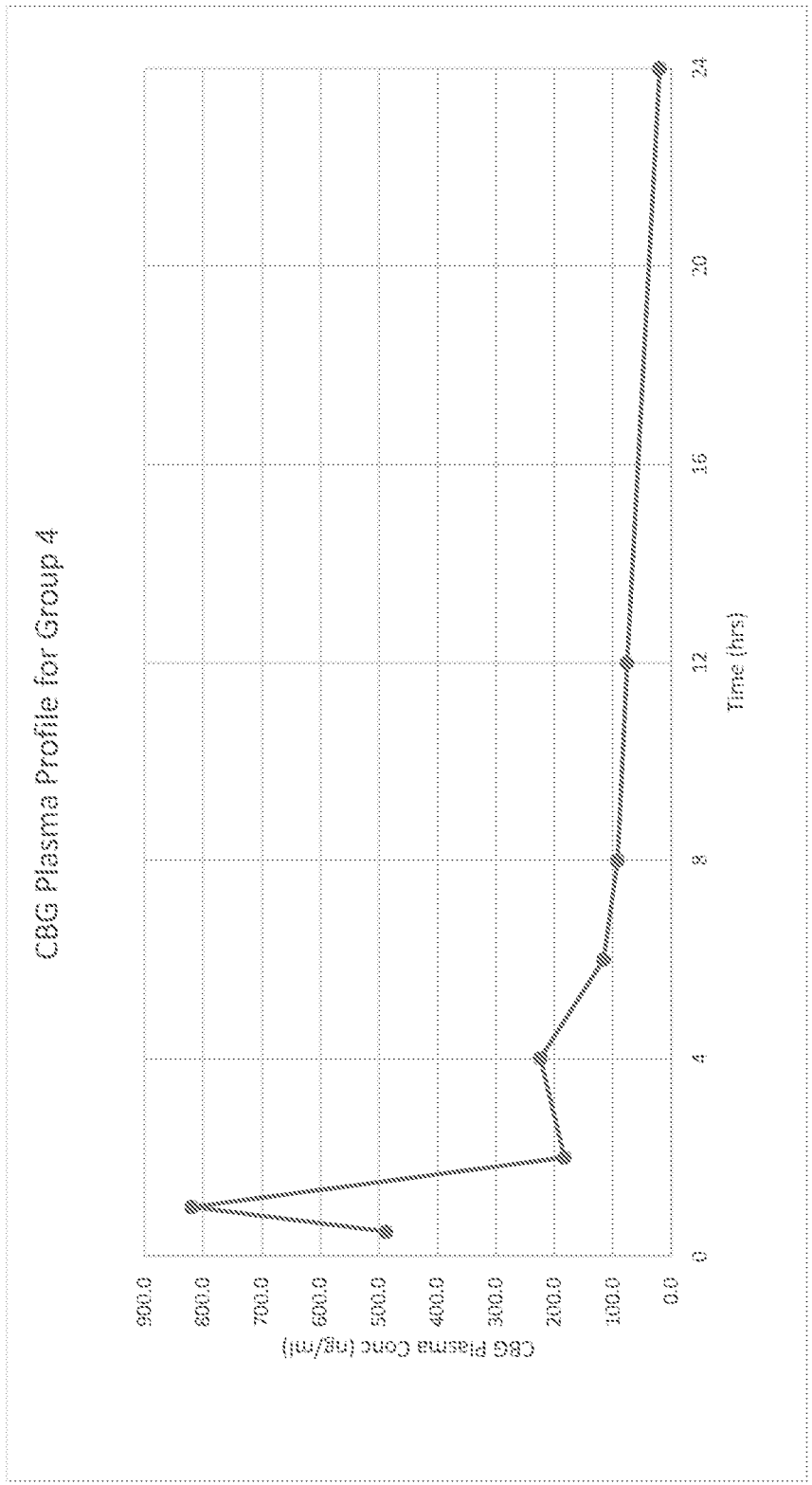
FIG. 11 is a graph showing Group 4 CBG Plasma Concentration vs Time Profile from the PK study described in Example 5.
Figure 12:
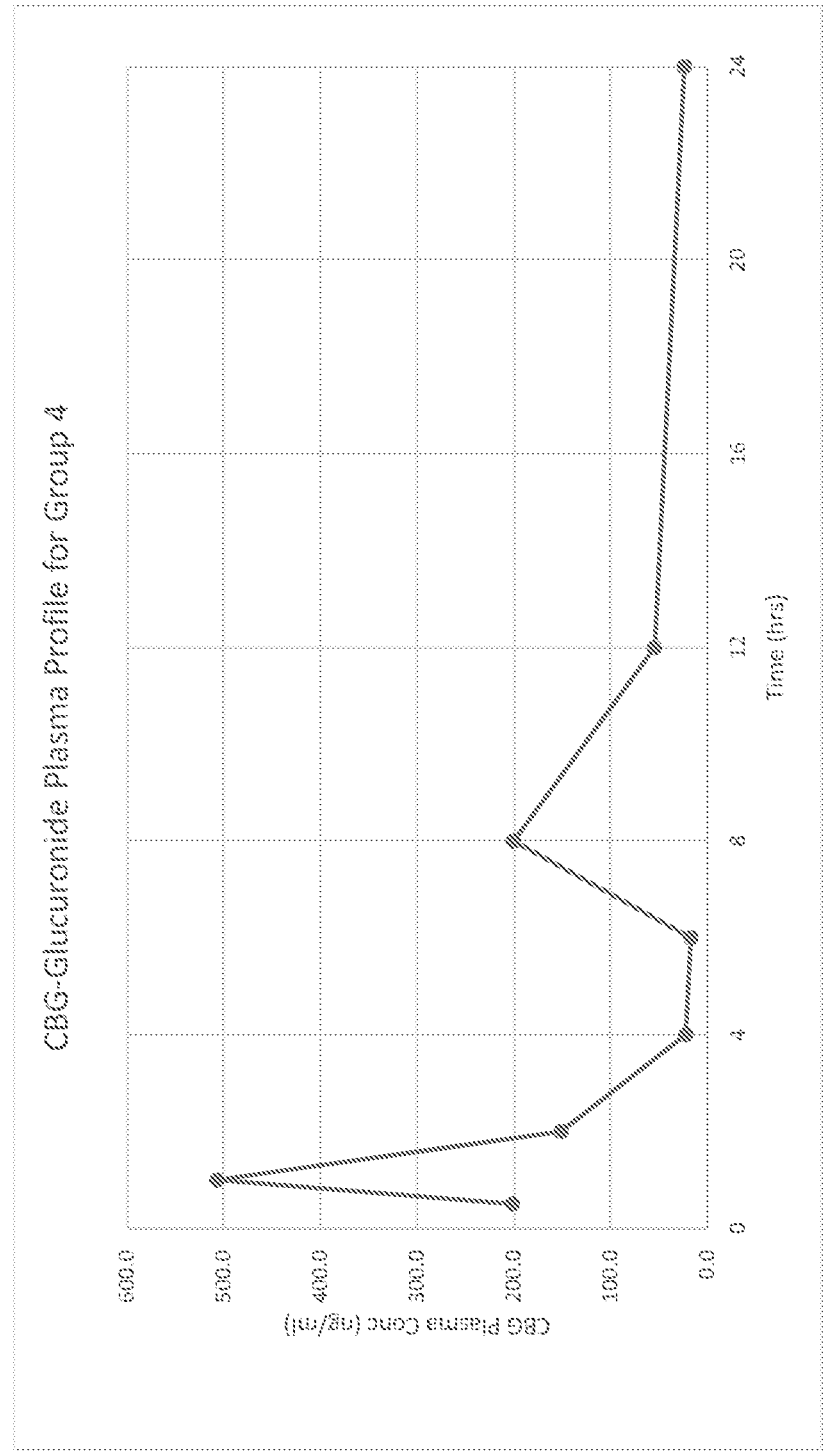
FIG. 12 is a graph showing Group 4 CBG-glucuronide Plasma Concentration vs Time Profile from the PK study described in Example 5.

Compound 2: ESI LCMS [M+H]$^+$ C$_{23}$H$_{36}$O$_2$ calculated 345.27 found 345.65 and 221.57. FIG. 3 shows a $^1$H NMR (CDCl$_3$) spectrum of Compound 2. FIG. 4 shows a $^{13}$C NMR (CDCl$_3$) spectrum of Compound 2. $^1$H NMR and $^{13}$C NMR spectra were obtained 25° C. on a Merc200-mercury300 spectrometer.

Example 2: Quantification CBG and CBG Glucuronide in Rat Plasma and Brain

The purpose of this study was to quantify cannabigerol (CBG) in rat plasma and brain.

Protocol

Seven- to nine-week-old male and female Sprague-Dawley received either a single dose or once daily dosing for 21 days of vehicle or CBG at three different dosage levels as shown in the Table below.

| Group | Test Article | Dosages (mg/kg b.w.) | Route | Frequency | Male Rat | Female Rat |
|---|---|---|---|---|---|---|
| 1. | Vehicle | 0 | Oral Gavage | Once daily | 3 | 3 |
| 2. | CBG | 10 | Oral Gavage | Once | 3 | 3 |
| 3. | CBG | 30 | Oral Gavage | Once | 3 | 3 |
| 4 | CBG | 100 | Oral Gavage | Once | 3 | 3 |
| 5. | CBG | 10 | Oral Gavage | Once daily | 3 | 3 |
| 6. | CBG | 30 | Oral Gavage | Once daily | 3 | 3 |
| 7. | CBG | 100 | Oral Gavage | Once daily | 3 | 3 |

Approximately 0.2-0.25 mL blood was collected during the first 24 hours after the single dose, and at multiple times points after the terminal dose for the animals receiving daily dosing for 21 days. Liver, kidney, and colon samples were collected and fixed in 10% NBF for 48 hours, then stored in 70% ethanol at room temperature. Brain samples were collected and flash frozen.

LC-MS Analysis

Analytical curves were constructed using non-zero standards with CBG concentration ranging from 0.0025 to 2.500 µg/mL and 2.500-100.0 µg/mL in blank rat plasma samples and 1.0 to 2500 ng/mL in blank brain tissues. A blank sample was used to exclude contamination. The linearity of the relationship between peak area ratio and concentration was demonstrated by the correlation coefficients (r=0.9970).

LC-MS/MS Conditions:

Instrument Used: AB SCIEX QTRAP 4500/Shimadzu Prominence LC

| Chromatographic Conditions | | Gradient Program | | |
|---|---|---|---|---|
| | | Time | % A | % B |
| Column: | Waters C18, 2.1 × 50 mm, 3.5 µm | 0.01 | 95 | 5 |
| Mobile Phase A: | 0.1% Formic acid in purified deionized H$_2$O | 0.50 | 95 | 5 |
| Mobile Phase B: | 0.1% Formic acid in acetonitrile | 1.00 | 5 | 95 |
| Flow Rate: | 0.4 mL/min | 3.50 | 5 | 95 |
| Injection Volume: | 10 µL | 3.60 | 95 | 5 |
| Run Time: | 5.6 min | 5.60 | 5 | 5 |

Results

The CBG and CBG glucuronide concentration in rat plasma on Day's 1 and 21 of the study is shown in Tables 1-4 below.

The concentration of CBG in plasma was shown to be low or below the level of quantitation (BLQ) (see Table 1-A and Table 2-A) and was not detected in brain (See Table 3).

CBG demonstrated very high first pass metabolism to the glucuronide upon oral administration (See Table 4 and Table 5).

TABLE 1-A

CBG concentration in rat plasma (Day 1).

| | Rat ID | | CBG concentration (ng/mL) | | | | | | |
|---|---|---|---|---|---|---|---|---|---|
| | | | 15 Min post Rx | 30 Min post Rx | 1 hr post Rx | 2 hr post Rx | 4 hr post Rx | 8 hr post Rx | 24 hr post Rx |
| Group 2 CBG 10 mg/kg | 16013777 | M | BLQ | BLQ | BLQ | 11.5 | BLQ | BLQ | BLQ |
| | 16013786 | M | BLQ | BLQ | BLQ | BLQ | BLQ | BLQ | BLQ |
| | 16013790 | M | BLQ | BLQ | 7.3 | 12.0 | BLQ | BLQ | BLQ |
| | 16013909 | F | BLQ | BLQ | 5.3 | 10.7 | BLQ | BLQ | BLQ |
| | 16013914 | F | BLQ | BLQ | BLQ | BLQ | BLQ | BLQ | BLQ |
| | 16013918 | F | BLQ | BLQ | 18.6 | 14.6 | BLQ | BLQ | BLQ |
| Group 3 CBG 30 mg/kg | 16013784 | M | 3.8 | 15.2 | 22.9 | BLQ | 24.5 | BLQ | BLQ |
| | 16013789 | M | 7.6 | BLQ | 32.3 | 11.0 | BLQ | BLQ | BLQ |
| | 16013791 | M | BLQ | BLQ | 32.5 | BLQ | BLQ | BLQ | BLQ |
| | 16013904 | F | BLQ | BLQ | 1.08 | 26.6 | 54.3 | BLQ | BLQ |
| | 16013912 | F | BLQ | BLQ | 31.2 | 78.6 | 62.1 | BLQ | BLQ |
| | 16013915 | F | BLQ | BLQ | 35.9 | 36.0 | 48.3 | BLQ | 2.75 |
| Group 4 CBG 100 mg/kg | 16013782 | M | BLQ | BLQ | BLQ | BLQ | BLQ | BLQ | BLQ |
| | 16013793 | M | BLQ | BLQ | BLQ | BLQ | BLQ | BLQ | BLQ |
| | 16013794 | M | BLQ | BLQ | BLQ | BLQ | 119.0 | BLQ | BLQ |
| | 16013907 | F | BLQ | BLQ | BLQ | BLQ | BLQ | BLQ | BLQ |
| | 16013908 | F | BLQ | BLQ | BLQ | BLQ | BLQ | BLQ | BLQ |
| | 16013913 | F | BLQ | BLQ | BLQ | BLQ | 143.0 | BLQ | BLQ |

BLQ—Below Limit of Quantification (2.5 ng/ml)

TABLE 2-A

CBG concentration in rat plasma (Day 21).

| Dose | Rat ID | | Concentration (ng/mL) | | | | | | |
|---|---|---|---|---|---|---|---|---|---|
| | | | 15 min post Rx | 30 min post Rx | 1 hr post Rx | 2 hr post Rx | 4 hr post Rx | 8 hr post Rx | 24 hr post Rx |
| Group 1 Vehicle | 16013783 | M | BLQ | | | | | | |
| | 16013792 | M | | | | | | | |
| | 16013795 | M | | | | | | | |
| | 16013902 | F | | | | | | | |
| | 16013911 | F | | | | | | | |
| | 16013917 | F | | | | | | | |
| Group 5 CBG 10 mg/kg | 16013780 | M | BLQ | BLQ | BLQ | BLQ | BLQ | BLQ | BLQ |
| | 16013785 | M | BLQ | BLQ | 1.67 | 5.6 | 4.73 | BLQ | BLQ |
| | 16013796 | M | BLQ | BLQ | BLQ | BLQ | BLQ | BLQ | BLQ |
| | 16013903 | F | BLQ | BLQ | BLQ | 9.5 | BLQ | 2.55 | BLQ |
| | 16013916 | F | BLQ | BLQ | 2.75 | 2.72 | 8.49 | BLQ | BLQ |
| | 16013919 | F | BLQ | BLQ | BLQ | BLQ | BLQ | 4.18 | BLQ |
| Group 6 CBG 30 mg/kg | 16013776 | M | BLQ | BLQ | BLQ | BLQ | BLQ | BLQ | BLQ |
| | 16013778 | M | BLQ | BLQ | BLQ | BLQ | BLQ | BLQ | BLQ |
| | 16013779 | M | 14.7 | BLQ | BLQ | BLQ | BLQ | BLQ | BLQ |
| | 16013799 | F | BLQ | BLQ | BLQ | BLQ | BLQ | BLQ | BLQ |
| | 16013901 | F | 4.51 | BLQ | BLQ | BLQ | BLQ | BLQ | BLQ |
| | 16013906 | F | 9.12 | BLQ | BLQ | BLQ | BLQ | BLQ | BLQ |
| Group 7 CBG 100 mg/kg | 16013781 | M | BLQ | BLQ | BLQ | 307.0 | BLQ | BLQ | BLQ |
| | 16013787 | M | BLQ | BLQ | BLQ | 201.0 | 171.0 | BLQ | BLQ |
| | 16013788 | M | BLQ | BLQ | BLQ | 278.0 | 129.5 | 215.0 | BLQ |
| | 16013798 | F | BLQ | 178.5 | 225.5 | BLQ | 185.0 | 905.0 | BLQ |
| | 16013900 | F | BLQ | 122.5 | 206.0 | 275.5 | 905.0 | 3095.0 | BLQ |
| | 16013910 | F | 41.6 | BLQ | BLQ | BLQ | 417.0 | 373.0 | BLQ |

BLQ—Below Limit of Quantification (2.5 ng/ml)

TABLE 3

CBG concentration in rat brain tissue (Day 21).

| Dose | Rat ID | | 24 hrs post Rx | Average |
|---|---|---|---|---|
| Group 1 Vehicle | 16013783 | M | BLQ | NA |
| | 16013792 | M | BLQ | |
| | 16013795 | M | BLQ | |
| | 16013902 | F | BLQ | NA |
| | 16013911 | F | BLQ | |
| | 16013917 | F | BLQ | |
| Group 5 CBG 10 mg/kg | 16013780 | M | BLQ | NA |
| | 16013785 | M | BLQ | |
| | 16013796 | M | BLQ | |
| | 16013903 | F | BLQ | NA |
| | 16013916 | F | BLQ | |
| | 16013919 | F | BLQ | |
| Group 6 CBG 30 mg/kg | 16013776 | M | BLQ | NA |
| | 16013778 | M | BLQ | |
| | 16013779 | M | BLQ | |
| | 16013799 | F | BLQ | NA |
| | 16013901 | F | BLQ | |
| | 16013906 | F | 43.8 | |
| Group 7 CBG 100 mg/kg | 16013781 | M | 53.0 | 540.33 |
| | 16013787 | M | 108.0 | |
| | 16013788 | M | 1460.0 | |
| | 16013798 | F | 271.0 | 299.27 |
| | 16013900 | F | 580.0 | |
| | 16013910 | F | 46.8 | |

BLQ—Below Limit of Quantification (1.0 ng/g)
NA—Not applicable

TABLE 4

CBG glucuronide concentration (expressed as CBG equivalents) in rat plasma (Day 1).

| Dose | Rat ID | | Concentration (ng/mL) | | | | | | |
|---|---|---|---|---|---|---|---|---|---|
| | | | 15 Min post Rx | 30 Min post Rx | 1 hr post Rx | 2 hr post Rx | 4 hr post Rx | 8 hr post Rx | 24 hr post Rx |
| Group 2 CBG 10 mg/kg | 16013777 | M | 8150 | 11400 | 19860 | 43550 | 36500 | 20000 | 123 |
| | 16013786 | M | 1320 | 22110 | 24420 | 35050 | 59500 | 32800 | 171 |
| | 16013790 | M | 3220 | 7860 | 34500 | 80500 | 24650 | 15260 | 701 |
| | 16013909 | F | 4410 | 15330 | 31800 | 35850 | 21700 | 6580 | 594 |
| | 16013914 | F | 747 | 33900 | 55500 | 49600 | 63000 | 28400 | 316 |
| | 16013918 | F | 2210 | 36600 | 65600 | 67700 | 55500 | 28000 | 200 |

TABLE 4-continued

CBG glucuronide concentration (expressed as CBG equivalents) in rat plasma (Day 1).

| | | | Concentration (ng/mL) | | | | | | |
|---|---|---|---|---|---|---|---|---|---|
| Dose | Rat ID | | 15 Min post Rx | 30 Min post Rx | 1 hr post Rx | 2 hr post Rx | 4 hr post Rx | 8 hr post Rx | 24 hr post Rx |
| Group 3 CBG 30 mg/kg | 16013784 | M | 38950 | 138000 | 150000 | 124000 | 150000 | 124000 | 2600 |
| | 16013789 | M | 49450 | 78800 | 34400 | 116000 | 34400 | 116000 | 748 |
| | 16013791 | M | 78000 | 158000 | 54800 | 106000 | 54800 | 106000 | 1050 |
| | 16013904 | F | 38950 | 112000 | 429000 | 132000 | 429000 | 132000 | 1080 |
| | 16013912 | F | 82000 | 193000 | 349000 | 92800 | 349000 | 92800 | 1540 |
| | 16013915 | F | 2090 | 129000 | 226000 | 101000 | 226000 | 101000 | 595 |
| Group 4 CBG 100 mg/kg | 16013782 | M | 90700 | 407000 | 949000 | 1570000 | 1880000 | 219000 | 2240 |
| | 16013793 | M | 27700 | 443000 | 745000 | 2080000 | 1870000 | 215000 | 11140 |
| | 16013794 | M | 64100 | 173000 | 102000 | 605000 | 1000000 | 282000 | 23600 |
| | 16013907 | F | 100000 | 436000 | 1400000 | 66700 | 953000 | 9570000 | 81000 |
| | 16013908 | F | 91900 | 482000 | 840000 | 83000 | 5700000 | 12800000 | 47350 |
| | 16013913 | F | 14900 | 428000 | 2000000 | 7560000 | 10600000 | 2265000 | 10300 |

TABLE 5

CBG glucuronide concentration (expressed as CBG equivalents) in rat plasma (Day 21).

| | | | Concentration (µg/mL) | | | | | | |
|---|---|---|---|---|---|---|---|---|---|
| Dose | Rat ID | | 15 min post Rx | 30 min post Rx | 1 hr post Rx | 2 hr post Rx | 4 hr post Rx | 8 hr post Rx | 24 hr post Rx |
| Group 1 Vehicle | 16013783 | M | | | | BLQ | | | |
| | 16013792 | M | | | | | | | |
| | 16013795 | M | | | | | | | |
| | 16013902 | F | | | | | | | |
| | 16013911 | F | | | | | | | |
| | 16013917 | F | | | | | | | |
| Group 5 CBG 10 mg/kg | 16013780 | M | 3.07 | 6.12 | 5.67 | 8.34 | 23.40 | 15.10 | 0.08 |
| | 16013785 | M | 3.83 | 14.90 | 21.50 | 30.20 | 45.30 | 5.53 | 0.02 |
| | 16013796 | M | 6.11 | 9.34 | 22.40 | 30.50 | 42.10 | 17.60 | 0.04 |
| | 16013903 | F | 7.51 | 55.50 | 25.30 | 50.40 | 79.20 | 28.10 | 0.12 |
| | 16013916 | F | 8.39 | 22.50 | 32.90 | 56.80 | 66.50 | 63.50 | 0.12 |
| | 16013919 | F | 8.58 | 29.20 | 10.10 | 5.80 | 11.10 | 23.20 | 0.09 |
| Group 6 CBG 30 mg/kg | 16013776 | M | 17.30 | 20.80 | 37.65 | 38.90 | 70.50 | 46.75 | 0.52 |
| | 16013778 | M | 22.90 | 37.35 | 58.50 | 79.50 | 32.95 | 24.10 | 0.28 |
| | 16013779 | M | NS | 42.35 | 42.60 | 89.50 | 96.50 | 43.55 | 0.28 |
| | 16013799 | F | 20.20 | 38.25 | 24.10 | 44.10 | 94.00 | 18.60 | 0.30 |
| | 16013901 | F | 33.30 | 56.50 | 52.50 | 37.05 | 69.00 | 35.90 | 1.06 |
| | 16013906 | F | 49.80 | 82.00 | 70.00 | 115.50 | 188.50 | 92.50 | 4.98 |
| Group 7 CBG 100 mg/kg | 16013781 | M | 25.40 | 119.50 | 246.50 | 795.00 | 46.70 | 119.00 | 2.20 |
| | 16013787 | M | 20.70 | 80.50 | 178.00 | 241.50 | 390.00 | 141.00 | 2.44 |
| | 16013788 | M | 29.70 | 119.50 | 142.50 | 570.00 | 1240.00 | 185.50 | 3.62 |
| | 16013798 | F | 63.10 | 216.50 | 1440.00 | 330.00 | 1425.00 | 4250.00 | 20.70 |
| | 16013900 | F | 106.00 | 463.00 | 1540.00 | 3905.00 | 5550.00 | 5550.00 | 27.00 |
| | 16013910 | F | 127.00 | 432.00 | 453.00 | 830.00 | 1970.00 | 1555.00 | 3.79 |

BLQ—Below Limit of Quantification (2.5 ng/ml)
NS—No sample

Example 3A. Metabolic Stability Study in Human Intestine Microsomes

The objective of this study was to investigate the stability of the test compound, CBG, in the presence of intestinal microsomes that only have UGT activity and no CYP activity.

Protocol

Test compound (1 µM) was incubated with pooled intestinal microsomes at 6 time points over the course of a 60 min assay and the test compound is analyzed by LC-MS/MS.

Microsomes (final protein concentration 0.5 mg/mL), alamethicin (25 µg/mg), 0.1 M Tris, 5 mM MgCl$_2$ buffer pH 7.4 and test compound (final substrate concentration 1 µM; final DMSO concentration 0.25%) were pre-incubated at 37° C. prior to the addition of UDPGA (final concentration 5 mM) to initiate the reaction. The final incubation volume is 500 µL. A *minus* cofactor control incubation was included for each compound tested where 0.1 M Tris, 5 mM MgCl2 buffer pH 7.4 is added instead of UDPGA (minus UDPGA). Two control compounds were included. All incubations were performed singularly for each test compound.

Each compound was incubated for 0, 5, 10, 20, 40 and 60 min. The control (minus UDPGA) was incubated for 60 min only. The reactions were stopped by transferring incubate into acetonitrile at the appropriate time points, in a 1:3 ratio. The termination plates were centrifuged at 3,000 rpm for 20 min at 4° C. to precipitate the protein.

Quantitative Analysis

Following protein precipitation, the sample supernatants were combined in cassettes of up to 4 compounds, internal standard was added and samples analysed using Cyprotex generic LC-MS/MS conditions.

Data Analysis

From a plot of ln peak area ratio (compound peak area/internal standard peak area) against time, the gradient of the line was determined. Subsequently, half-life and intrinsic clearance were calculated using the equations below:

Elimination rate constant $(k) = (-\text{gradient})$

Half-life $(t_{1/2})(\text{min}) = \dfrac{0.693}{k}$

Intrinsic clearance $(CL_{int})(\mu L/\text{min/mg protein}) = \dfrac{V \times 0.693}{t_{1/2}}$ where $V$ = Incubation volume (µL)/Microsomal protein (mg)

Results

The parent compound CBG disappeared rapidly when incubated with human intestine microsomes (see Table 6), while CBG-glucoronide appeared rapidly when incubated with human intestine microsomes (see Table 7).

These results confirm UGT glucuronidation of CBG presents a significant barrier to oral bioavailability.

TABLE 6

Metabolic Stability Assay - profile of parent compound CBG

Metabolic Stability (ProteinType = Microsomes + Alamethicin, ProteinSource = Intestinal, Species = Human, FinalTimePoint = 60 min, Cofactor = UDPGA, BufferType = Tris, TerminationSolution = ACN + formic, HasQCs = No, TimePoints = 6)

| Compound Id | $CL_{int}$ (µL/min/mg protein) | SE $CL_{int}$ | $t_{1/2}$ (min) | n | Comments |
|---|---|---|---|---|---|
| CBG | 884 | 0 | 1.57 | 2 | Test compound not detectable by 10 minutes. CLint calculated from 0 and 5 minute time points only. 10, 20, 40, and 60 minute time points excluded. |

TABLE 7

Metabolic Stability Assay - profile of metabolite CBG glucuronide

Metabolic Stability (ProteinType = Microsomes + Alamethicin, ProteinSource = Intestinal, Species = Human, FinalTimePoint = 60 min, Cofactor = UDPGA, BufferType = Tris, TerminationSolution = ACN + formic, HasQCs = No, TimePoints = 6)

| Parent Cmpd Id | Metabolite Id | Time (min) | Metabolite Formation | | |
|---|---|---|---|---|---|
| | | | Compound Peak Area | IS Peak Area | Peak Area Ratio |
| CBG | Metabolite 1 | 0 | 46.9 | 615499 | 0.0000762 |
| | | 5 | 1415 | 628102 | 0.00225 |
| | | 10 | 1563 | 629362 | 0.00248 |
| | | 20 | 1869 | 619885 | 0.00301 |
| | | 40 | 1736 | 614702 | 0.00282 |
| | | 60 | 1389 | 561884 | 0.00247 |
| | | Control | | 587897 | |

Example 3B. Conversion of CBG and Compound 1 to Glucuronides Metabolites by Isolated UGT Isozymes The purpose of this study was determined which Isoform of UGT was the most active with CBG, and to compare and contrast that activity with Compound 1 monomethyl ether.

Experimental Summary: UGT Reaction Phenotyping (7 Isoforms).

| Test Article | Test conc. | UGT Source | Incubation Times | UGT Isozyme | Analytical Method |
|---|---|---|---|---|---|
| CBG | 5 μM | Human recombinant Supersomes | 0, 10, 20, 40, and 60 min (37° C.) | UGT1A1, UGT1A3, UGT1A4, UGT1A6, UGT1A9, UGT2B7, | LC-MS/MS |

Experimental Procedure: cDNA expressed human UGT enzyme preparations (Supersomes) supplied by BD Biosciences were obtained and stored at −80° C. prior to use. The specific isoforms were chosen by the performing laboratory based on published guidelines. They are considered the clinically relevant of the UGT isoforms (E. Kasteel et al. Human variability in isoform-specific UDP-glucuronosyltransferases: markers of acute and chronic exposure, polymorphisms and uncertainty factors. *Arch Toxicol.* 2020; 94(8): 2637-2661)

Supersomes in 0.1 M Tris buffer pH 7.4, alamethicin (44.6 μg/mL) and test compound (final concentration of 5 μM; final DMSO concentration ≤0.1%) were pre-incubated at 37° C. prior to the addition of UDGPA (final concentration 2 mM) to initiate the reaction. Incubations were also performed using control Supersomes (no UGT enzymes present) to reveal any non-enzymatic degradation. Compounds known to be metabolized specifically by each UGT isoform were used as control compounds (7-hydroxy-4-trifluoromethylcoumarin, all but UGT1A4, or trifluoperazine for UGT1A4).

CBG or Compound 1 were incubated in duplicate for 0, 10, 20, 40 and 60 min with each isoform. The reactions were stopped by the addition of methanol containing an analytical internal standard at the time points specified in the table above. Stopped reactions were kept on ice for at least ten minutes and the samples were centrifuged to remove precipitated protein. Supernatants were analyzed by LC-MS/MS methodology developed by the performing laboratory to quantitate the parent remaining.

Figure 34:
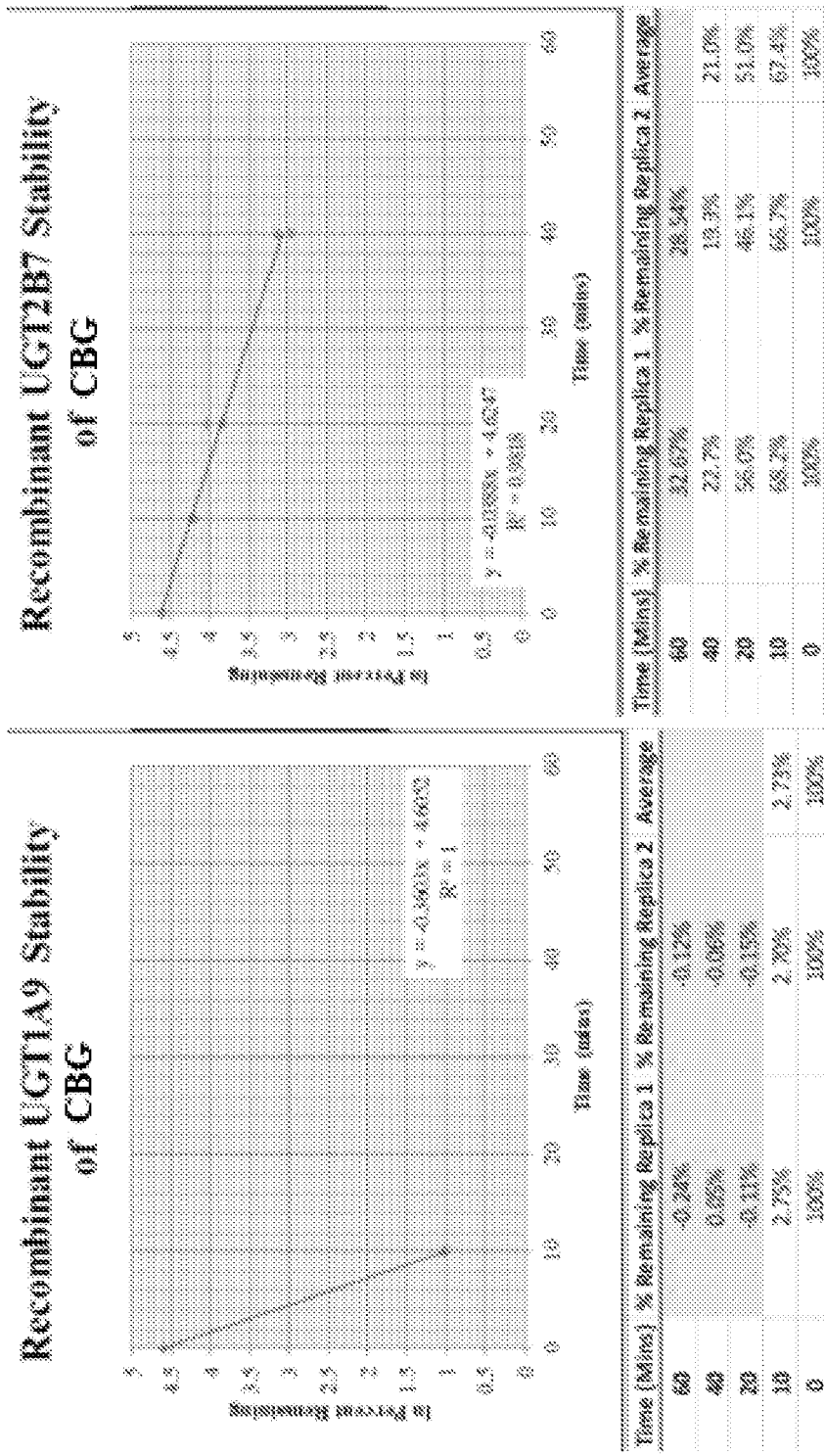
FIG. 34 is a graph depicting the stability of CBG in the presence of UGT1A9.

As examples, the data obtained with UGT1A9 and UGT2B7 are shown in FIG. 34. And FIG. 35 Plots of similar design were obtained with each Isoform and both test articles.

The change in CBG concentration were used to calculate the Half life ($t_{1/2}$ in min) and the intrinsic clearance (l/min/mg) as shown in the following table (S. C, Khojasteh et.al., *Drug Metabolism and Pharmacokinetics Quick Guide*, Springer, NY, 2011), Intrinsic Clearance ($CL_{int}$) is a measure of the ability of hepatocytes to eliminate drug irrespective other factors such as blood flow or protein binding. The calculations were the same as those used in Example 3A.

UGT Reaction Phenotyping: data summary

| | | Test Article | | |
|---|---|---|---|---|
| Reference Compound | Test Conc. | Test UGT Isoform | Recombinant UGT $CL_{INT}^{a}$ Clearance (μl/min/mg) | Recombinant UGT Half Life $T_{1/2}^{b}$ (mins) |
| Trifluoperazine | 1 μM | UGT1A4 | 0.70 | 985.85 |
| Trifluoperazine Glucuronide | 1 μM | UGT1A4 | — | *6.38 |
| 7-OH4trifluoromethylcoumarin | 1 μM | UGT1A1 | 41.84 | 33.14 |
| 7-OH4trifluoromethylcoumarin | 1 μM | UGT1A3 | 26.78 | 51.77 |
| 7-OH4trifluoromethylcoumarin | 1 μM | UGT1A6 | 216.26 | 6.41 |
| 7-OH4trifluoromethylcoumarin | 1 μM | UGT1A9 | 456.07 | 3.04 |
| 7-OH4trifluoromethylcoumarin | 1 μM | UGT2B7 | 27.49 | 50.43 |
| 7-OH4trifluoromethylcoumarin | 1 μM | UGT2B15 | 55.78 | 24.85 |
| CBG | 1 μM | UGT1A1 | 17.98 | 77.1 |
| | 1 μM | UGT1A3 | 31.43 | 44.11 |
| | 1 μM | UGT1A4 | <2.89 | >240 |
| | 1 μM | UGT1A6 | 14.59 | 95.05 |
| | 1 μM | UGT1A9 | 720.53 | 1.92 |
| | 1 μM | UGT2B7 | 77.54 | 17.88 |
| | 1 μM | UGT2B15 | 29.11 | 47.62 |
| Compound 1 | 1 μM | UGT1A1 | 13.48 | 102.8 |
| | 1 μM | UGT1A3 | 12.81 | 108.22 |
| | 1 μM | UGT1A4 | <2.89 | >240 |
| | 1 μM | UGT1A6 | <2.89 | >240 |
| | 1 μM | UGT1A9 | 99.10 | 13.99 |
| | 1 μM | UGT2B7 | 55.89 | 24.80 |
| | 1 μM | UGT2B15 | 24.24 | 57.18 |

[a]Intrinsic Clearance;
[b]Half-Life;
*average peak area ratio at 60 min/average peak area ratio at 0 min)

The enzymatic activity was as expected with the positive controls, indicating the enzymatic incubators were behaving as expected. The results demonstrate that CBG is extensively converted to the glucuronide conjugate by UGT and the highest activity was seen with isoform UGT1A9. The activity with this isoform represents close to 80% of the activity with CBG for all the UGTs combined. The second most active enzyme was UGT2B7 which was approximately ¹/₁₀ as active as UGT1A9. Both Isoforms have been shown to be present in the liver and intestine, as well as the kidney (Kassteel et. Al. 2020) In fact, some 53% of the UGT activity in the GI tract is associated with UGT2B7. These two enzymes would be responsible for most of the glucuronide formation for orally CBG.

These data are consistent with the observation that glucuronidation of CBG by the GI tract is extensive, and is primarily due to the the UGT1A9 and UGT2B7 Isofrom.

Activities were somewhat lower with Compound 1, the monomethyl congener of CBG. Total UGT activity was only 23% of that observed with CBG, but 73% of that activity was still associated with UGT1A9 and UGT2B7.

Example 3C. Potential for Compound 1 to Inhibit the Glucuronidation of CBG by Monomethyl CBG (CBG)

The purpose of this experiment was to determine if Compound 1 can inhibit the glucuronidation of CBG, as both are substrates for the two major isoforms responsible for CBG glucuronidation.

The ability of Compound 1 to inhibit the metabolism of CBG by UGT1A9 and UGT2B7 enzymes was investigated to ascertain the ICso values for direct inhibition. The incubation conditions (substrate concentration, incubation time and protein concentration) were determined in Part 2 of the protocol such that CBG metabolism remains near initial rate conditions (e.g., 20-30% substrate loss).

Preliminary experiments were conducted in Part I of the protocol, first to establish the HPLC/MS/MS bioanalytical methods for CBG and CBG glucuronide. The establishment of the method was routine and the method was shown to be working appropriately. The second set of preliminary experiments (Part 2), as mentioned, were conducted to optimize the incubation conditions as described above. Incubations (at 37 C) contained Tris-HCl buffer (100 mM, pH 7.7), MgCl2 (10 mM), EDTA (1 mM, pH 7.4) and UDP-glucuronic acid (UDPGA, 10 mM). CBG was added to each incubation in DMSO such that the final percent of DMSO was 1% v/v, or less. Reactions were terminated by the addition of an equal volume of stop reagent, acetonitrile containing an internal standard. The samples were centrifuged (e.g., 920 RCF for 10 minutes at 10° C.), and the supernatant fractions were analyzed by LC-MS/MS to determine the amount of CBG remaining and formation of one metabolite (CBG glucuronide).

Figure 37:
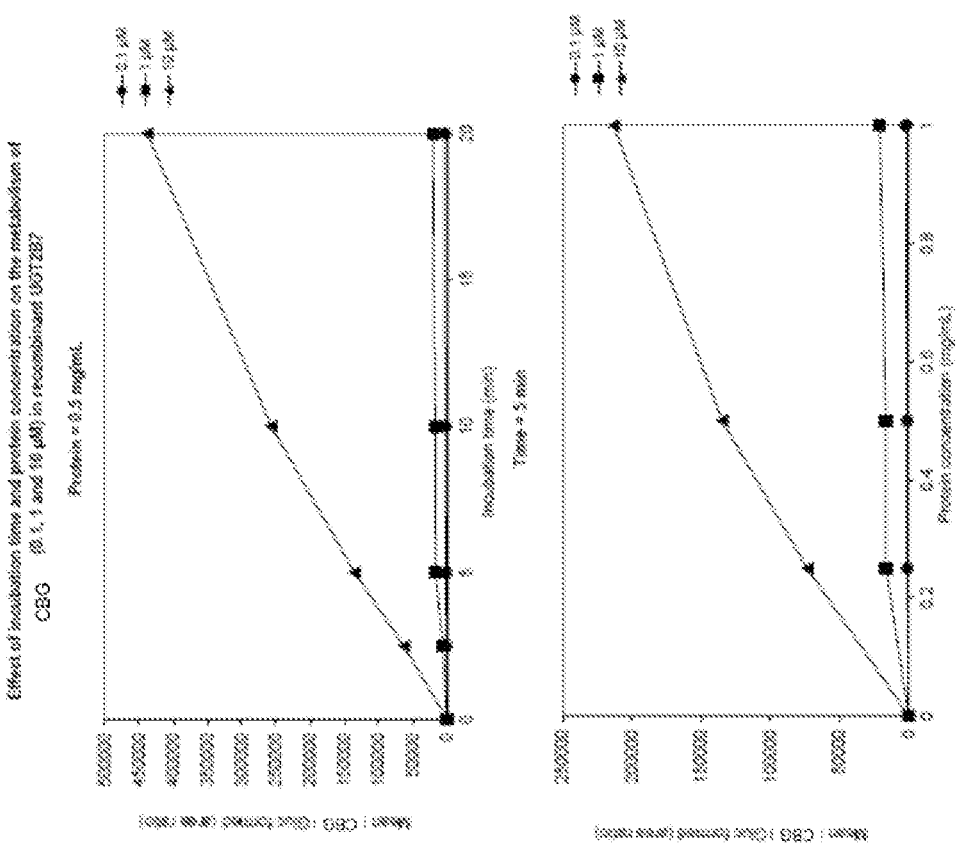
FIG. 37 is a graph showing the effect of incubation time and protein concentration on the metabolism of CBG in UGT2B7.
Figure 38:
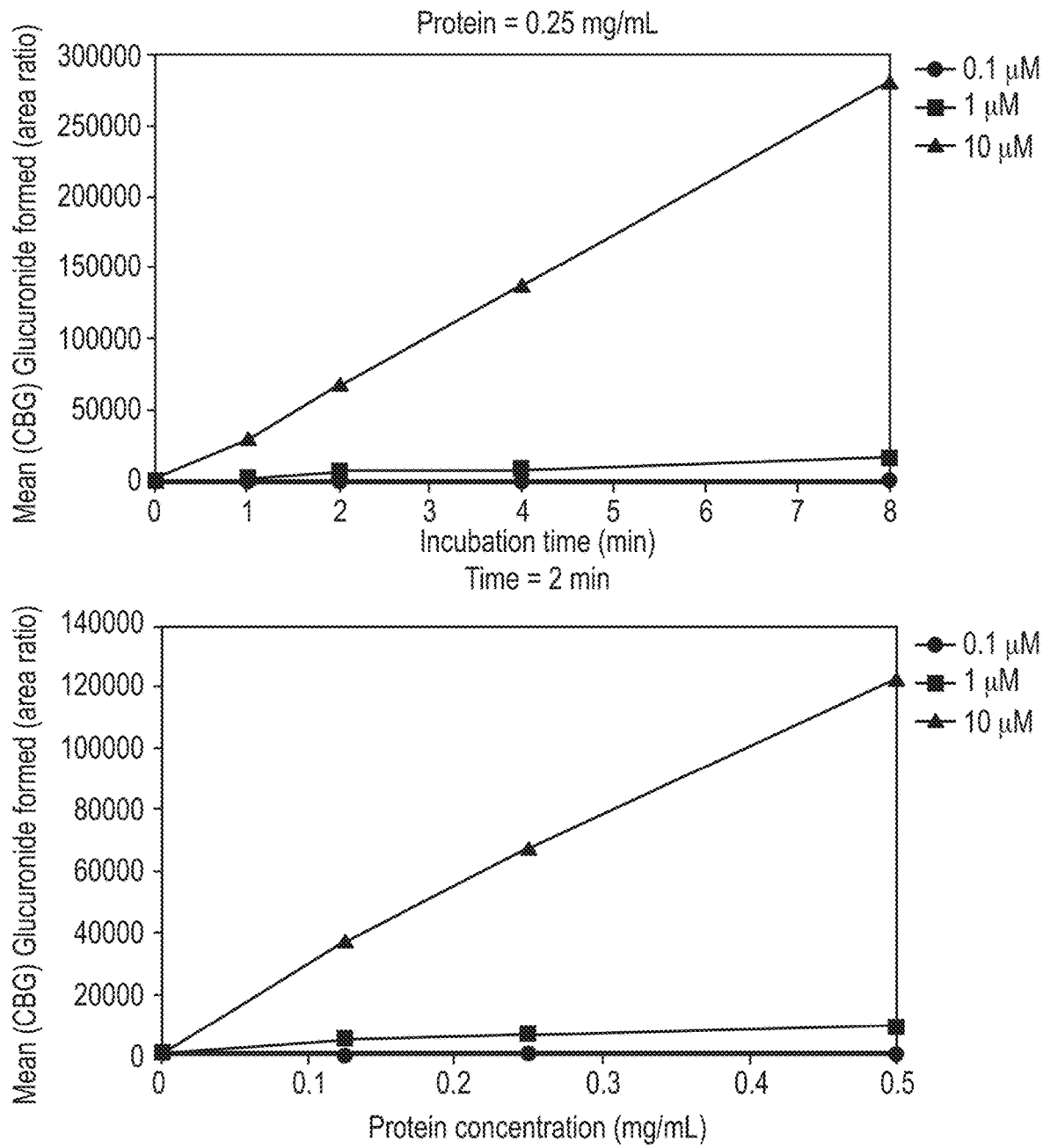
FIG. 38 is a graph showing the effect of incubation time and protein concentration on the metabolism of CBG in UGT1A9.

The results of the preliminary experiments are summarized in FIG. 37 and FIG. 38.

To examine its ability to act as a direct inhibitor of the above listed enzymes, Compound 1 was added to recombinant human UGT enzyme together with CBG. Reactions were initiated with UDPGA and were carried out in duplicate. For all assays, reactions were terminated by the addition of acetonitrile with or without 2% v/v formic acid, including the internal standard.

Authentic metabolite reference standards were used for quantitation of the probe substrate metabolites and as internal standards. Based on the information obtained in the Part 2 experiments, the following table summarizes the experiments performed, assessing the inhibitory effects of Compound 1 was conducted as follows:

| Description | Test Article | Positive control |
|---|---|---|
| Substrate | CBG | 7-hydroxycoumarin |
| Substrate Concentration | 10 µM | 1 µM |
| Inhibitor | Compound 1 | NA |
| Inhibitor Concentration (µM) | 0 (solvent control), 0.01, 0.03, 0.1, 0.3, 1, 3, 10 | NA |
| Incubation volume | 0.2-mL | |
| Incubation temperature | 37 ± 2° C. | |
| Test systems | rUGT1A9 and rUGT2B7[a] | |
| rUGT1A9 Incubation time (min) | 4 min | 0 and 60 |
| rUGT1A9 Protein/incubation | 0.25 mg protein/ml | 0.1 mg protein/mL |
| rUGT2B7 Incubation time (min) | 5 min | 0 and 60 |
| rUGT2B7 Protein/incubation | 0.25 mg protein/ml | 0.1 mg protein/mL |
| Incubation buffer | Tris-HCl buffer (100 mM, pH 7.7), MgCl$_2$ (10 mM), EDTA (1 mM, pH 7.4) | |
| Cofactor | UDPGA (10 mM) [b] | |
| Start method | Addition of co-factor | |
| Number of replicates | 2 | 2 |
| Assay determination | Substrate loss with calibration curve Formation of one metabolite (without calibration curve) | Substrate loss without calibration curve |

[a]Each test system will be incubated separately.

The results of these experiments are summarized below. The amounts of CBG present at the end of the incubation periods was determined. For inhibition to have occurred, the amounts of CBG present at the end of the incubation period needed to increase, and the amounts of glucuronide formed needed to decrease.

CBG Loss

| Test system | | CBG detected (pmol) | Percent of control |
|---|---|---|---|
| rUGT1A9 | 10 µM CBG | 1140 | 100 |
| | 10 µM CBG + 0.01 µM Compound 1 | 1250 | 109 |
| | 10 µM CBG + 0.03 µM Compound 1 | 1250 | 110 |
| | 10 µM CBG + 0.1 µM Compound 1 | 1280 | 112 |
| | 10 µM CBG + 0.3 µM Compound 1 | 1300 | 114 |
| | 10 µM CBG + 1 µM Compound 1 | 1210 | 106 |
| | 10 µM CBG + 3 µM Compound 1 | 1200 | 105 |
| | 10 µM CBG + 10 µM Compound 1 | 1140 | 99.8 |
| rUGT2B7 | 10 µM CBG | 1330 | 100 |
| | 10 µM CBG + 0.01 µM Compound 1 | 1370 | 103 |
| | 10 µM CBG + 0.03 µM Compound 1 | 1460 | 109 |
| | 10 µM CBG + 0.1 µM Compound 1 | 1410 | 106 |
| | 10 µM CBG + 0.3 µM Compound 1 | 1450 | 109 |
| | 10 µM CBG + 1 µM Compound 1 | 1460 | 109 |
| | 10 µM CBG + 3 µM Compound 1 | 1440 | 108 |
| | 10 µM CBG + 10 µM Compound 1 | 1470 | 111 |

Glucuronide Formation

| Test system | | CBG glucuronide formed (area ratio) | Percent of control |
|---|---|---|---|
| rUGT1A9 | 10 µM CBG | 371000 | 100 |
| | 10 µM CBG + 0.01 µM Compound 1 | 350000 | 94.4 |
| | 10 µM CBG + 0.03 µM Compound 1 | 360000 | 97.1 |
| | 10 µM CBG + 0.1 µM Compound 1 | 341000 | 92.0 |
| | 10 µM CBG + 0.3 µM Compound 1 | 350000 | 94.4 |
| | 10 µM CBG + 1 µM Compound 1 | 343000 | 92.6 |
| | 10 µM CBG + 3 µM Compound 1 | 347000 | 93.6 |
| | 10 µM CBG + 10 µM Compound 1 | 344000 | 92.8 |
| rUGT2B7 | 10 µM CBG | 249000 | 100 |
| | 10 µM CBG + 0.01 µM Compound 1 | 260000 | 104 |
| | 10 µM CBG + 0.03 µM Compound 1 | 252000 | 101 |
| | 10 µM CBG + 0.1 µM Compound 1 | 257000 | 103 |
| | 10 µM CBG + 0.3 µM Compound 1 | 262000 | 105 |
| | 10 µM CBG + 1 µM Compound 1 | 253000 | 102 |
| | 10 µM CBG + 3 µM Compound 1 | 252000 | 101 |
| | 10 µM CBG + 10 µM Compound 1 | 239000 | 96.0 |

The metabolism of CBG by the two isoforms was essentially unchanged by the presence Compound 1, whether CBG disappearance or glucuronide formation was assessed. These data demonstrate that Compound 1 is not an effective inhibitor of the conversion of CBG to a glucuronide.

Example 4. Hepatocyte Stability and Metabolite Profiling Report for CBG (CBG) in Cryopreserved Hepatocytes The objective of this study was to investigate the stability of the test compound, CBG, in human, rat, dog, mouse, monkey and minipig cryopreserved hepatocytes. Follow-on metabolite profiling was performed.

Hepatocyte Stability

CBG was incubated up to 2 hr with cryopreserved hepatocytes. Cryopreserved hepatocytes in suspension were added to test compound in supplemented media following pre-incubation to initiate the reaction and the reactions were stopped by organic solvent at the appropriate time points. The termination plates were centrifuged and sample supernatants were analysed using Cyprotex generic LC MS/MS conditions to generate intrinsic clearance values for CBG. Two control compounds for each species were included in the assay and if the values for these compounds were not within the specified limits the results were rejected and the experiment repeated.

As shown in Table 8 below CBG gave an intrinsic clearance value of 61.4 µL/min/106 cells, 28.3 µL/min/106 cells, 26.3 µL/min/106 cells, 32.8 µL/min/106 cells, 122 µL/min/106 cells and 32.5 µL/min/106 cells in cryopreserved human, rat, dog, mouse, monkey and minipig hepatocytes, respectively.

TABLE 8

Hepatocyte stability CBG data

| Species | CLint(µL/min/$10^6$ cells) | SE CLint | $t_{1/2\ (min)}$ | n |
|---|---|---|---|---|
| Human | 61.4 | 12.6 | 22.6 | $5^a$ |
| Rat | 28.3 | 4.46 | 49.0 | 6 |
| Dog | 26.3 | 5.22 | 52.7 | $5^a$ |
| Mouse | 32.8 | 2.91 | 42.2 | $5^a$ |
| Monkey | 122 | 32.3 | 11.3 | $4^b$ |
| Minipig | 32.5 | 5.85 | 42.7 | $5^a$ | n = number of concentrations used to fit curve:
SE = Standard error of the curve fitting:
[a] = 120 minute time point excluded:
[b] = 60 and 120 minute time points excluded.

Metabolite Profiling

Following the hepatocyte stability assay the samples were 59tilized for metabolite profiling using suitable high-resolution LC-MS/MS conditions. The 40 and 60 minute human samples, 20 and 120 minute rat samples, 10 and 20 minute dog and monkey samples, 20 and 60 minute mouse samples, and 40 and 120 minute minipig samples were compared against the 0 minute control sample to establish which and how many metabolites were formed. The data acquired for the mouse hepatocyte samples showed instability in both the live and associated lysed samples indicating solubility and/or non-specific binding. No further analysis was carried out with the mouse species.

The areas and percentages reported for the parent and metabolites were calculated using the XIC data. Metabolite observed at greater than 1% of the total of drug related material are reported. The m/z found for each metabolite in each species, and its associated ppm error, have been displayed for each species from the time point showing the largest peak area. For accuracy, a ppm error of less than 5 is desirable; when the response for a metabolite observed is low the ppm error maybe greater than 5. Where a metabolite has been referred to as a potential oxidation it can refer to a potential hydroxylation, epoxidation or oxide formation. Representative collision induced dissociation (CID) mass spectra were obtained for the metabolites found.

In summary, a total of twelve metabolites have been found and reported. Seven, eight, three, four and four metabolites were observed in human, rat, dog, monkey and minipig hepatocyte samples respectively. These data showed that glucuronidation is the major driver of metabolism and the only metabolite seen in all species. Structural elucidation is provided for five of these metabolites, M1, M2, M4 (See FIG. 13), M7 and M10 (See FIG. 14). Structures are depicted in Markush format with the shaded area showing potential sites of modification.

Example 5: PK Study

Protocol

This study evaluated the pharmacokinetics of (E)-2-(3,7-dimethylocta-2,6-dien-1-yl)-3-methoxy-5-pentylphenol (1) and (E)-2-(3,7-dimethylocta-2,6-dien-1-yl)-1,3-dimethoxy-5-pentylbenzene (2) following oral (PO) or intraperitoneal (IP) administration to male Sprague Dawley rats. The study design is shown in the Table 9 below.

Other compounds of the present disclosure (e.g., one or more compounds of Formula (I), (II), (III), Table 1 or Table 2) may also be evaluated using this protocol.

TABLE 9

Dosing regimens of CBG, Compound 1, and Compound 2

| Group | N/Sex | Test Article | Dose (mg/kg) | Conc (mg/mL) | Dose Volume (mL/kg) | Vehicle | Route |
|---|---|---|---|---|---|---|---|
| 1 | 7/M | CBG | 30 | 6 | 5 | 20% Maisine, 30% Labrasol and 50% water | PO |
| 2 | 7/M | Cmpd 1 | 31.5 | 6.3 | 5 | 20% Maisine, 30% Labrasol and 50% water | PO |
| 3 | 7/M | Cmpd 2 | 32.7 | 6.6 | 5 | 20% Maisine, 30% Labrasol and 50% water | PO |
| 4 | 7/M | CBG | 30 | 6 | 5 | 10% Ethanol, 10% Tween-20 and 80% Saline | IP |

Dose Formulation

For the oral formulation the test article was added to the appropriate amount of Maisine and stirred until uniform. Next Labrasol was added to the formulation and allowed to stir until uniform. Finally, water will be slowly added to the stirring formulation to achieve the final volume.

For the IP formulation the test article was added to the appropriate amount of ethanol and stirred until uniform. Next, the appropriate amount of tween-20 was added to the stirred formulation. Finally, the appropriate amount of saline was slowly added to the stirred formulation to achieve the final volume.

Animals were fasted the evening prior to dosing with food returned at 4 h postdose, and the animals weighed on the morning of dose administration.

Dose Administration:

IP doses were administered via injection to the intraperitoneal region. PO doses were delivered into the stomach via syringe and gavage tube.

Blood was collected from via direct jugular stick or from the tail vein. Blood samples were kept on ice until being centrifuged at 3200 RPM for 10 minutes at ~5° C. within 1 h of collection. Plasma was split into 2 cryovials in approximately equal volumes (0.05 mLs) and stored at −20° C.±5° C. until shipment.

Results

The Plasma Concentration vs Time Profile graphs for Groups 1-4 are shown in FIGS. 1-10. The parent compound CBG was converted by glucuronidation to CBG-glucuronide following both oral and IP administration (see FIG. 5, FIG. 6, FIG. 11 and FIG. 12). In contrast, Compound 1 showed significantly reduced levels of glucuronidation compared to CBG (see FIG. 7 and FIG. 8) and Compound 2 completely blocked glucuronide formation (see FIG. 9 and FIG. 10). Thus, both Compound 1 and Compound 2 exhibited much higher bioavailability than CBG.

Example 6. Anti-Inflammatory Activity of CBG and Derivatives in a Rat LPS Model

This assay was employed to determine the efficacies of CBG, compound 1, and compound 2 against lipopolysaccharide (LPS)-induced inflammation in Sprague Dawley rats.

Other compounds of the present disclosure (e.g., one or more compounds of Formula (I), (II), (III), Table 1 or Table 2) may also be evaluated using this protocol.

Protocol:

Eight- to 10-week-old male rats were treated with CBG, Compound 1, and Compound 2, or a positive control (cyclosporin A) for four days prior to treatment with LPS. Twenty-eight (28) Sprague Dawley male rats, 8-10 weeks old, were used for this study. Animals were randomized by weight into one of 7 treatment groups as shown in Table 10 below and treated for 4 days with either vehicle control (Groups 1 and 2), Cyclosporin A (Neoral) (Group 3), CBG at 30 mg/kg (Group 4), Compound 1 at 31.5 mg/kg (Group 5), Compound 2 at 32.7 mg/kg (Group 6) or CBG at 30 mg/kg (intraperitoneal/IP; Group 7). Groups 1-6 were dosed for 4 days by oral gavage; group 7 was dosed for 4 days by IP injection. After the 4th injection, Groups 2-7 received a single IP injection of LPS at 5 mg/kg to induce inflammation. Body weight was recorded every other day starting on the day of or day prior to the first day of treatment. A terminal body weight was recorded. General health and clinical signs were recorded once daily. Blood was collected to isolate immune cells at 2 hours after the LPS injection. Animals were humanely euthanized after blood collection. Immune cells were isolated from whole blood and supplied as a cell pellet for cytokine analysis.

TABLE 10

Dosing regimens of CBG, Compound 1, and Compound 2

| Group # | Treatment | Dosages (mg/kg) | Vehicle | Route | Frequency | LPS injection day 4 | Males |
|---|---|---|---|---|---|---|---|
| 1 | Vehicle | N/A | 20% Maisine, 30% Labrasol and 50% water | PO | QD × 4 | N/A | 4 |
| 2 | Vehicle | N/A | 20% Maisine, 30% Labrasol and 50% water | PO | QD × 4 | 5 mg/kg IP | 4 |
| 3 | Cyclosporine A | 70 | Phosphate Buffered Saline | PO | QD × 4 | 5 mg/kg IP | 4 |
| 4 | CBG | 30 | 20% Maisine, 30% Labrasol and 50% water | PO | QD × 4 | 5 mg/kg IP | 4 |
| 5 | Compound 1 | 31.5 | 20% Maisine, 30% Labrasol and 50% water | PO | QD × 4 | 5 mg/kg IP | 4 |
| 6 | Compound 2 | 32.7 | 20% Maisine, 30% Labrasol and 50% water | PO | QD × 4 | 5 mg/kg IP | 4 |
| 7 | CBG | 30 | 10% Ethanol, 10% Tween-20, 80% Saline | IP | QD × 4 | 5 mg/kg IP | 4 |

Ex Vivo Analysis of Cytokines

Cytokines known to be pro-inflammatory and particularly involved in inflammatory bowel disease (IBD) are IL-1B, IFNy and TNFa. A study was conducted to analyze rat serum these cytokines in samples from Groups 1-7 of the study described above.

Figure 15B:
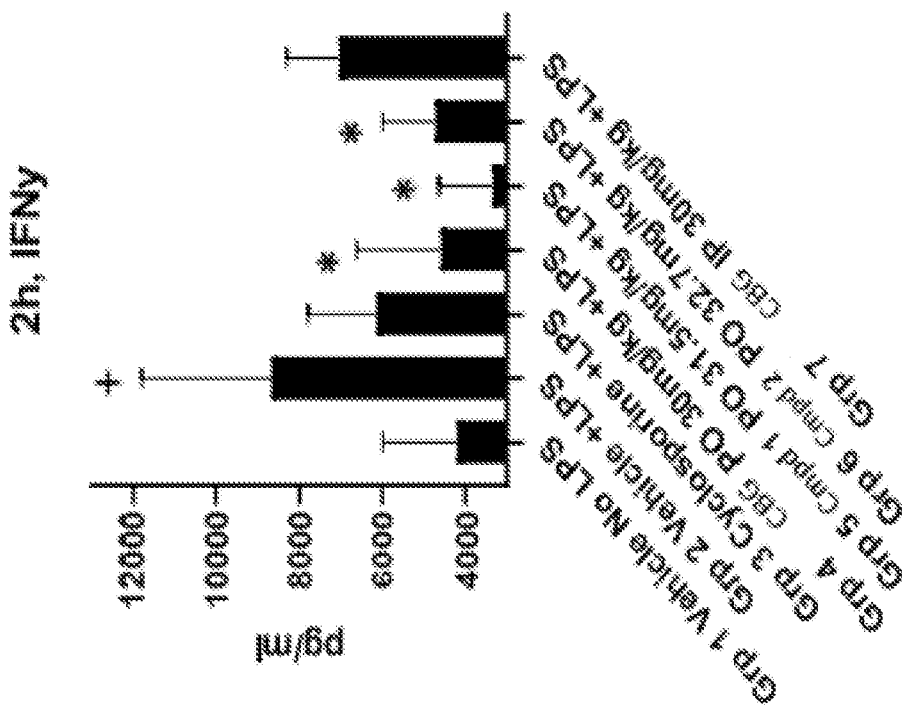
FIGS. 15A-C show graphs representing serum concentrations (pg/mL) of (A) IL-1β, (B) INFγ, and (C) TNFα pro-inflammatory cytokines following Cyclosporine A, CBG, Compound 1 or Compound 2 administration in rat LPS model.
Figure 15A:
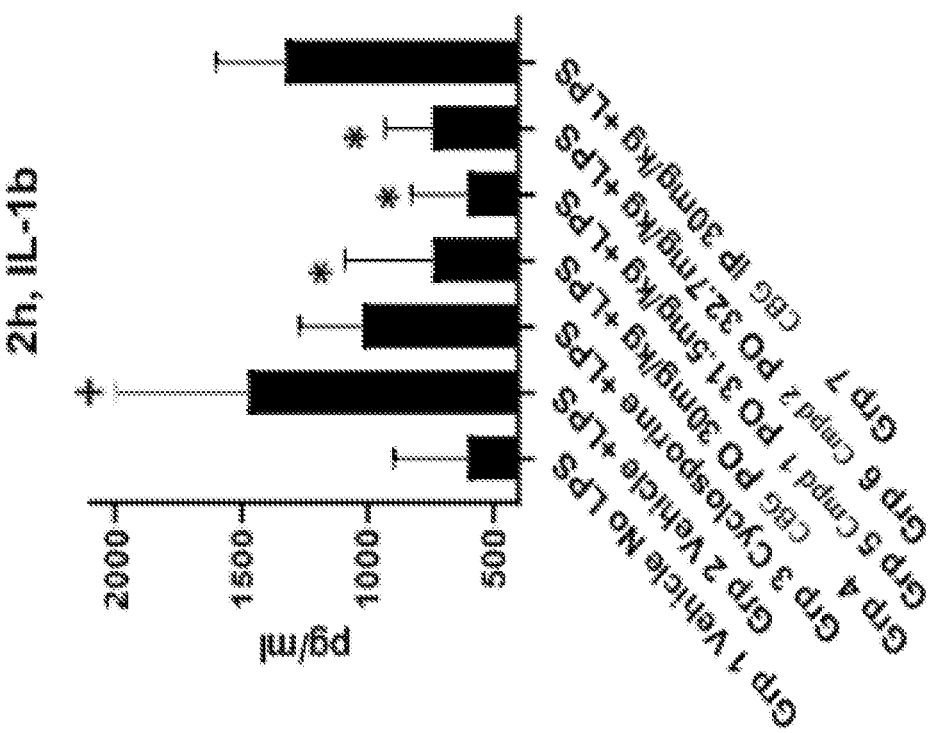
Figure 15C:
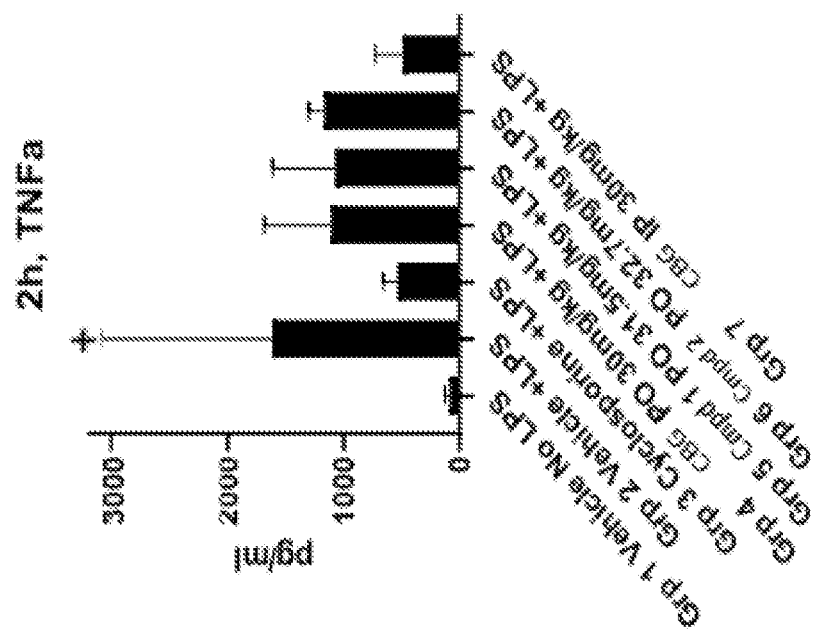

Serum samples (N=82) were processed and shipped to Inotiv Boulder for analysis. The samples were derived from twenty-eight (28) rats with a collection time point (2 h). The samples were analyzed for cytokine levels using the RECYTMAG-65K Luminex™ kit. The results of the assays are reported in FIG. 15A, FIG. 15B and FIG. 15C.

Statistical analysis: Wilcox rank sum analysis was conducted for the 2-hour time point. This type of analysis was appropriate due to the non-Gaussian nature of the data. An initial Groups 1 and 2 comparison demonstrated the LPS treatment resulted in significant changes in cytokine levels. Next, Groups 4, 5, and 6 were compared to Group 2 to determine if there were significant changes in cytokine levels as results of drug treatment. Significant differences between Group 1 and 2 were indicated by a plus sign (+) on the summary bar graphs and statistical differences for Groups 4, 5 and 6 versus group 2 were dictated by were also marked with an asterisks (*) on the bar graphs.

Results:

For IL-1B and IFNy all three orally dosed treatment groups (Groups 4-6) showed a significant reduction in the pro-inflammatory cytokines in comparison to Group 2. In both cases Compound 2 and Compound 3 performed equal to or better than CBG, indicating enhanced bioavailability may contribute to better anti-inflammatory efficacy. Although TNFa reduction was not significant there was a downward trend in the oral treatment Groups 4-6.

Example 7. Effects of Compound 1 and Compound 2 Administered in an Indomethacin-Induced Crohn's Disease in Rats The objective of this study was to determine the efficacy of Compound 1 and Compound 2 in a model of Crohn's disease (indomethacin induced intestinal injury) in rats.

Other compounds of the present disclosure (e.g., one or more compounds of Formula (I), (II), (III), Table 1 or Table 2) may also be evaluated using this protocol.

Study Design

The study design was identical for Compound 1 and Compound 2. On study day −3, rats were weighed and distributed into treatment groups based on body weight.

On study day 0, treatment was initiated and continue as indicated in the Study Design Tables below. Groups 2-6 received a subcutaneous injection of indomethacin (9 mg/kg, 1 ml/kg) in 5% sodium bicarbonate (Sterile Water). On study day 1, Groups 2-6 received a second subcutaneous injection of indomethacin (8 mg/kg, 1 ml/kg) in 5% sodium bicarbonate (Sterile Water). Live phase sample & data collection specifics are outlined below. On study day 4, animals will be euthanized, a section of the small intestine will be removed and weighed. Further necropsy sample and data collection is specified below. Overall efficacy of test articles will be based on body weight, small intestine weight (10 cm), small intestine gross score, and histopathology

TABLE 11

Compound 1 Study Design Table

| Group | N | Disease | Treatment | Dose (mg/kg) | Route, Regimen | Dosing Days | Vehicle |
|---|---|---|---|---|---|---|---|
| 1 | 5 | No | Normal | N/A | N/A | 0-3 | N/A |
| 2 | 10 | Yes | Vehicle | N/A | PO | 0-3 | DM-P1-2 |
| 3 | 10 | Yes | Dexamethasone | 0.1 | PO | 0-3 | 1% CMC |
| 4 | 10 | Yes | Compound 1 | 50 | PO | 0-3 | DM-A1-2 |
| 5 | 10 | Yes | Compound 1 | 200 | PO | 0-3 | DM-A1-2 |
| 6 | 10 | Yes | Compound 1 | 800 | PO | 0-3 | DM-A1-2 |

TABLE 12

Compound 2 Study Design Table

| Group | N | Disease | Treatment | Dose (mg/kg) | Route, Regimen | Dosing Days | Vehicle |
|---|---|---|---|---|---|---|---|
| 1 | 5 | No | Normal | N/A | N/A | 0-3 | N/A |
| 2 | 10 | Yes | Vehicle | N/A | PO | 0-3 | DM-P1-2 |
| 3 | 10 | Yes | Dexamethasone | 0.1 | PO | 0-3 | 1% CMC |
| 4 | 10 | Yes | Compound 2 | 50 | PO | 0-3 | DM-A1-2 |
| 5 | 10 | Yes | Compound 2 | 200 | PO | 0-3 | DM-A1-2 |
| 6 | 10 | Yes | Compound 2 | 800 | PO | 0-3 | DM-A1-2 |

At necropsy, the small intestines were evaluated visually and given a gross score according to the following criteria: •0=Normal. 0.5=Very Minimal thickening, multifocal in area at risk. 1=Minimal thickening, fairly diffuse in area at risk. 2=Mild to moderate small intestinal/mesenteric thickening throughout area at risk. 3=Moderate thickening with 1 or more definite adhesions that would be easy to separate. 4=Marked thickening with numerous hard to separate adhesions. 5=Severe intestinal lesion resulting in death.

Morphologic Pathology Methods

Preserved 9-cm sections of small intestine were trimmed into 6 transverse sections collected at approximately equal intervals along the width of the intestine, without bias toward lesion presence or absence. These trimmed sections were processed through graded alcohols and a clearing agent, infiltrated and embedded in paraffin, sectioned, and stained with hematoxylin and eosin (H&E).

Small intestine sections from all animals were examined microscopically by a board-certified veterinary pathologist, and observations were entered into a computer-assisted data retrieval system. Cross sections of small intestine were scored for inflammation and necrosis using the following criteria:

TABLE 13

Necrosis Scoring Criteria

| Score | Observation |
|---|---|
| 0= | None |
| 0.5= | 1-499 µm width, generally <5% of mucosa affected |
| 1= | 500-1000 µm width, generally 5-10% of mucosa affected |
| 2= | 1001-1500 µm width, generally 11-15% of mucosa affected |
| 3= | 1501-2000 µm width, generally 16-20% of mucosa affected |
| 4= | 2001-3000 µm width, generally 21-25% of mucosa affected |
| 5= | Greater than 3000 µm width >25% of mucosa affected |

The area at risk for development of this lesion is generally approximately 30% of the total area of a cross section of small intestine where the mesentery attaches. The total circumference is generally about 10,000 m and of this total, only about 4000 m is generally at risk for lesion development, hence the low range for the % mucosa affected.

TABLE 14

Inflammation Scoring Criteria

| Score | | Observation |
|---|---|---|
| 0= | None | |
| 0.5= | Very minimal= | Localized to mesentery, very minimal in intestine, (generally associated with necrosis score of 0.5 if necrosis is present) |
| 1= | Minimal= | Diffuse in mesentery and focal in intestinal lesion if present (generally associated with necrosis score of 1, or higher necrosis scores if there is an anti-inflammatory effect in the absence of a beneficial effect on necrosis) |
| 2= | Mild= | Diffuse in mesentery and intestinal lesion (generally associated with necrosis score of 2 or higher) |
| 3= | Moderate= | Diffuse in mesentery and intestinal lesion (generally associated with necrosis score of 3 or higher) |
| 4= | Marked= | Diffuse in mesentery and intestinal lesion (generally associated with necrosis score of 4 or higher) |
| 5= | Severe= | Diffuse in mesentery and intestinal lesion (generally associated with necrosis score of 5 or higher) |

Inflammation is localized to the mesentery and intestinal area at risk for necrosis with slight extension on either side of it. Therefore, the inflammation severity generally tracks with the necrosis and hence has similar scores except where necrosis occurs, and inflammation is down modulated by treatments. In this case, inflammation is scored based on overall severity ranging from 0.5 (very minimal) to 5 (severe) without regard for the extent of necrosis. The mean score for necrosis and inflammation was calculated for each animal and these mean scores were then summed to arrive at a total score. Each section also has a measurement of total width of mucosal necrosis.

Results

Figure 16:
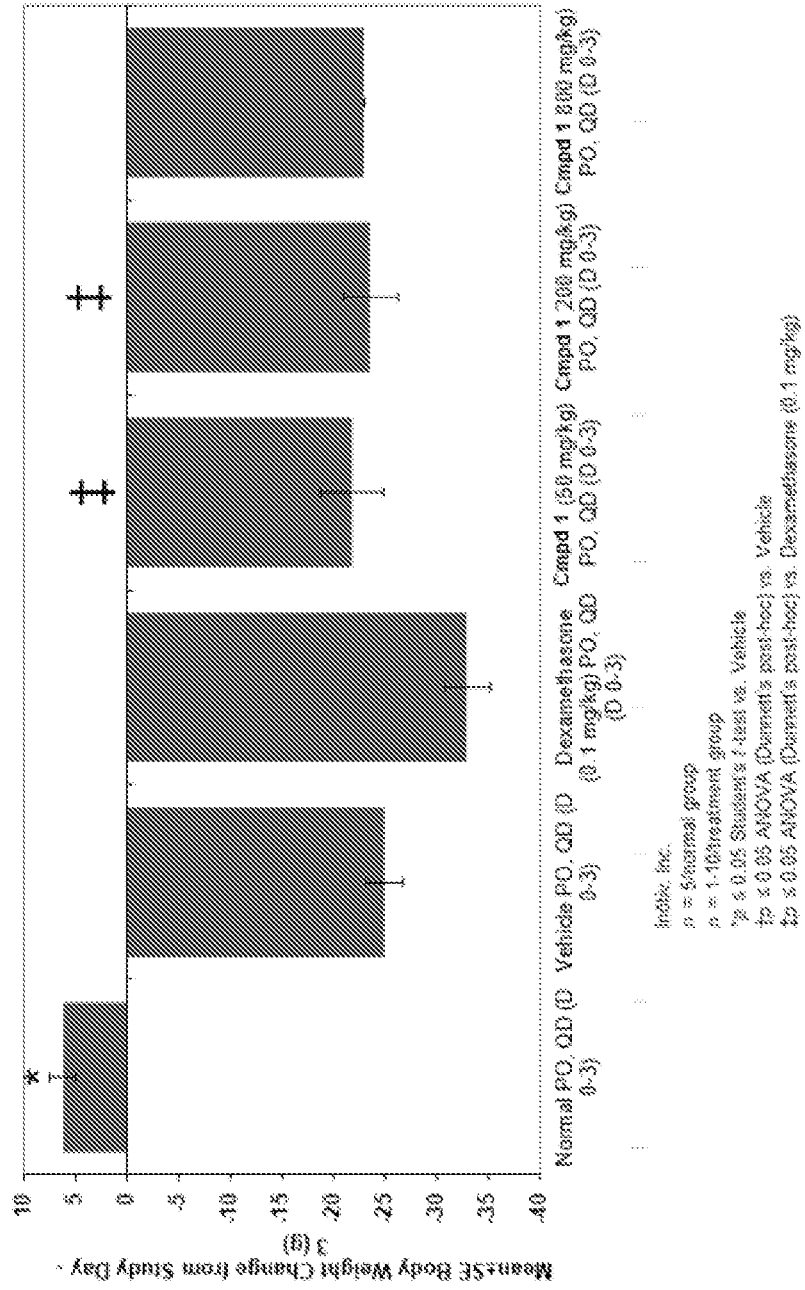
FIG. 16 shows body weight change from Study Day −3 in rats administered compound 1 compared to positive control dexamethasone, vehicle and normal rats in the study described in Example 7.
Figure 17:
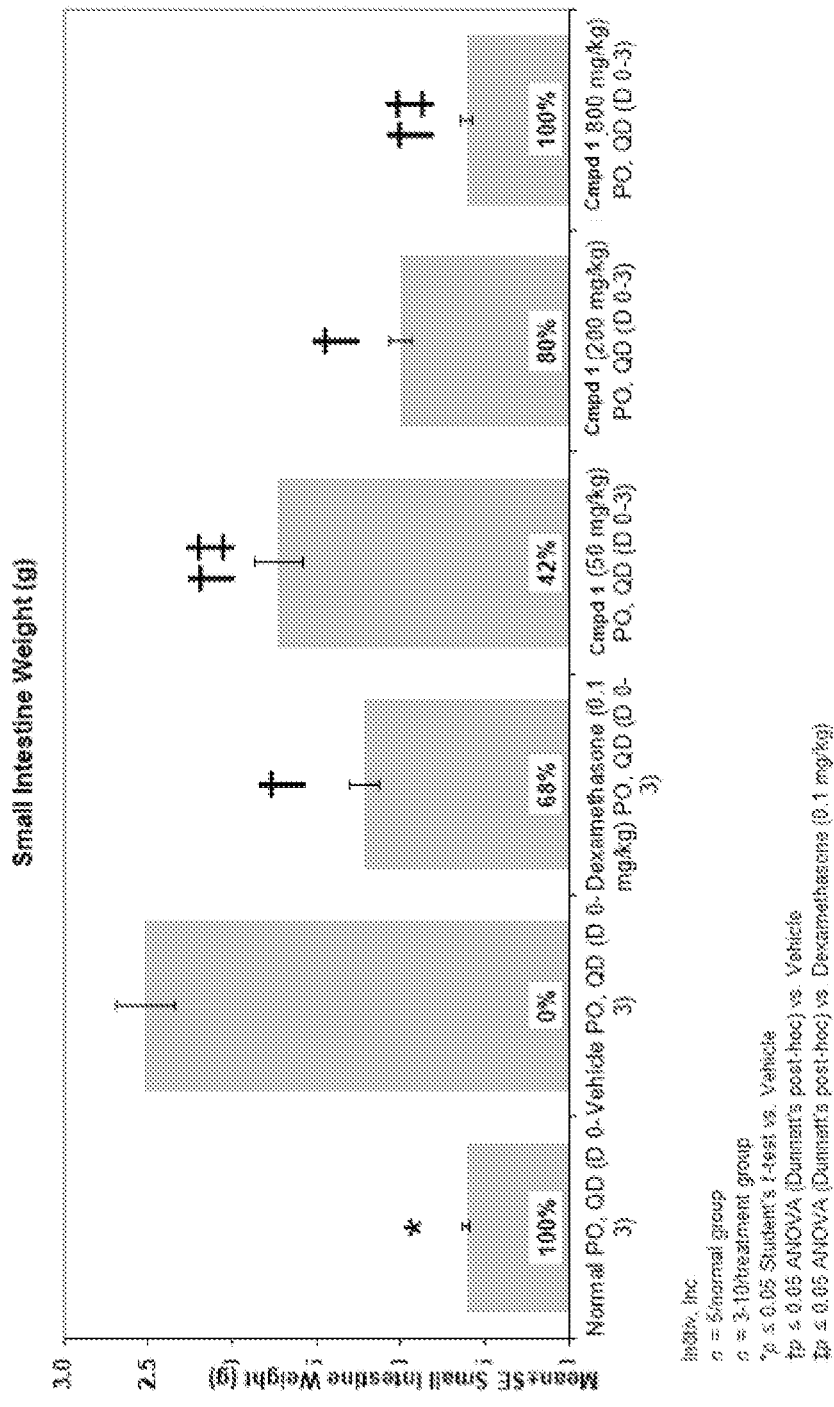
FIG. 17 shows small intestine weight in rats administered compound 1 compared to positive control dexamethasone, vehicle and normal rats in the study described in Example 7.
Figure 18:
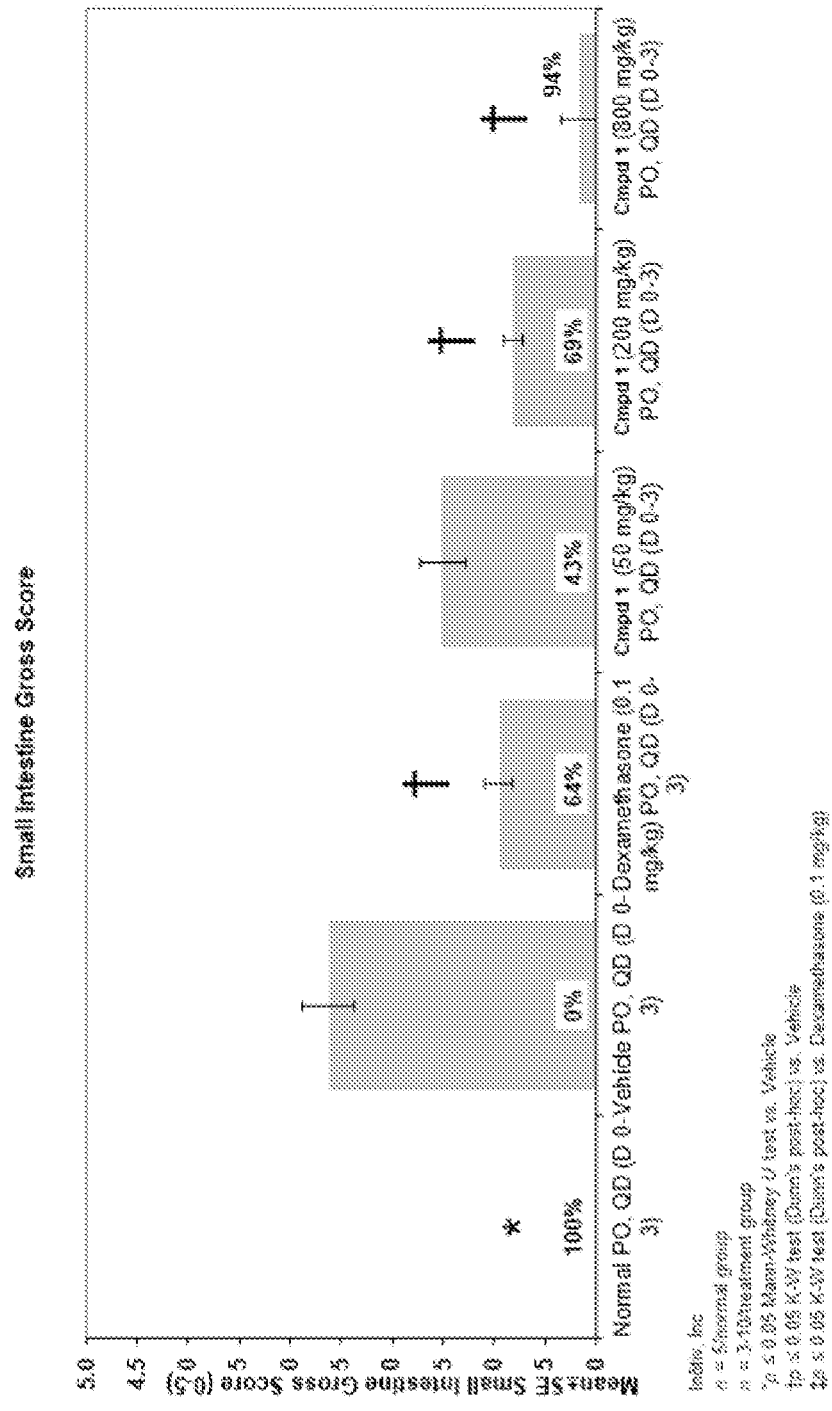
FIG. 18 shows lower small intestine gross score in rats administered compound 1 compared to positive control dexamethasone, vehicle and normal rats in the study described in Example 7.

The Compound 1 treatment groups all trended towards or had significant differences in preventing weight loss in comparison to the positive control dexamethasone (FIG. 16). All three treatment groups for Compound 1 showed significantly lower small intestine weight compared to vehicle (FIG. 17). Group 4 showed a trend in lower small intestine gross score while both Groups 5-6 had significant reductions in gross score compared to vehicle (FIG. 18).

Figure 19:
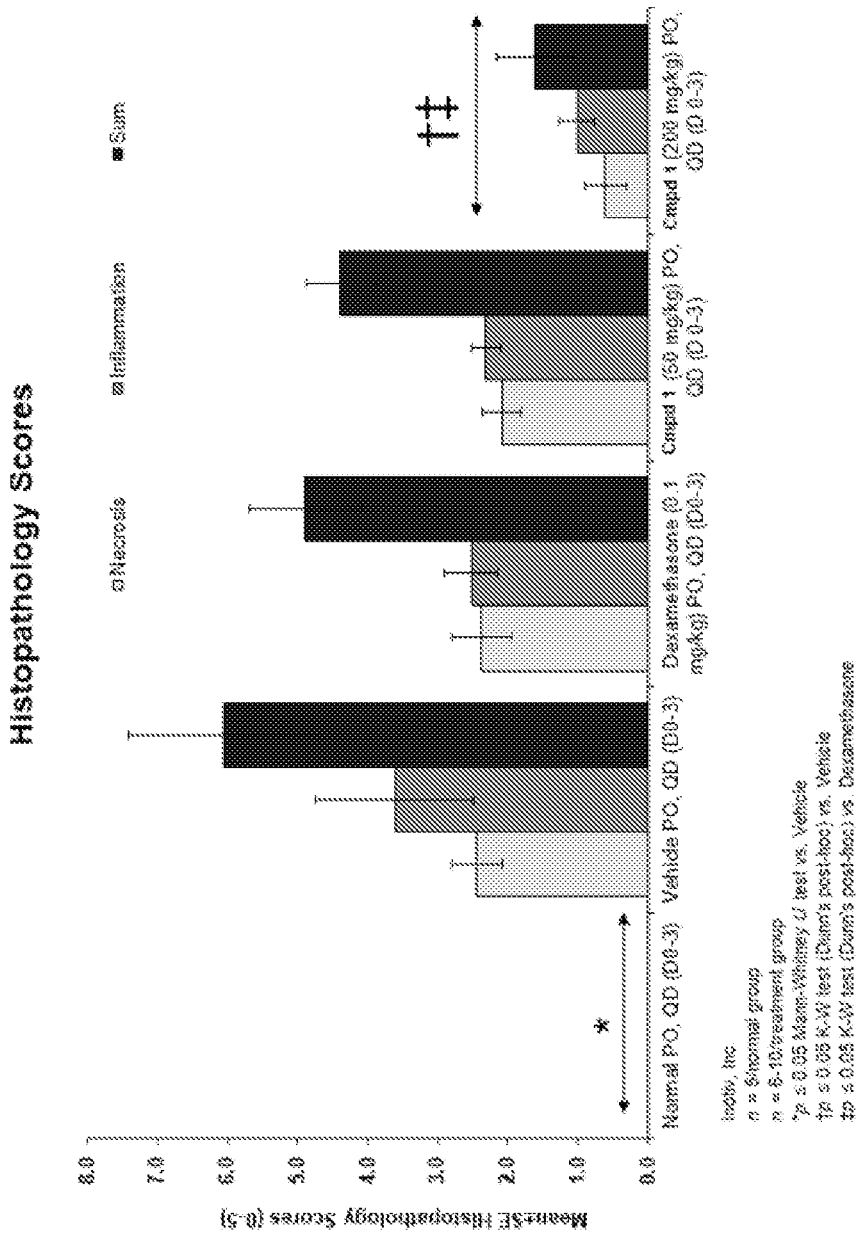
FIG. 19 shows histopathology scores in rats administered compound 1 compared to positive control dexamethasone, vehicle and normal rats in the study described in Example 7.
Figure 20:
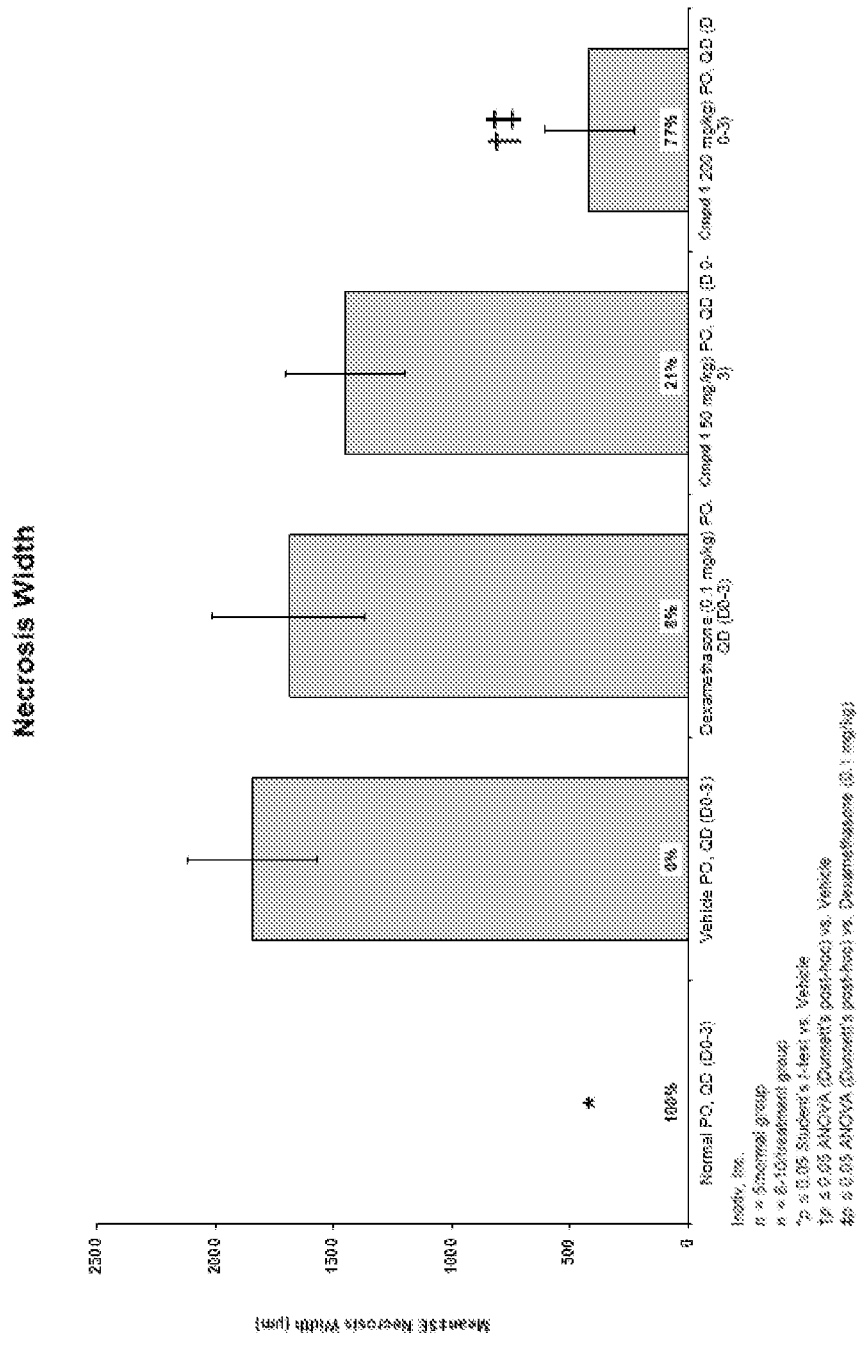
FIG. 20 shows necrosis width in rats administered compound 1 compared to positive control dexamethasone, vehicle and normal rats in the study described in Example 7.

Histopathology scores and necrosis width for all Compound 1 treatment Groups 4 and 5 trended lower than both the vehicle (Group 2) and positive control groups (Group 3) (FIG. 19). Compound 1 treatment in Group 5 had significantly lower histopathology scores and necrosis width than vehicle and dexamethasone (FIG. 19 and FIG. 20). All these data indicate that Compound 1 is a drug candidate for the treatment of Crohn's Disease.

Figure 21:
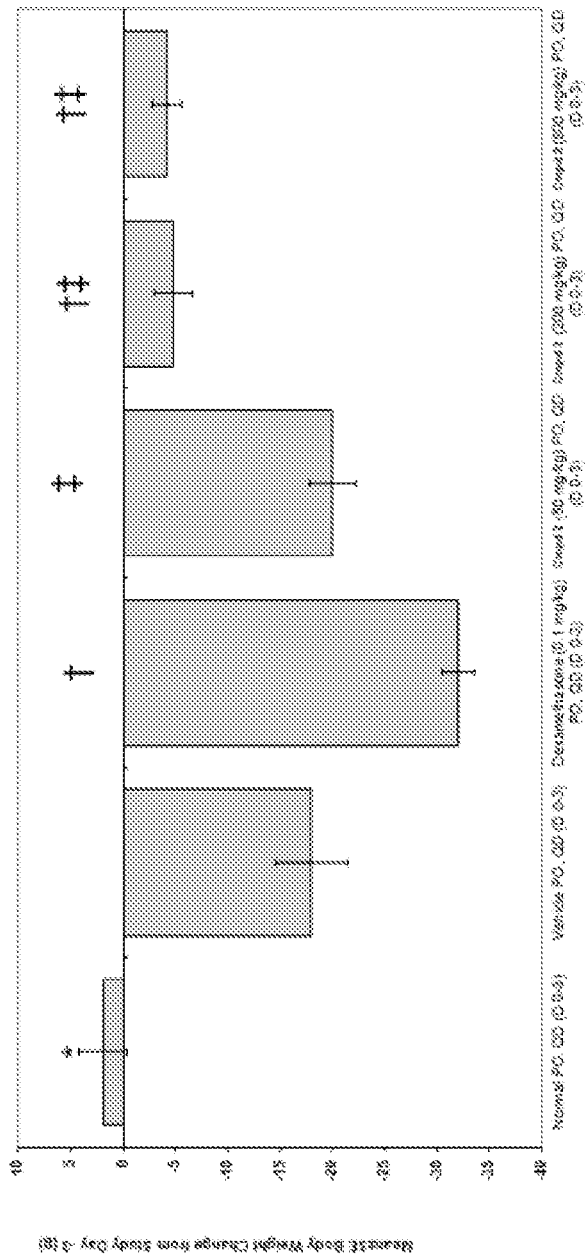
FIG. 21 shows body weight change from Study Day −3 in rats administered compound 2 compared to positive control dexamethasone, vehicle and normal rats in the study described in Example 7.
Figure 22:
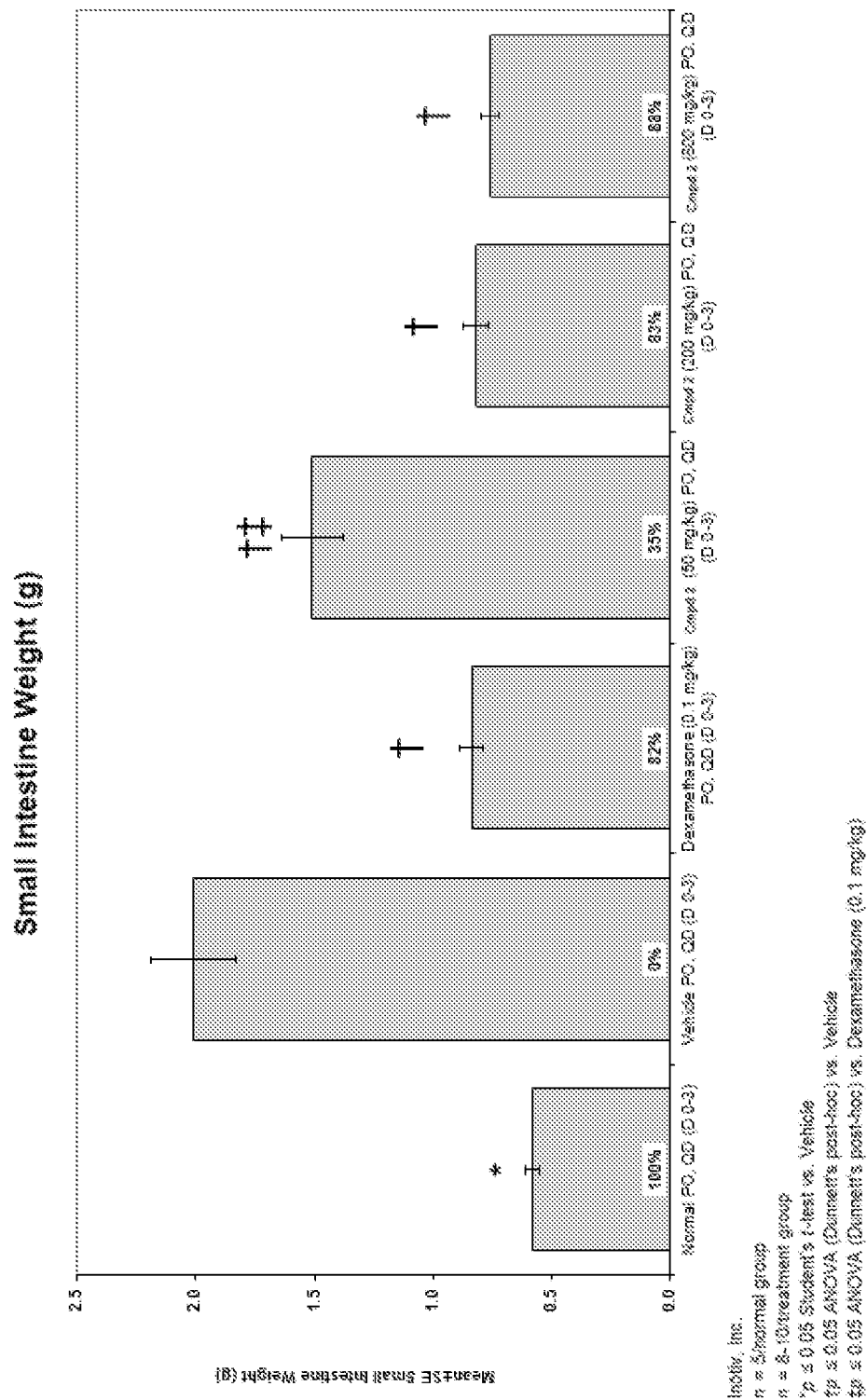
FIG. 22 shows small intestine weight in rats administered compound 2 compared to positive control dexamethasone, vehicle and normal rats in the study described in Example 7.
Figure 23:
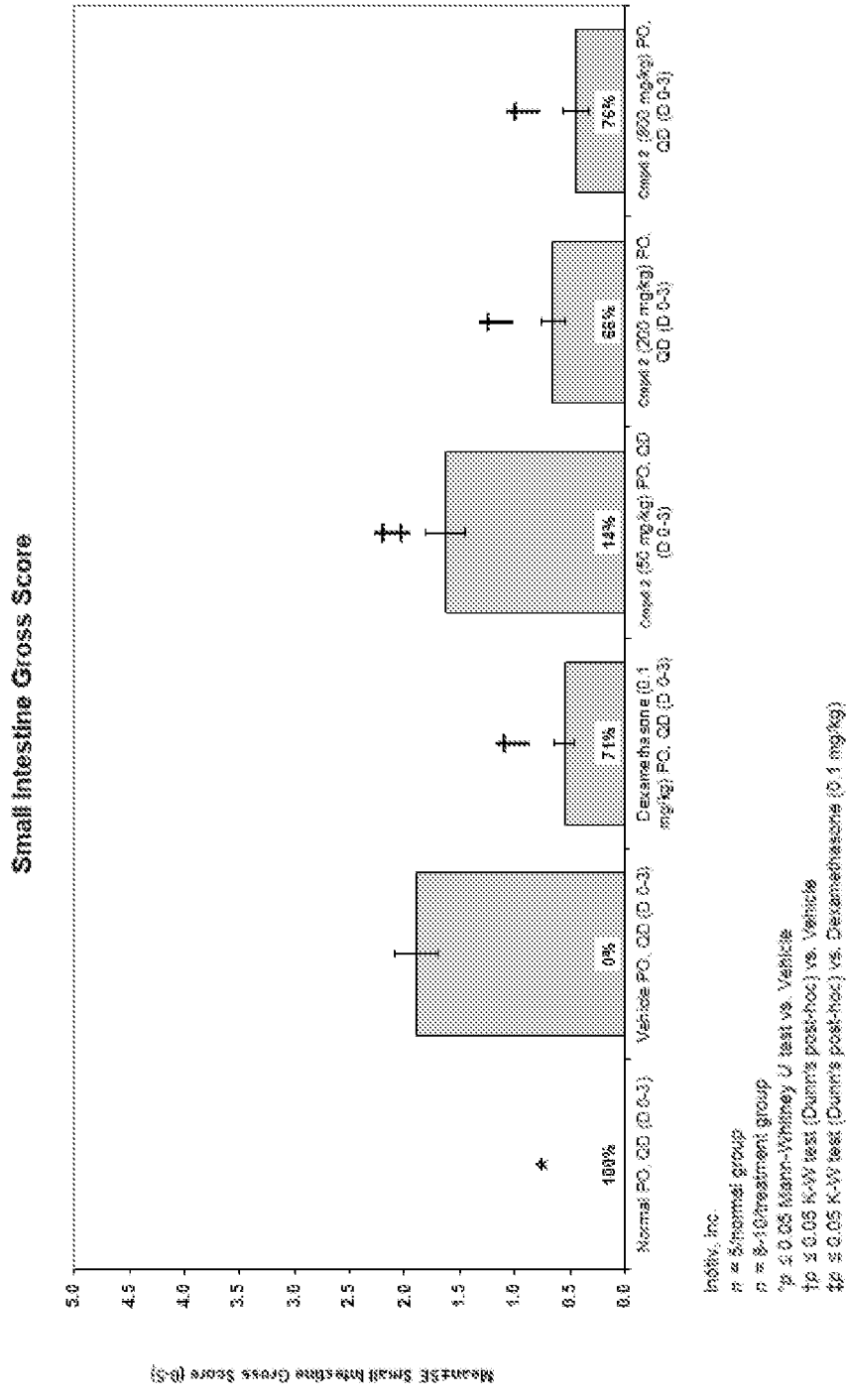
FIG. 23 shows lower small intestine gross score in rats administered compound 2 compared to positive control dexamethasone, vehicle and normal rats in the study described in Example 7.

The Compound 2 treatment groups all trended towards or had significant differences in preventing weight loss in comparison to the positive control dexamethasone and the vehicle (FIG. 21). All three treatment groups for Compound 2 showed significantly lower small intestine weight compared to vehicle (FIG. 22). Group 4 showed a trend in lower small intestine gross score while both Groups 5-6 had significant reductions in gross score compared to vehicle (FIG. 23).

Figure 24:
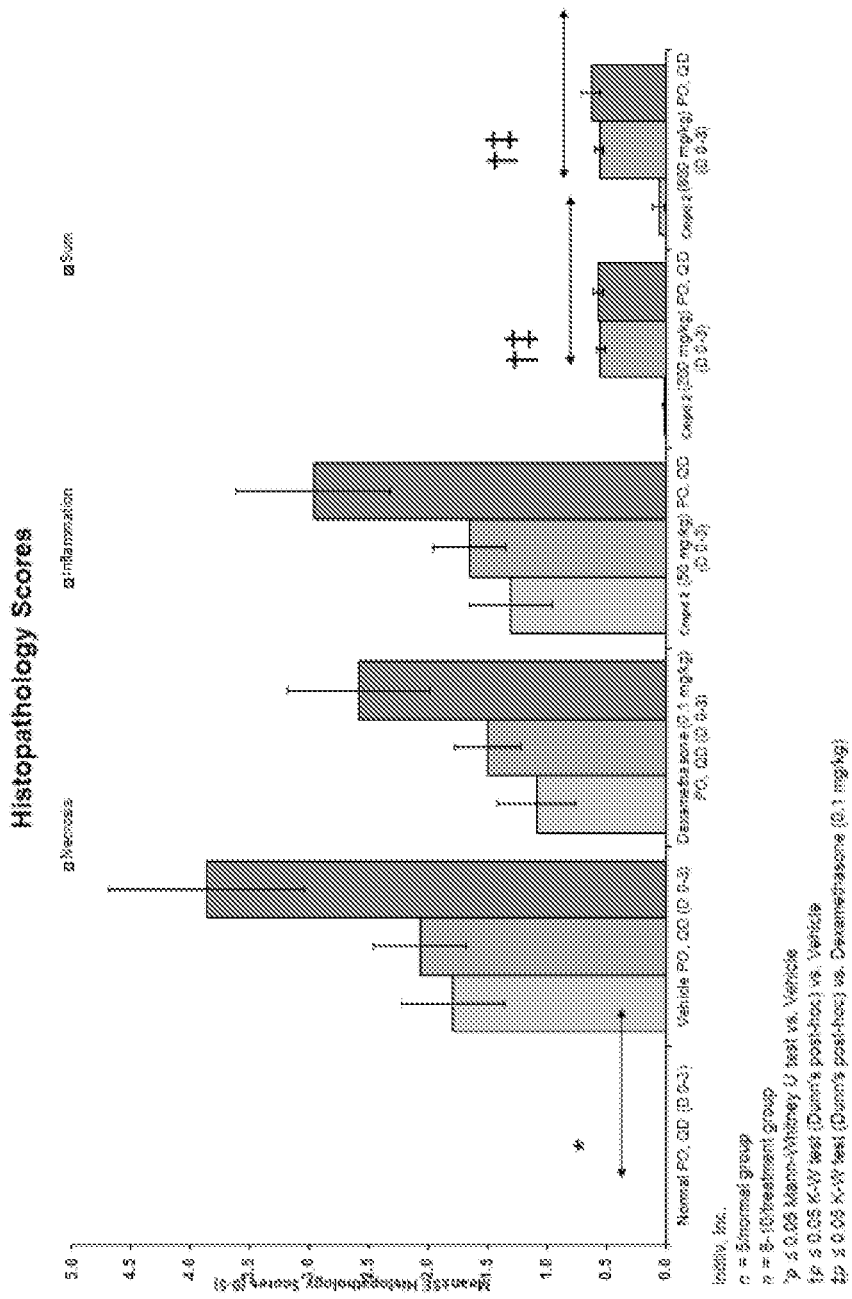
FIG. 24 shows histopathology scores in rats administered compound 2 compared to positive control dexamethasone, vehicle and normal rats in the study described in Example 7.
Figure 25:
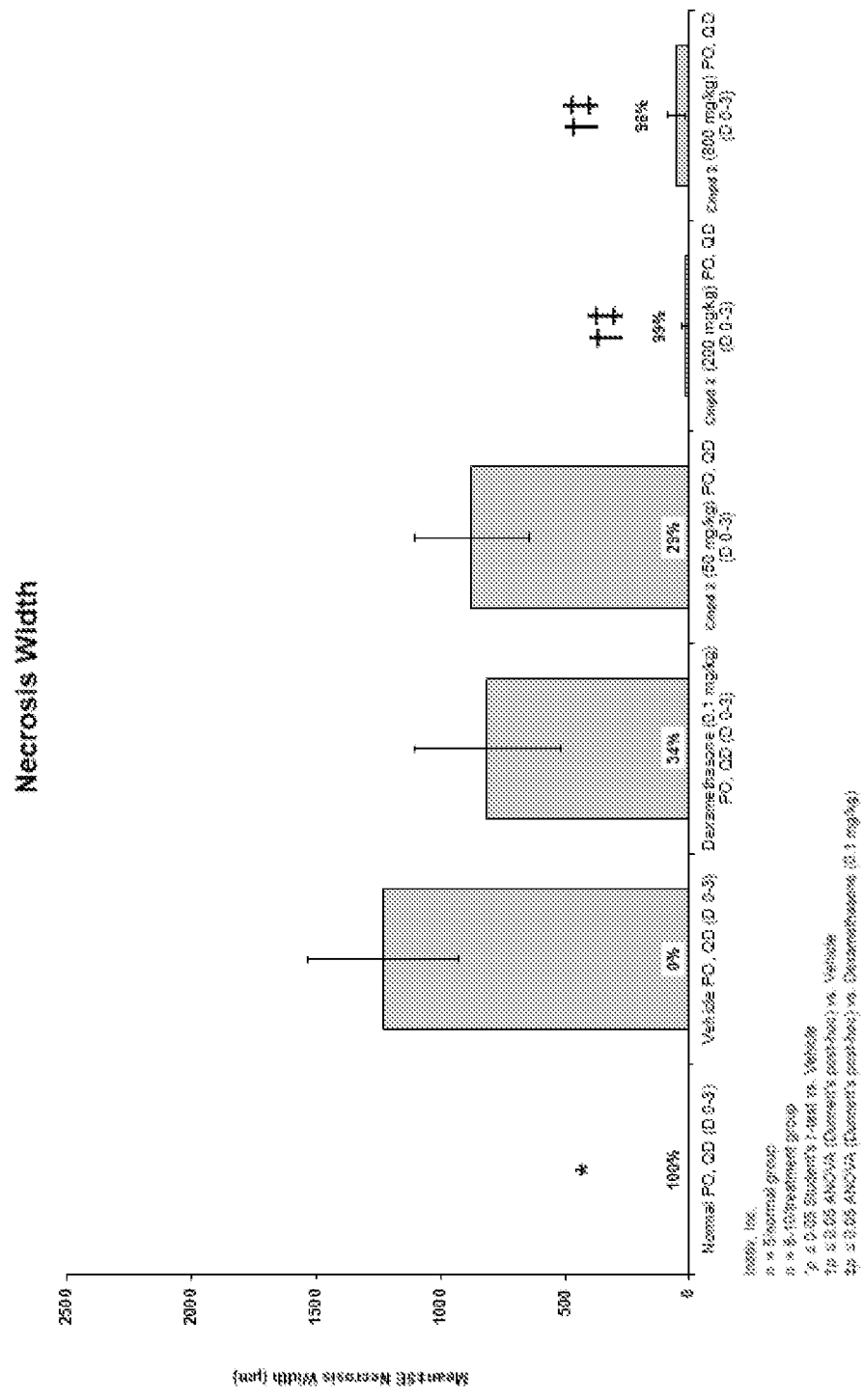
FIG. 25 shows necrosis width in rats administered compound 2 compared to positive control dexamethasone, vehicle and normal rats in the study described in Example 7.

Histopathology scores and necrosis width all Compound 2 treatment Groups 4-6 were lower than the vehicle (Group 2) (FIG. 24 and FIG. 25). Compound 2 treatment in Group 5 & 6 had significantly lower histopathology scores and necrosis width than vehicle and dexamethasone. Groups 5 & 6 were especially impressive in reducing the necrosis width by 99% and 96% of vehicle respectively. All these data indicate that Compound 2 is a drug candidate for the treatment of Crohn's Disease.

Example 8. $GI_{50}$ Assay and Target Engagement Assay of DM Compounds on Colon Cancer Cell Lines The objective of this experiment is to screen the effect of compounds of the instant disclosure by measuring their capability to reduce the colon cancer cell viability and inhibit colony formation, and to investigate the target engagement by Western blot detection of specific protein expression under compound treatment.

Other compounds of the present disclosure (e.g., one or more compounds of Formula (I), (II), (III), Table 1 or Table 2) may also be evaluated in this assay.

| ABBREVIATION | DESCRIPTION |
| --- | --- |
| nm | nanometer |
| μM | micromolar |
| mM | milimolar |
| SD | Standard Deviation |
| FBS | Fetal Bovine Serum |
| DMSO | Dimethyl sulfoxide |

For MTS assay, the compounds have been tested at 8 concentrations on 4 colon cancer cell lines for 48 hours. The compounds, concentrations and colon cancer cell line panel tested are the following:
CBG: 0 μM, 1.25 μM, 2.5 μM, 5 μM, 10 μM, 20 μM, 40 μM, and 80 μM.
Compound 1: 0 μM, 1.25 μM, 2.5 μM, 5 μM, 10 μM, 20 μM, 40 μM, and 80 μM.
Compound 2: 0 μM, 1.25 μM, 2.5 μM, 5 μM, 10 μM, 20 μM, 40 μM, and 80 μM.
Colon cancer cell line panel: SW620, HCT15, HT29, HCTl16

For colonogenic assay, the compounds were tested at 4 concentrations for 1 week or 2 weeks on 4 colon cancer cell lines. The compounds, concentrations, colon cancer cell line panel and end time point tested are the following:
CBG: 0 μM, 10 μM, 20 μM, 40 μM, and 80 μM.
Compound 1: 0 μM, 5 μM, 7.5 μM, 10 μM, and 20 μM.
Compound 2: 0 μM, 10 μM, 20 μM, 40 μM, and 80 μM.
Colon cancer cell line panel and end time point: SW620, HCT15, HCT116, 1 week; HT29, 2 weeks For Western blot, the compounds were tested at 4 concentrations for 3 hours on 3 colon cancer cell lines. The compounds, concentrations, colon cancer cell line panel, and antibodies panel tested are the following:
CBG: 0 μM, 10 μM, 20 μM, 40 μM, and 80 μM.
Compound 1: 0 μM, 10 μM, 20 μM, 40 μM, and 80 μM.
Compound 2: 0 μM, 10 μM, 20 μM, 40 μM, and 80 μM.
Colon cancer cell line panel: SW620, HCT15, HCT116
Antibodies panel: p-cMYC(S62), cMyc, p-AKT(S473), AKT, p-ERK(T202/Y204), ERK Methods Four colon cancer cell lines of SW620, HCT15, HT29, and HCT116 were included in the colon cancer cell line panel.

CBG, compound 1 and compound 2 were dissolved in DMSO at a concentration of 10 mM and stored at −20° C.

Evaluation of DM compounds treatment-induced growth inhibition was performed to determine the GI50 of four colon cancer cell lines with MTS assay or clonogenic assay. Each experiment was repeated in triplicate. In GraphPad Prism, data were log-transformed and fit with a nonlinear curve to calculate the $GI_{50}$.

Evaluation of target engagement was performed to determine the expression of specific marker protein expression and underlying signaling pathways with Western blot.

MTS assay. cells were plated at 96 well plates at a density of 1,000 cells per well. After 24 hours, cells were treated with DM compounds at increasing concentrations or DMSO vehicle and incubated for 48 hours. 20 μl of MTS reagent (Promega) was then added and incubated for 2 hours. The absorbance was measured with a microplate reader at 490 nm. Each experiment was repeated in triplicate. In GraphPad Prism, data were log-transformed and fit with a nonlinear curve to calculate the $GI_{50}$.

Clonogenic assay. cells were plated at 6 well plates at a density of 2,500 cells per well. After 24 hours, cells were treated with DM compounds at increasing concentrations or DMSO vehicle and incubated for 1 week or 2 weeks. Cells were then fixed and stained with 1% crystal violet (Sigma-Aldrich) solution. Quantification was performed using ImageJ. Each experiment was repeated in triplicate. In GraphPad Prism, data were log-transformed and fit with a nonlinear curve to calculate the $GI_{50}$.

Western blot. Whole cell extracts were prepared by incubating cell pellets in IP lysis buffer supplemented with protease and phosphatase inhibitors (Roche). Isolated protein was quantified by Pierce BCA Protein assay (ThermoFisher). Equal quantities of protein were separated by 4-15% SDS-PAGE electrophoresis gels and transferred onto nitrocellulose membranes. Membranes was blocked with 5% nonfat milk in Tris-buffered saline-Tween buffer. The membrane were probed with the antibodies specific for p-ERK(T202/Y204) (Cell Signaling Technologies), ERK (Cell Signaling Technologies), p-AKT(S473) (Cell Signaling Technologies), AKT (Cell Signaling Technologies), p-cMyc(S62) (Abcam), cMyc (Santa Cruz Biotechnology), and Vinculin (Santa Cruz Biotechnology).

Results

Evaluation of compounds of the disclosure for treatment-induced loss of viability was performed to determine the $GI_{50}$ of four colon cancer cell lines with MTS assay or clonogenic assay.

Measured by MTS assay, the $GI_{50}$ of the CBG, compound 1, and Compound 2 on SW620 cells was 39.98±0.84, 8.76±1.38, and >80 μM respectively; the $GI_{50}$ of CBG, compound 1, and Compound 2 on HCT15 cells was 43.56±5.74, 10.01±0.52, and >80 μM respectively; the $GI_{50}$ of CBG, compound 1, and Compound 2 on HT29 cells was 43.58±4.02, 10.17±0.40, and >80 μM respectively; the $GI_{50}$ of CBG, compound 1, and Compound 2 on HCTl116 cells was 41.41±1.87, 10.30±0.24, and >80 μM respectively (Table 5).

TABLE 15

$GI_{50}$ (μM) of testcompounds measured with MTS assay.

| Cell line | Compound | N1 | N2 | N3 | AVG | SD |
| --- | --- | --- | --- | --- | --- | --- |
| SW620 | CBG | 39.51 | 39.42 | 38.02 | 38.98 | 0.84 |
| | Cmpd 1 | 8.47 | 7.55 | 10.26 | 8.76 | 1.38 |
| | Cmpd 2 | >80 | >80 | >80 | N/A | N/A |
| HCT15 | CBG | 50.17 | 30.18 | 40.69 | 43.56 | 5.74 |
| | Cmpd 1 | 10.08 | 9.46 | 10.50 | 10.01 | 0.52 |
| | Cmpd 2 | >80 | >80 | >80 | 35.89 | 8.95 |
| HT29 | CBG | 42.61 | 48.00 | 40.13 | 43.58 | 4.02 |
| | Cmpd 1 | 9.84 | 10.06 | 10.62 | 10.17 | 0.40 |
| | Cmpd 2 | >80 | >80 | >80 | N/A | N/A |
| HCT116 | CBG | 39.97 | 44.05 | 40.20 | 41.41 | 1.87 |
| | Cmpd1 | 10.50 | 9.96 | 10.45 | 10.30 | 0.24 |
| | Cmpd 2 | >80 | >80 | >80 | N/A | N/A |

Figure 26:
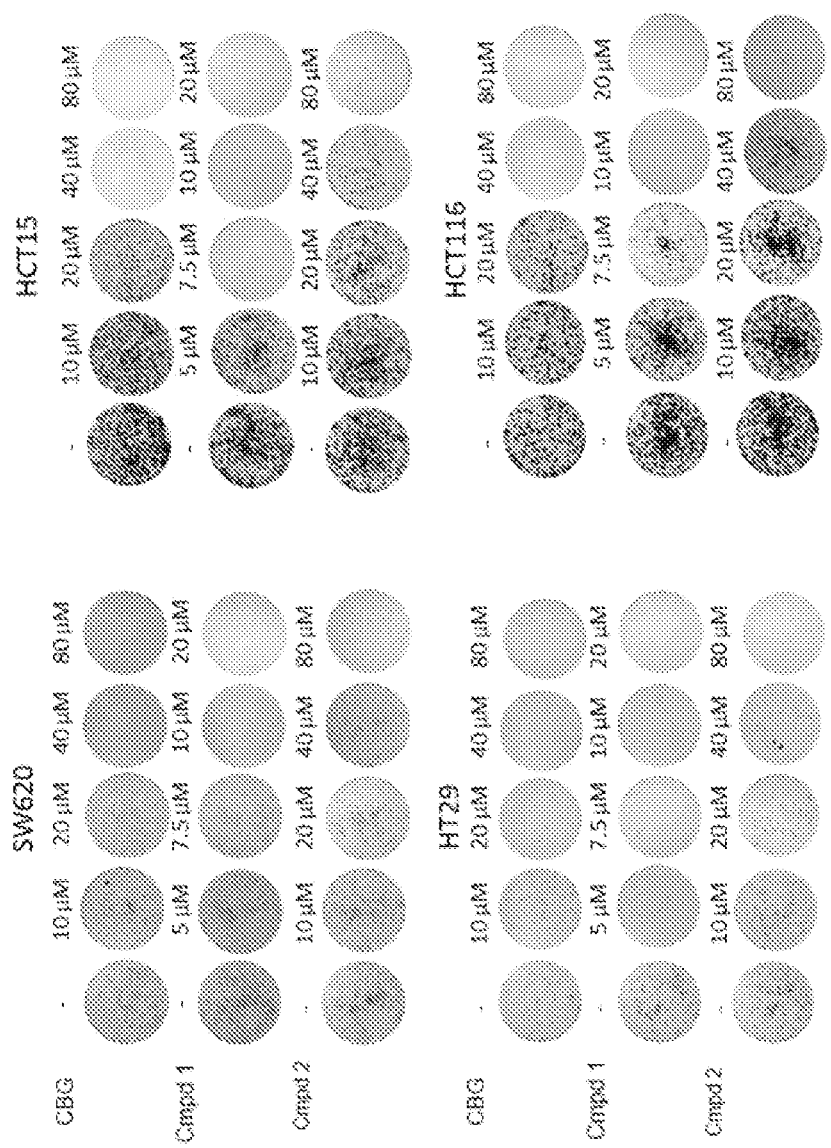
FIG. 26 Clonogenic assay of colon cancer cell lines treated with CBG, Compound 1 and Compound 2. Representative images from three independent experiments.

Measured by clonogenic assay, the $GI_{50}$ of the compound of CBG, Compound 1, and Compound 2 on SW620 cells was 20.58±1.95, 5.35±1.11, and 41.66±5.90 μM respectively; the $GI_{50}$ of the compound of CBG, Compound 1, and Compound 2 on HCT15 cells was 17.40±2.89, 5.03±2.16, and 35.89±8.95 μM respectively; the $GI_{50}$ of the compound of CBG, Compound 1, and Compound 2 on HT29 cells was 9.09±1.71, 2.95±1.41, and 34.47±14.42 μM respectively; the $GI_{50}$ of the compound of CBG, Compound 1, and Compound 2 on HCT116 cells was 17.41±4.91, 5.51±1.51, and 43.06±7.68 μM respectively (FIG. 26 and Table 16).

TABLE 16

$GI_{50}$ (μM) of test compounds measured with clonogenic assay.

| Cell line | Compound | N1 | N2 | N3 | AVG | SD |
|---|---|---|---|---|---|---|
| SW620 | CBG | 18.94 | 22.73 | 20.07 | 20.58 | 1.95 |
| | Cmpd 1 | 5.76 | 4.09 | 6.20 | 5.35 | 1.11 |
| | Cmpd 2 | 47.78 | 41.18 | 36.01 | 41.66 | 5.90 |
| HCT15 | CBG | 15.61 | 20.74 | 15.86 | 17.40 | 2.89 |
| | Cmpd 1 | 3.64 | 7.52 | 3.94 | 5.03 | 2.16 |
| | Cmpd 2 | 46.22 | 30.46 | 31.00 | 35.89 | 8.95 |
| HT29 | CBG | 8.11 | 8.09 | 11.07 | 9.09 | 1.71 |
| | Cmpd 1 | 1.33 | 3.87 | 3.66 | 2.95 | 1.41 |
| | Cmpd 2 | 51.07 | 25.04 | 27.31 | 34.47 | 14.42 |
| HCT116 | CBG | 21.07 | 20.68 | 10.47 | 17.41 | 4.91 |
| | Cmpd 1 | 4.79 | 7.61 | 4.12 | 5.51 | 1.51 |
| | Cmpd 2 | 53.44 | 40.65 | 35.10 | 43.06 | 7.68 |

Conclusion

Figure 27A:
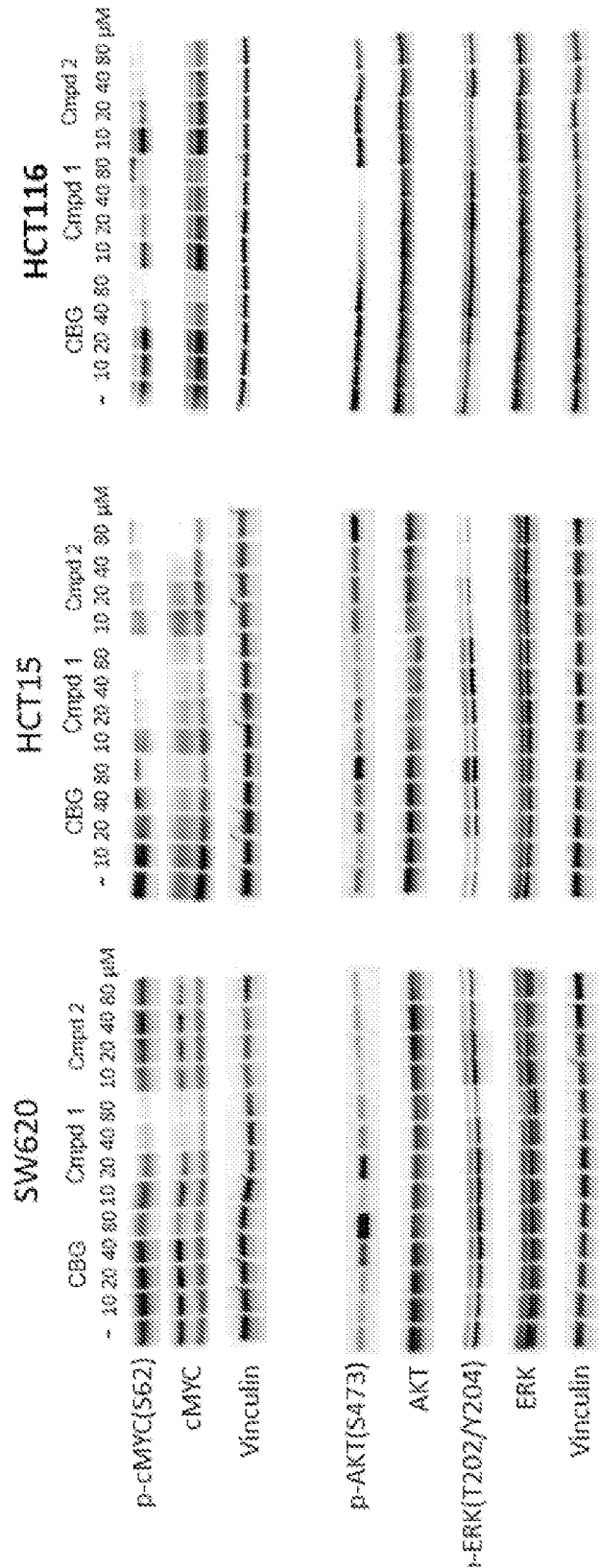
FIG. 27A, FIG. 27B, FIG. 27C, and FIG. 27D show Western blot for p-cMyc(S62), cMyc, p-AKT(S473), AKT, p-ERK(T202/Y204), and ERK normalized to Vinculin in SW620, HCT15, and HCT116 cells treated with CBG, Compound 1, and Compound 2 at indicated concentrations for 3 hours.
Figure 27B:
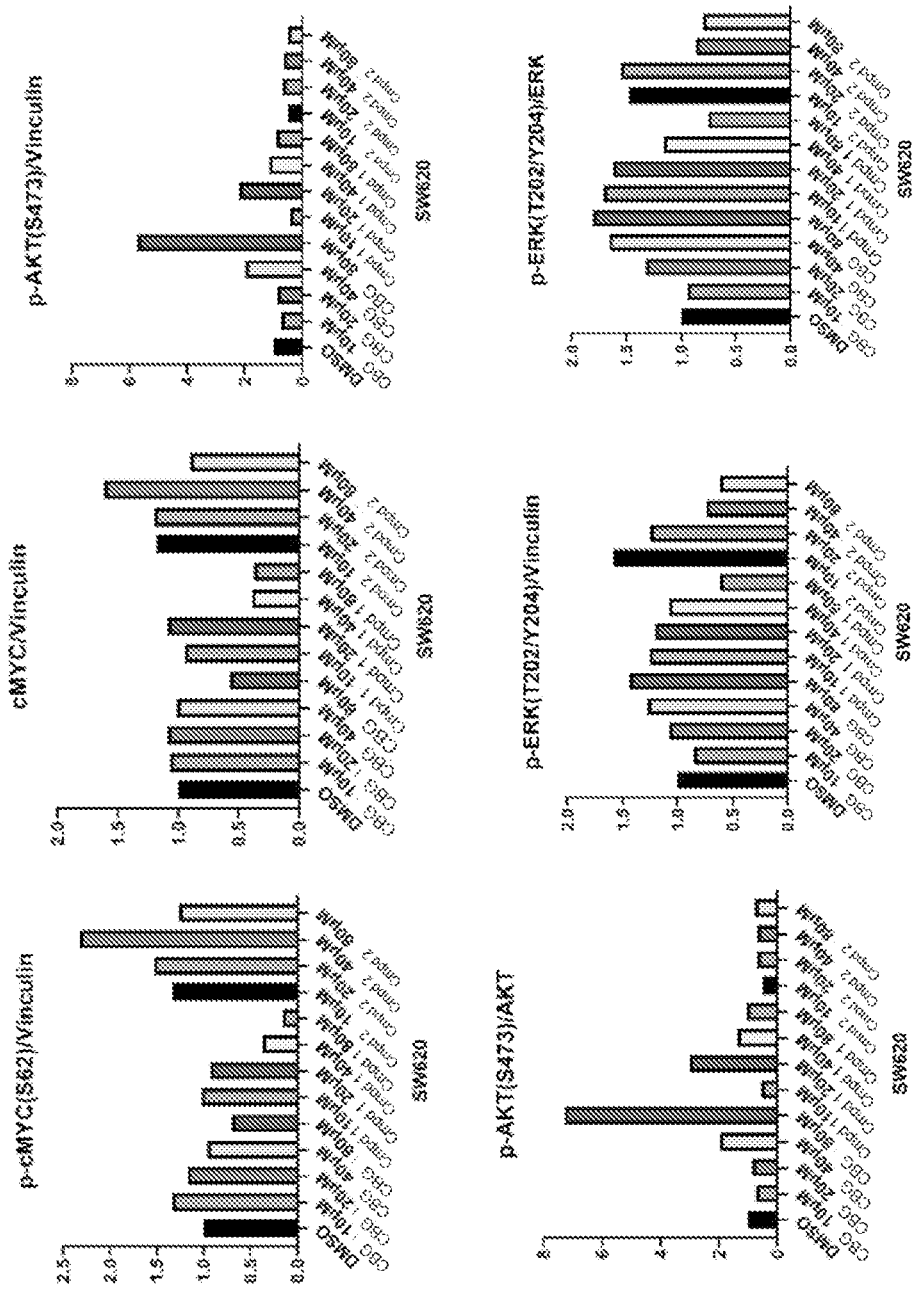
Figure 27C:
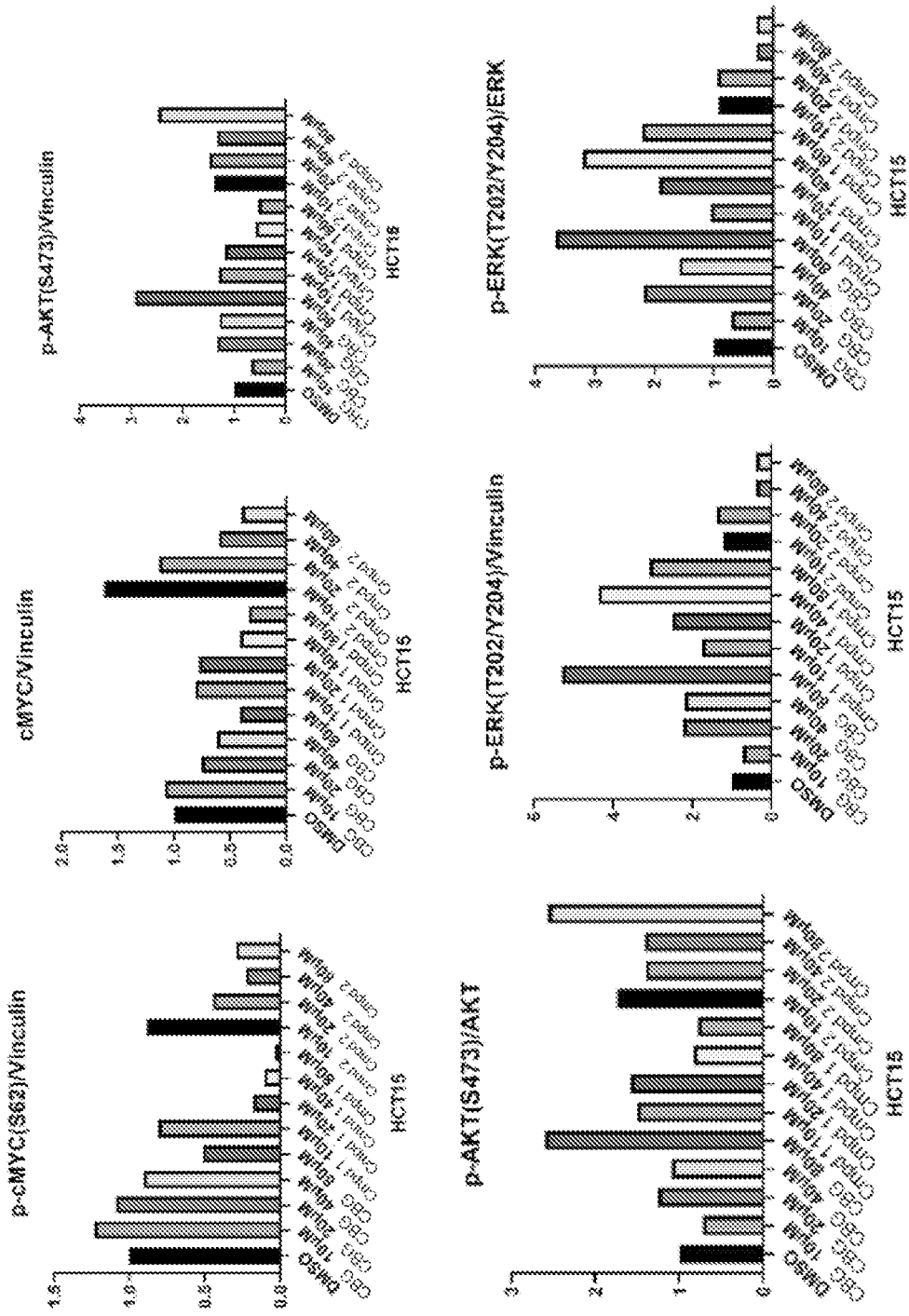
Figure 27D:
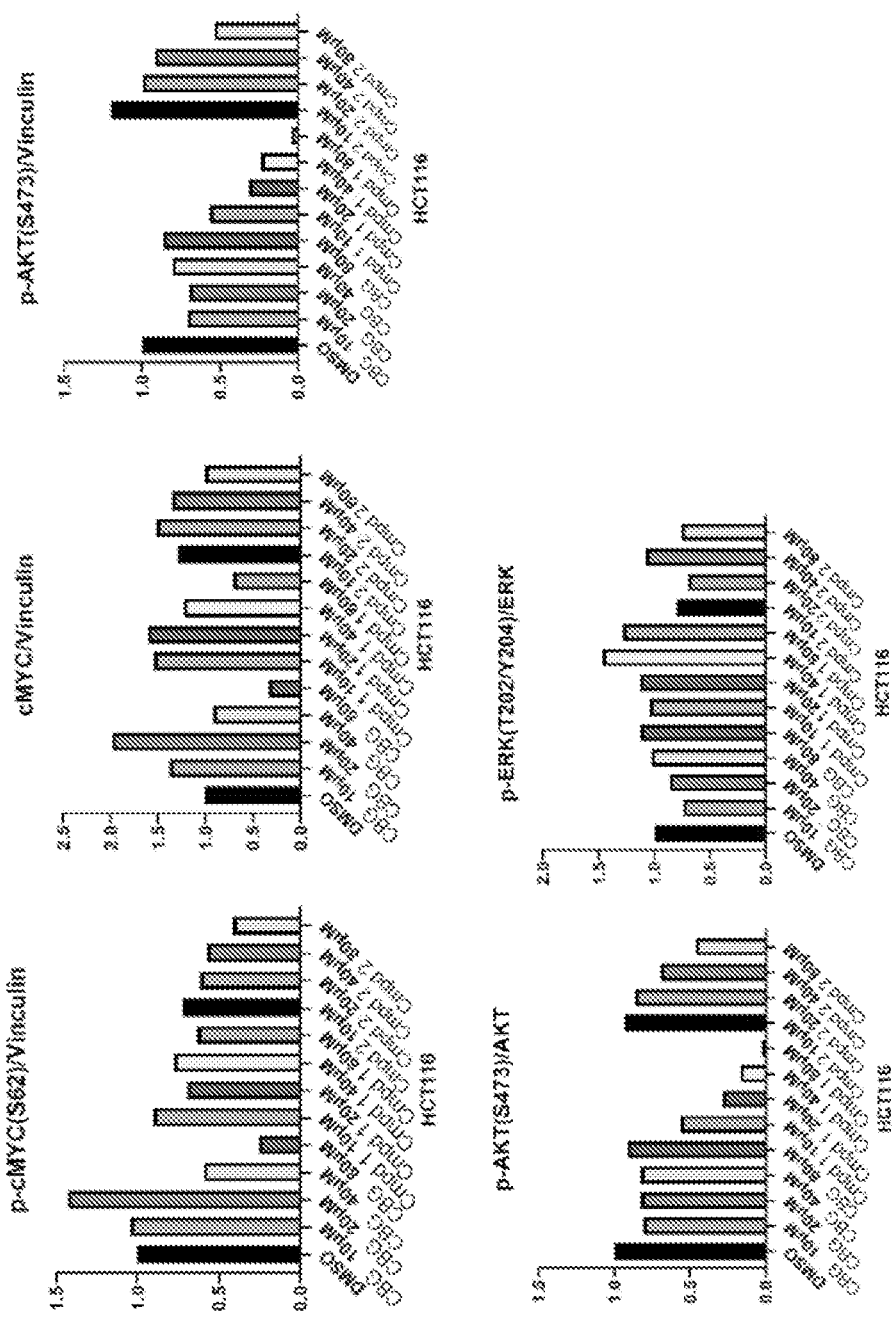

Among the three compounds, Compound 1 showed the most potent effect on colon cancer cell viability with the lowest $GI_{50}$ measured. Compounds of the disclosure down-regulated the expression of p-cMyc(S62) and cMyc in dose-dependent manner in all three colon cancer cell lines examined (FIGS. 27A-D). Compound 1 down-regulated pAKT(S473) in HCT116 cells with a dose effect (FIG. 27D).

Example 9. Study of CBD and CBD Derivative in a PTZ-Induced Epilepsy Mouse Model Other compounds of the present disclosure (e.g., one or more compounds of Formula (I), (II), (III), Table 1 or Table 2) may also be evaluated in this assay.

Introduction and Background

Mouse models using $GABA_a$ receptor antagonist Pentylenetetrazol (PTZ) are well defined and used as a standard for the identification of potential anticonvulsants to treat generalized clonic seizures (Loscher et al., 1991 Epilepsy Res 8:171-189). The purpose of this study was to evaluate and compare CBD to test article Compound 3, on their therapeutic effects in a mouse model of PTZ-induced seizure. To match up test article plasma concentration time max (Tmax) with the PTZ induced seizures; test articles were administered at 60 minutes and 30 minutes prior to PTZ administration respectively. Vehicle used for treatment groups was 10% EtOH/10% Tween 80/80% Saline.

Abbreviations Used

IP: Intraperitoneal route of administration
mg/kg: Milligrams/kilogram
mpk: Milligrams/kilogram
mg/mL: Milligrams/milliliter
mL/kg: Milliliters/kilogram
PTZ: Pentylenetetrazol
SEM: Standard error of the mean
T0: Time of PTZ administration
Study Design Table

| GROUP # | TREAT-MENT | GROUP SIZE | PTZ | PRE-TREAT | DOSE | ROUTE | EVALUATIONS/END-POINTS |
|---|---|---|---|---|---|---|---|
| 1 | Sham (Vehicle/Vehicle) | 5 | N/A | T0 | N/A | IP | Modified Racine scale for seizure severity Measure % tonic-clonic mortality Terminal blood collection |
| 2 | Vehicle/PTZ | 10 | 80 mg/kg | T0 | NA | | |
| 3 | CBD/PTZ | | | 60 min pre-PTZ | 100 mg/kg | | |
| 4 | Compd 3/PTZ | | | 30 min pre-PTZ | 100 mg/kg | | |

PTZ Model

Mice were acclimated to the procedure room for at least 30 minutes.

Pentylenetetrazole (PTZ; Sigma Aldrich) was formulated in water to a concentration of 16 mg/mL. Injections of PTZ were made at a volume of 5 mL/kg to produce a final dose of 80 mg/kg. Immediately following PTZ administration, animals were observed in real-time for 30 minutes and latency of clonic and tonic hindlimb extensor responses was recorded, as well as modified Racine Scale scoring.

Modified Racine Scale Scoring

Following PTZ administration, animals were observed for
  30 mins where time to initial
seizure sign, time to clonic, and time to tonic hindlimb
  seizure were recorded. A 30-
minute maximum latency to seizure was imposed.
Clinical behavior was scored using the following adapted
  Racine scale:
Score 0, no seizures observed
Score 1, Behavioral arrest (freezing, fixed gaze, staring),
  vibrissae twitching,
mouth or facial clonus
Score 2, Pop or jump, straub tail, foot splay, head nodding
Score 3, Forelimb clonus, extended forelimbs, multiple
  pops or jerks
Score 4, Rearing and bilateral forelimb clonus, Running
  and running/bouncing
Score 5, All limb clonus, rearing and falling (stay fallen
  on rear side)
Score 6, Tonic hindlimb extensions, cardiac arrest Behavior was scored by an observer blind to treatment. The highest score reached during every 5 minute period during the 30 minutes after PTZ was administered was recorded. Additionally, the percent tonic-clonic (number of animals progressing to the highest seizure score), and percent mortality was also calculated.

Results

Figure 28:
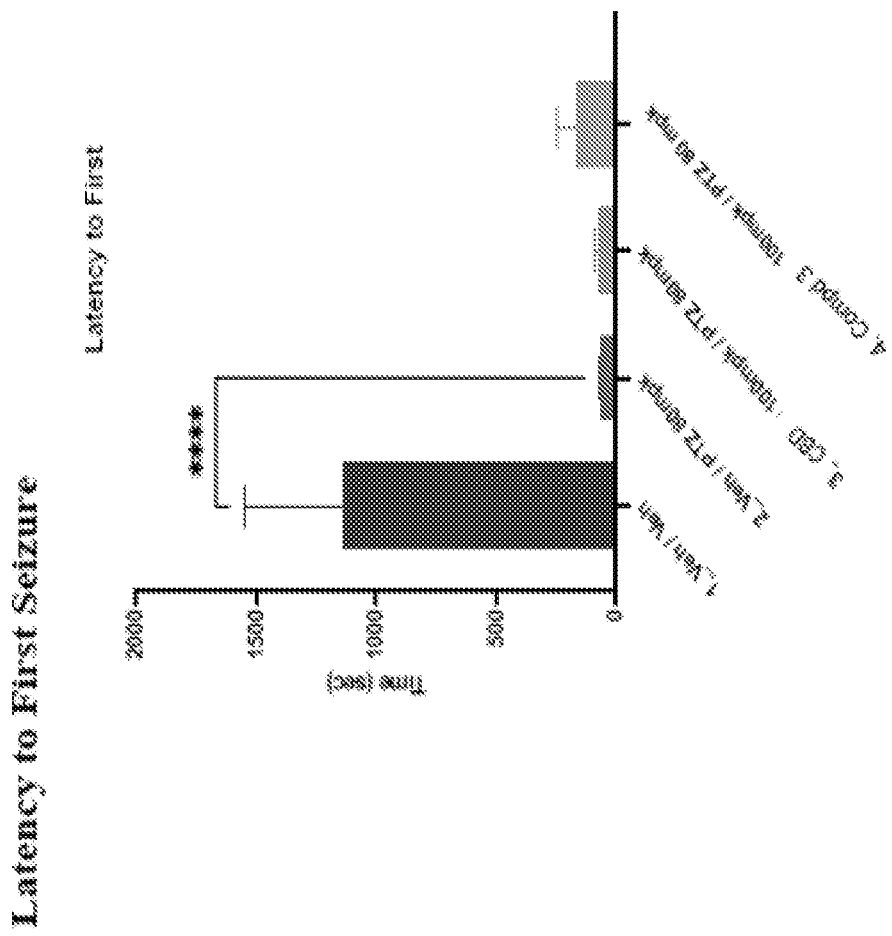
FIG. 28 is a graph showing latency to First Seizure Event in the study described in Example 9.
Figure 29:
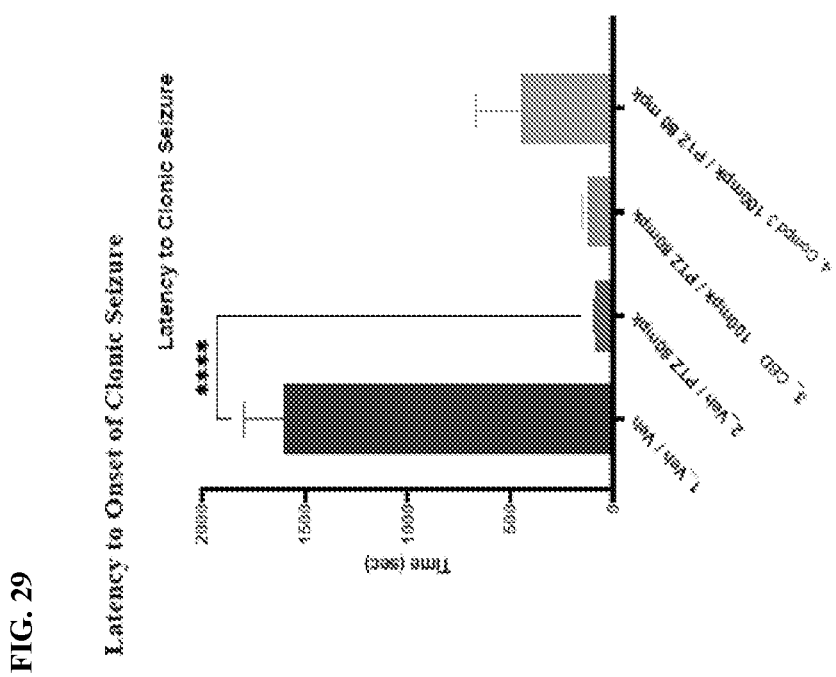
FIG. 29 is a graph showing latency to Clonic Seizure Event in the study described in Example 9.

FIG. 28. Latency to First Seizure Event. The time to the first seizure event was recorded. PTZ yielded a significant decrease in latency to the first seizure compared to the vehicle/vehicle group ($p \leq 0.0001$). Data are presented as means±SEM (n=10 except Veh/Veh n=5). Statistical analysis was by Fisher's LSD test compared to Veh/PTZ group. **$p \leq 0.0001$ FIG. 29. Latency to Clonic Seizure Event. The time to the first clonic seizure event was recorded. PTZ yielded a significant decrease in latency to the first clonic seizure compared to the vehicle/vehicle group (p≤0.0001). Data are presented as means±SEM (n=10 except Veh/Veh n=5). Statistical analysis was by Fisher's LSD test compared to Veh/PTZ group. **p≤00.0001

Figure 30:
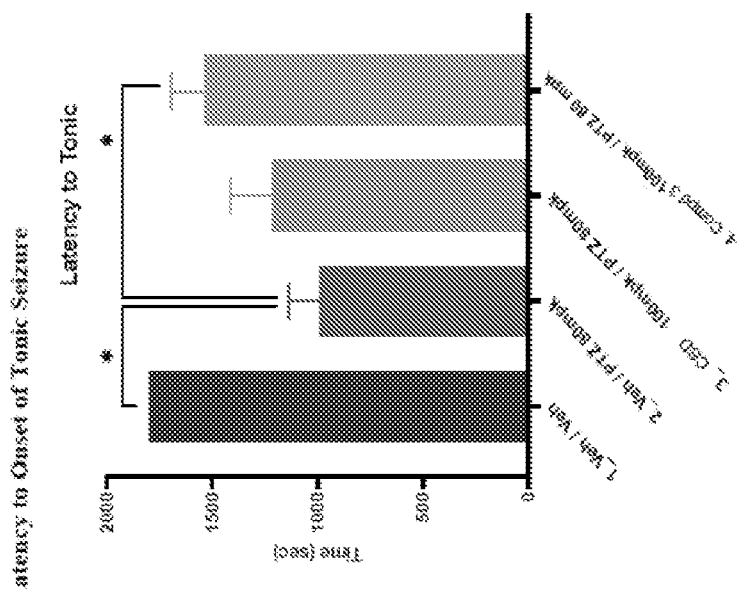
FIG. 30. is a graph showing latency to Tonic Seizure Event in the study described in Example 9.

FIG. 30. Latency to Tonic Seizure Event. The time to the first tonic seizure event was recorded. PTZ yielded a significant decrease in latency to the first tonic seizure compared to the vehicle/vehicle group (p≤0.05). Administration of CBD prior to PTZ did not yield a significantly different latency compared to PTZ alone. However, administration of Compound 3 prior to PTZ (100 mg/kg; 30 minutes prior to PTZ) did yield a significantly longer latency compared to PTZ alone p≤0.05). Data are presented as means±SEM (n=10 except Veh/Veh n=5). Statistical analysis was by Fisher's LSD test compared to Veh/PTZ group. *p≤0.05

FIG. 31 Racine scores over 5 minute intervals for 30 minutes. Following PTZ administration clinical scores (Racine scores) were recorded for each animal every 5 minutes over a 30 minute period. Compared to the vehicle/vehicle group, administration of PTZ (Veh/PTZ group) yielded an immediate and sustained significant increase in clinical score over the entire 30 minute period. (p≤0.0001). CBD (100 mg/kg; 60 minutes prior to PTZ) did not yield a significant change in clinical score compared to PTZ alone. Compound 3 (100 mg/kg; 30 minutes prior to PTZ) exhibited a significant improvement in Racine scores beginning at the 10 minute time point (p≤0.01) with this effect size maintained through to 25 minutes and improving at 30 minutes (p≤0.001). Data are presented as means±SEM (n=10). Statistical analysis was by Fisher's LSD test compared to Veh/PTZ group. p≤0.01, *p≤0.001, ****p≤0.0001

Figure 32:
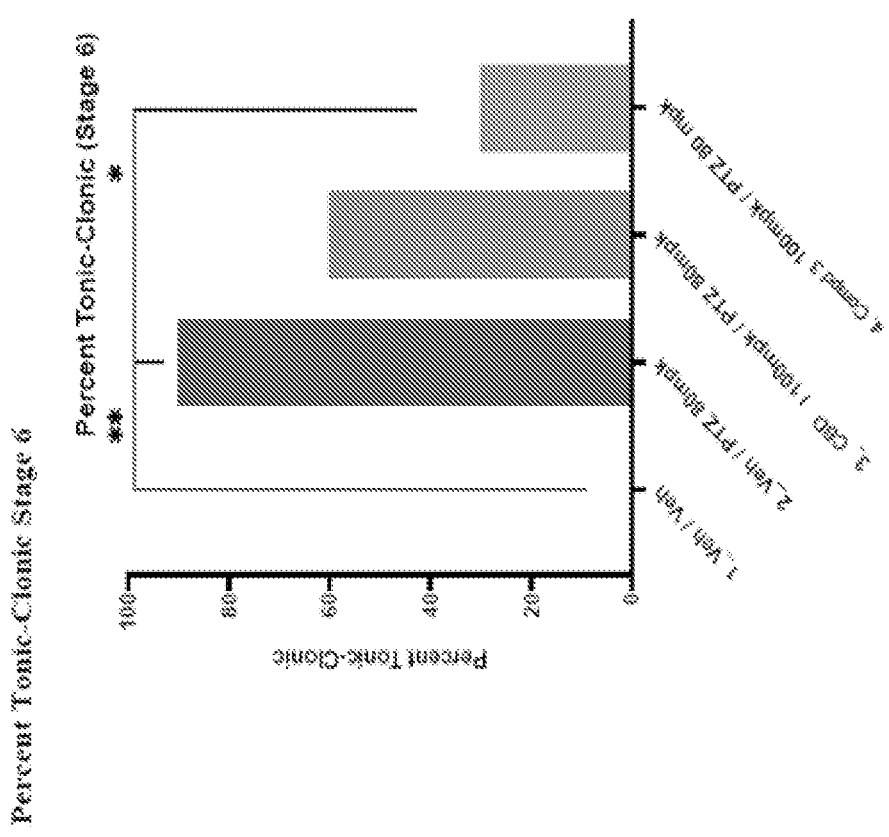
FIG. 32 is a graph showing percent of animals reaching Tonic-clonic Stage 6 in the study described in Example 9.

FIG. 32 Percent of animals reaching Tonic-clonic Stage 6. The proportion of animals in each treatment group which reached tonic-clonic Stage 6 was recorded. PTZ yielded a significant increase in proportion of animals reaching Stage 6 compared to the vehicle/vehicle group (p≤0.01). Administration of CBD prior to PTZ did not yield a significantly difference in proportion compared to PTZ alone. However, administration of Compound 3 prior to PTZ (100 mg/kg; 30 minutes prior to PTZ) did yield a significantly lower proportion compared to PTZ alone p≤0.05). Data are presented as means±SEM (n=10 except Veh/Veh n=5). Statistical analysis was by Fisher's LSD test compared to Veh/PTZ group. *p≤0.05, **p≤0.01

FIG. 33 Survival Effects. During the 30 minute observation period following PTZ administration any deaths that occurred were noted and the time to death was recorded. No deaths occurred among 5 animals receiving vehicle/vehicle compared to 9/10 deaths among vehicle/PTZ animals (p≤0.01). Compared to the vehicle/PTZ group, administration of CBD prior to PTZ did not yield a significantly reduced mortality rate. Administration of Compound 3 (100 mg/kg; 30 minutes prior to PTZ) did result in a significantly reduced mortality rate compared to the vehicle/PTZ group (p≤0.01). Data are presented as means:SEM (n=10 except vehicle/vehicle n=5). Statistical analysis was by Fisher's LSD test compared to Veh/PTZ group. **p≤0.01.

Summary of the Results

Latency to First Seizure Event.

PTZ yielded a significant decrease in latency to the first seizure event compared to the vehicle/vehicle group (p≤0.0001).

As expected, administration of CBD did not result in a difference in latency to first seizure compared to PTZ alone (Jones et al (2010) *J. Pharmacology and Experimental Therapeutics*. Vol. 332, No. 2). However, Compound 3 trended towards a longer latency than PTZ alone, although the difference was not significant.

Latency to Clonic Seizure Event.

PTZ yielded a significant decrease in latency to the first clonic seizure compared to the vehicle/vehicle group (p≤0.0001).

Administration of CBD or Compound 3 prior to PTZ did not yield a significantly different latency compared to PTZ alone. However, Compound 3 had a strong trend toward longer latency for this score.

Latency to Tonic Seizure Event.

PTZ yielded a significant decrease in latency to the first tonic seizure compared to the vehicle/vehicle group (p≤0.05).

Administration of CBD prior to PTZ did not yield a significantly different latency compared to PTZ alone.

Administration of Compound 3 prior to PTZ (100 mg/kg; 30 minutes prior to PTZ) did yield a significantly longer latency compared to PTZ alone p≤0.05).

Racine Scores

PTZ yielded an immediate and sustained significant increase in clinical score over the entire 30 minute period compared to the vehicle/vehicle group. (p≤0.0001).

CBD (100 mg/kg; 60 minutes prior to PTZ) did not yield a significant change in clinical score compared to PTZ alone.

Compound 3 (100 mg/kg; 30 minutes prior to PTZ) exhibited a significant improvement in Racine scores beginning at the 10 minute time point (p≤0.01) with this effect size maintained through to 25 minutes and improving at 30 minutes (p≤0.001).

Percent of Animals Reaching Tonic-Clonic Stage 6.

PTZ yielded a significant increase in proportion of animals reaching Stage 6 compared to the vehicle/vehicle group (p≤0.01).

Administration of CBD prior to PTZ did not yield a significant difference in proportion compared to PTZ alone.

Administration of Compound 3 prior to PTZ (100 mg/kg; 30 minutes prior to PTZ) yielded a significantly lower proportion compared to PTZ alone p≤0.05).

Survival Effects.

PTZ administration resulted in a significant increase in the proportion of animals that died within 30 minutes following administration (p≤0.01).

CBD prior to PTZ did not yield a significantly reduced mortality rate compared to the vehicle/PTZ group.

Compound 3 (100 mg/kg; 30 minutes prior to PTZ) resulted in a significantly reduced mortality rate compared to the vehicle/PTZ group (p≤0.01)

In summary, Compound 3 demonstrated clear anti-epileptic therapeutic activity and outperform CBD (CBD) an FDA approved drug for the treatment of epilepsy disorders (Epidiolex®) in a gold standard PTZ seizure model.

Example 10. Synthesis of (E)-2-(3,7-dimethylocta-2,6-dien-1-yl)-3-ethoxy-5-pentylphenol (Compound 4) and (E)-2-(3,7-dimethylocta-2,6-dien-1-yl)-1,3-diethoxy-5-pentylbenzene (Compound 5)

Example 11. Synthesis of (E)-2-(3,7-dimethylocta-2,6-dien-1-yl)-5-pentyl-3-propoxyphenol (Compound 6) and (E)-2-(3,7-dimethylocta-2,6-dien-1-yl)-5-pentyl-1,3-dipropoxybenzene (Compound 7)

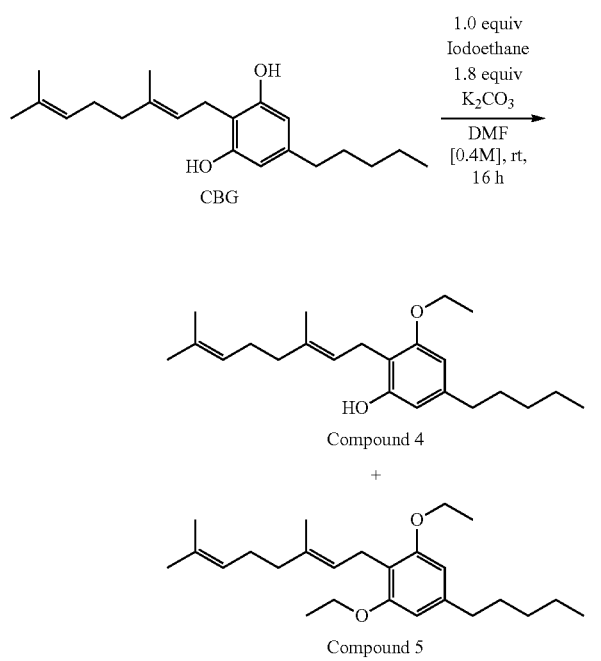

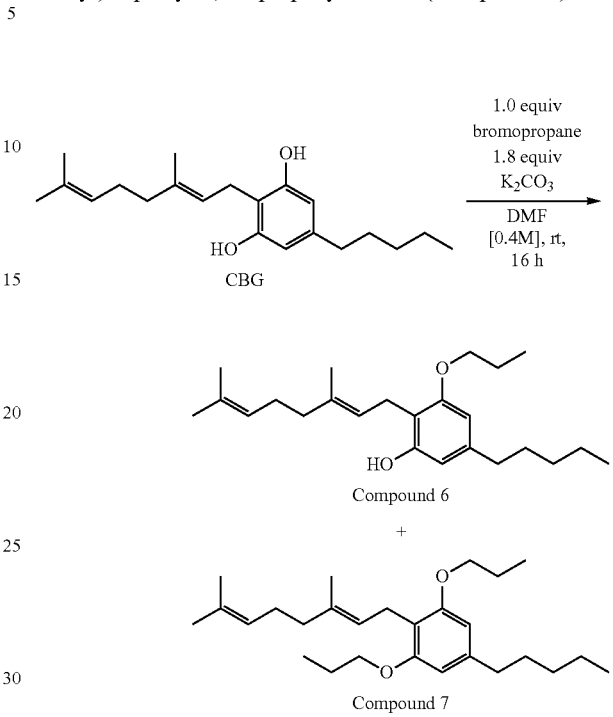

A 250 mL single neck round bottom flask was charged with CBG (8.0 g, 25 mmol), DMF (60 mL), pulverized K₂CO₃ (6.3 g; 46 mmol) and were stirred at room temperature for 15 minutes. To this solution ethyl iodide (3.9 g; 25 mmol) was added, the reaction mixture was stirred at room temperature for 16 h. The reaction was monitored by TLC (5% ethyl acetate in heptane). Two scoops of Celite were added into the reaction mixture and stirred for 10 min before the resultant mixture was filtered through a short plug of celite to remove all the insoluble. The celite bed was washed with ethyl acetate (100 mL×3) for maximum recovery. The resultant organic layer was washed with water (100 mL×5), followed by a brine wash (50 mL×2). The organic solvent was dried over Na₂SO₄ and was concentrated to receive 8.92 g of dark brown oil. The crude oil was purified by automated flash chromatography using Teledyne ISCO. Elution with just heptane afforded pure Compound 5(1.7 g, 4.6 mmol, 18% yield) as colorless oil, purity>95% by ¹H-NMR. Further elution with 0-1-% ethyl acetate in heptane provided Compound 4 (1.7 g, 4.8 mmol, 20% yield) as orange oil, purity>95% by ¹H-NMR.

Compound 4: ¹H NMR (300 MHz, CDCl₃): δ ppm 0.89 (t, J=7.12 Hz, 3H), 1.31-1.41 (m, 7H), 1.58 (s, 3H), 1.66 (s, 3H), 1.78 (s, 3H), 2.02-2.09 (m, 4H), 2.51 (t, J=7.50 Hz, 2H), 3.41 (d, J=7.20 Hz, 2H), 4.0 (q, J=7.20 Hz, 2H), 5.05 (t, J=6.30 Hz, 1H), 5.26 (m, 2H), 6.29 (d, J=6.30 Hz, 2H).

Compound 5: ¹H NMR (300 MHz, CDCl₃): δ ppm 0.93 (t, J=7.20 Hz, 3H), 1.33-1.45 (m, 9H), 1.61-1.68 (m, 8H), 1.81 (s, 3H), 1.98-2.11 (m, 4H), 2.56 (t, J=7.65 Hz, 2H), 3.38 (d, J=7.80 Hz, 2H), 4.04 (q, J=6.9 Hz, 4H), 5.12 (t, J=6.90, 1H), 5.28 (t, J=6.90 Hz, 1H), 6.37 (s, 2H).

A 200 mL single neck round bottom flask was charged with CBG (8.0 g, 25 mmol), DMF (60 mL), pulverized K₂CO₃ (6.3 g; 46 mmol) and were stirred at room temperature for 15 minutes. To this solution 1-bromopropane (3.1 g; 25 mmol) was added, the reaction mixture was stirred at room temperature for 16 h. The reaction was monitored by TLC (5% ethyl acetate in heptane). The reaction mixture was filtered through a pad of celite to remove all the insoluble. The celite bed was washed with ethyl acetate (100 mL×3) for maximum recovery. The resultant organic layer was washed with water (100 mL×5), followed by a brine wash (50 mL×2). The organic solvent was dried over Na₂SO₄ and was concentrated to a crude brown oil. The crude oil was purified by automated flash chromatography using Teledyne ISCO. Elution with just EtOAc/heptane (0-1%) afforded pure Compound 6 (1.7 g, 18% yield) as a light yellow oil, purity >95% by ¹H-NMR and Compound 7 (2.0 g, 19% yield) as a colorless oil, purity>95% by ¹H-NMR.

Compound 6: ¹H NMR (300 MHz, CDCl₃): δ ppm 0.88 (t, J=7.12 Hz, 3H), 1.04 (t, J=7.20 Hz, 3H), 1.29-1.34 (m, 4H), 1.51-1.84 (m, 4H), 1.58 (s, 3H), 1.66 (s, 3H), 1.80 (s, 3H), 2.02-2.09 (m, 4H), 2.46 (t, J=7.35 Hz, 2H), 3.39 (d, J=7.2 Hz, 2H), 3.89 (t, J=6.3 Hz, 2H), 5.05 (t, J=8.85 Hz, 1H), 5.21 (s, OH), 5.25 (t, J=6.45 Hz, 1H), 6.28 (s, 1H), 6.30 (s, 1H)

Compound 7: ¹H NMR (300 MHz, CDCl₃): δ ppm 0.90 (t, J=7.05 Hz, 3H), 1.05 (t, J=7.35 Hz, 6H), 1.31-1.37 (m, 4H), 1.56-1.86 (m, 6H), 1.57 (s, 3H), 1.65 (s, 3H), 1.77 (s, 3H), 1.92-2.07 (m, 4H), 2.54 (t, J=7.80 Hz, 2H), 3.36 (d, J=6.90 Hz, 2H), 3.91 (t, J=6.45 Hz, 4H), 5.09 (t, J=6.50 Hz, 1H), 5.25 (t, J=6.45 Hz, 1H), 6.34 (s, 2H).

Example 12. Synthesis of (E)-3-butoxy-2-(3,7-dimethylocta-2,6-dien-1-yl)-5-pentylphenol (Compound 8) and (E)-1,3-dibutoxy-2-(3,7-dimethylocta-2,6-dien-1-yl)-5-pentylbenzene Example 13. Synthesis of (E)-3-(allyloxy)-2-(3,7-dimethylocta-2,6-dien-1-yl)-5-pentylphenol (Compound 10) and (E)-1,3-bis(allyloxy)-2-(3,7-dimethylocta-2,6-dien-1-yl)-5-pentylbenzene (Compound 11)

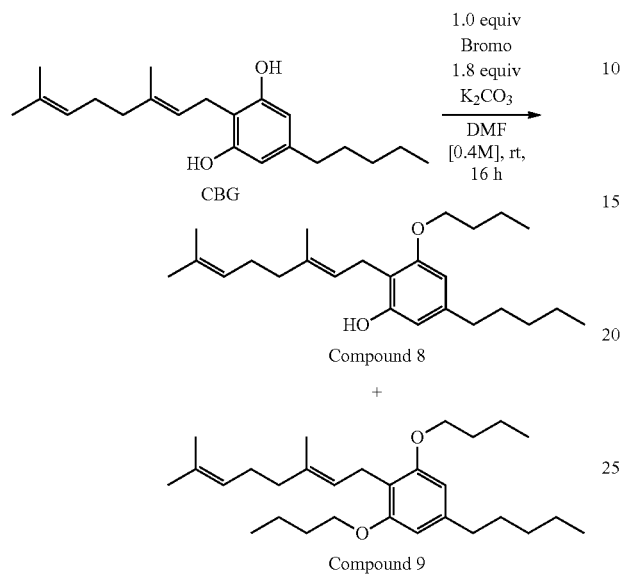

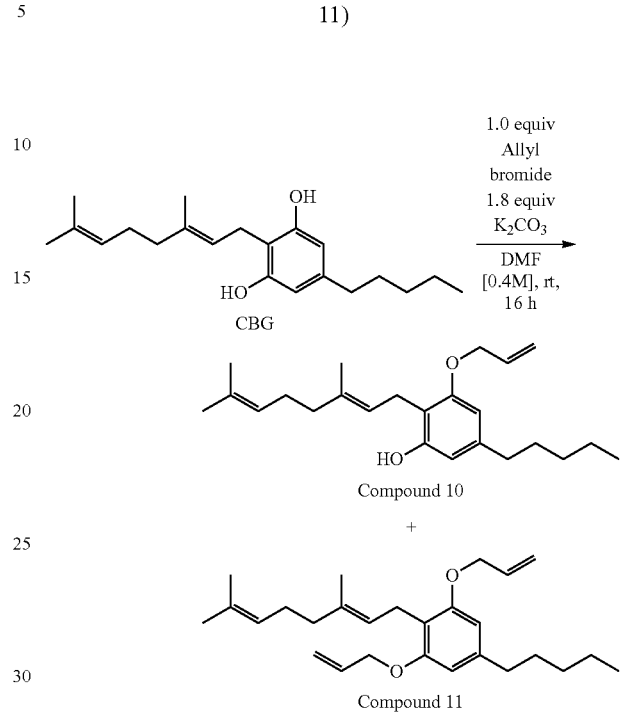

A 250 mL single neck round bottom flask was charged with CBG (10.0 g, 31.6 mmol), DMF (100 mL), pulverized K$_2$CO$_3$ (7.86 g; 56.9 mmol) and were stirred at room temperature for 15 minutes. To this solution Bromobutane (4.33 g, 31.6 mmol) was added, the reaction mixture was stirred at room temperature for 24 h. The reaction was monitored by TLC (5% ethyl acetate in heptane). Celite were added into the reaction mixture and stirred for 10 min before the resultant mixture was filtered through a short plug of celite to remove all the insoluble. The celite bed was washed with ethyl acetate (200 mL×2) for maximum recovery. The resultant organic layer was washed with water (200 mL×4), followed by a brine wash (100 mL×2). The organic solvent was dried over anh. Na$_2$SO$_4$ and was concentrated to receive 12.5 g of dark brown oil. The crude oil was purified by automated flash chromatography using Teledyne ISCO. Elution with just heptane afforded pure Compound 9 (1.2 g, 16% yield) as colorless oil, purity>95% by $^1$H-NMR. Further elution with 0-1-% ethyl acetate in heptane provided Compound 8, it needed further purification. One more column purification was attempted with 0-1-% ethyl acetate in heptane provided Compound 8 (1.0 g, 10% yield) as light brown oil, purity 93% by $^1$H-NMR.

Compound 8: $^1$H NMR (300 MHz, CDCl$_3$): δ ppm 0.89 (t, J=4.65 Hz, 3H), 0.97 (t, J=7.2 Hz, 3H), 1.29-1.37 (m, 4H), 1.44-1.65 (m, 6H), 1.67 (s, 3H), 1.71-1.80 (m, 6H), 2.01-2.10 (m, 4H), 2.50 (t, J=7.65 Hz, 2H), 3.40 (d, J=6.9 Hz, 2H), 3.94 (t, J=6.45 Hz, 2H), 5.06 (t, J=6.15 Hz, 1H), 5.21 (s, OH), 5.25 (t, J=7.2 Hz, 1H), 6.30 (s, 1H), 6.31 (s, 1H)

Compound 9: $^1$H NMR (300 MHz, CDCl$_3$): δ ppm 0.91 (t, J=5.25 Hz, 3H), 0.97 (t, J=7.35 Hz, 6H), 1.31-1.36 (m, 4H), 1.45-1.63 (m, 8H), 1.66 (s, 3H), 1.72-1.81 (m, 8H), 1.92-2.07 (m, 4H), 2.54 (t, J=7.5 Hz, 2H), 3.35 (d, J=6.9 Hz, 2H), 3.95 (t, J=6.15 Hz, 4H), 5.09 (t, J=7.05 Hz, 1H), 5.24 (t, J=7.05 Hz, 1H), 5.34 (s, 2H)

A 250 mL single neck round bottom flask was charged with CBG (8.0 g, 25 mmol), DMF (60 mL), pulverized K$_2$CO$_3$ (6.3 g; 46 mmol) and were stirred at room temperature for 15 minutes. To this solution allyl bromide (3.1 g, 2.2 mL, 25 mmol) was added, the reaction mixture was stirred at room temperature for 16 h. The reaction was monitored by TLC (5% ethyl acetate in heptane). Two scoops of Celite were added into the reaction mixture and stirred for 10 min before the resultant mixture was filtered through a short plug of celite to remove all the insoluble. The celite bed was washed with ethyl acetate (100 mL×3) for maximum recovery. The resultant organic layer was washed with water (100 mL×5), followed by a brine wash (50 mL×2). The organic solvent was dried over anh. Na$_2$SO$_4$ and was concentrated to receive 9.03 g of dark brown oil. The crude oil was purified by automated flash chromatography using Teledyne ISCO. Elution with just heptane afforded pure Compound 11 (2.3 g, 5.8 mmol, 23% yield) as colorless oil, purity >98% by $^1$H-NMR. Further elution with 0-1-% ethyl acetate in heptane provided Compound 10, it needed further purification. One more column purification was attempted with 0-1-% ethyl acetate in heptane provided Compound 10 (1.75 g, 4.9 mmol, 19% yield) as orange oil, purity 90% by $^1$H-NMR.

Compound 10: $^1$H NMR (300 MHz, CDCl$_3$): δ ppm 0.89 (t, J=4.8 Hz, 3H), 1.25-1.35 (m, 6H), 1.52-1.67 (m, 12H), 1.66 (s, 3H), 1.79 (s, 3H), 2.01-2.10 (m, 4H), 2.50 (dd, J=7.50 Hz, 2H), 3.41 (d, J=6.90 Hz, 2H), 4.51 (q, J=5.40 Hz, 2H), 5.07 (m, 1H), 5.23-5.28 (m, 3H), 5.36-5.44 (m, 1H), 5.99-6.1 (m, 1H), 6.30 (s, 1H), 6.33 (s, 1H)

Compound 11: $^1$H NMR (300 MHz, CDCl$_3$): δ ppm 0.89 (t, J=7.20 Hz, 3H), 1.30-1.40 (m, 4H), 1.51-1.67 (m, 10H), 1.80 (s, 3H), 1.95-2.08 (m, 4H), 2.56 (t, J=7.65 Hz, 2H), 3.38 (d, J=7.80 Hz, 2H), 4.51 (q, J=6.9 Hz, 4H), 5.06-5.10 (m, 2H), 5.22-5.30 (m, 2H), 5.41-5.48 (m, 2H), 5.98-6.10 (m, 2H), 6.37 (s, 2H).

Example 14. Synthesis of (E)-2-(3,7-dimethylocta-2,6-dien-1-yl)-3-(2-hydroxyethoxy)-5-pentylphenol (Compound 12) and (E)-2,2'-((2-(3,7-dimethylocta-2,6-dien-1-yl)-5-pentyl-1,3-phenylene)bis(oxy))bis(ethan-1-ol) (Compound 13)

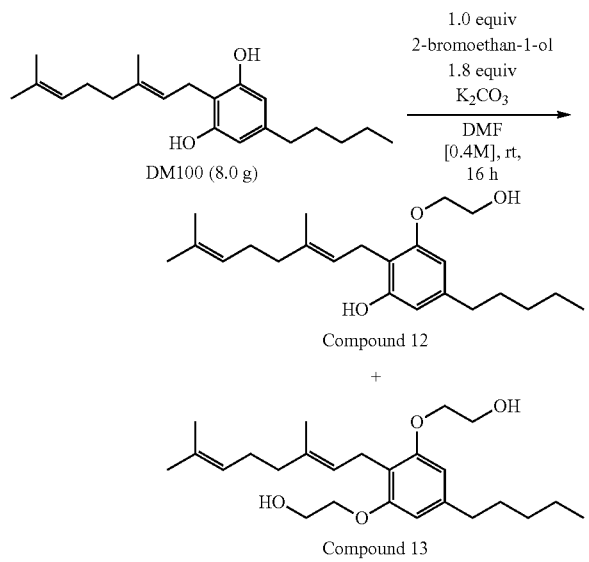

A 200 mL single neck round bottom flask was charged with CBG (10.0 g, 31.6 mmol), DMF (100 mL), pulverized K$_2$CO$_3$ (7.86 g; 56.9 mmol) and were stirred at room temperature for 15 minutes. To this solution 2-bromethan-1-ol (3.91 g, 2.2 mL, 31.6 mmol) was added, the reaction mixture was stirred at room temperature for 16 h. The reaction was monitored by TLC (20% ethyl acetate in heptane), which indicates the predominance of unreacted starting material. The reaction was then heated to 120° C. for an additional 16 hours. TLC analysis again shows incomplete conversion to the desired products. Additional K$_2$CO$_3$ (2.18 g, 15.8 mmol) and 2-bromethan-1-ol (1.97 g, 15.8 mmol) were added to the reaction, which was stirred for an additional 16 hours at 120° C. The reaction was cooled and the resultant mixture was filtered through a short plug of celite to remove all the insoluble material. The celite bed was washed with ethyl acetate (100 mL×3) for maximum recovery. The resultant organic layer was washed with water (100 mL×5), followed by a brine wash (50 mL×2). The organic solvent was dried over anhydrous Na$_2$SO$_4$ and was concentrated to yield approximately 10 grams of a dark brown oil. The crude oil was purified by automated flash chromatography using Teledyne ISCO, eluting with 0-20% EtOAc/heptane to furnish as light orange solid Compound 12 (1.25 g, 3.3 mmol, 10% yield), purity>95% by $^1$H-NMR and as a dark brown oil Compound 13 (0.75 g, 1.8 mmol, 5.6% yield), purity>95% by $^1$H-NMR Compound 12: $^1$H NMR (300 MHz, CDCl$_3$): δ ppm 0.89 (t, J=7.05 Hz, 3H), 1.28-1.34 (m, 4H), 1.53-1.59 (m, 5H), 1.67 (s, 3H), 1.80 (s, 3H), 2.00-2.10 (m, 4H), 2.50 (t, J=7.95 Hz, 2H), 3.39 (d, J=7.20 Hz, 2H), 3.92-3.97 (m, 2H), 4.07 (t, J=4.35 Hz, 2H), 5.05 (t, J=6.3 Hz, 1H), 5.21 (s, OH), 5.22 (t, J=6.0 Hz, 1H), 6.31 (s, 1H), 6.34 (s, 1H).

Compound 13: $^1$H NMR (300 MHz, CDCl$_3$): δ ppm 0.90 (t, J=6.75 Hz, 3H), 1.26-1.37 (m, 4H), 1.55-1.64 (m, 8H), 1.78 (s, 3H), 1.94-2.11 (m, 4H), 2.54 (t, J=7.95 Hz, 2H), 3.36 (d, J=7.20 Hz, 2H), 3.92-3.93 (m, 4H), 4.08 (t, J=4.35 Hz, 4H), 5.06 (t, J=6.45 Hz, 1H), 5.15 (t, J=6.6 Hz, 1H), 6.38 (s, 2H).

Example 15. Synthesis of Intermediate A

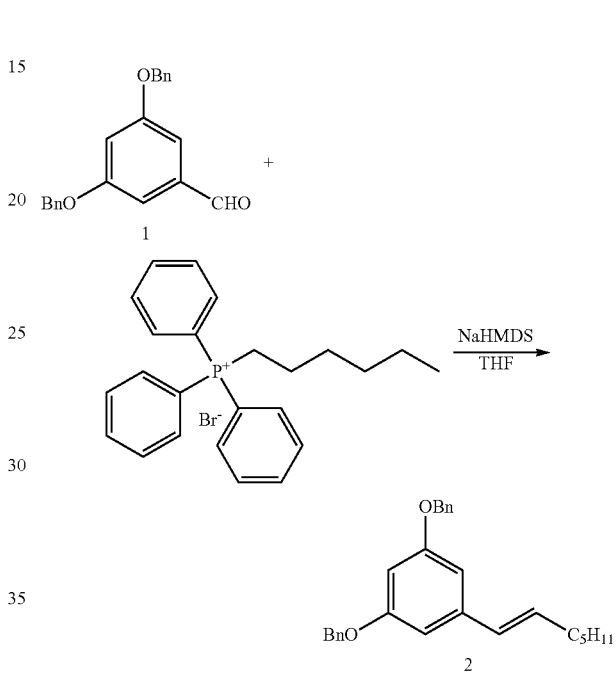

A suspension of hexyl triphenyl phosphonium bromide (500.0 g, 1.1 eq, 1.17 mol) was made in THF (3.4 L). The reaction mixture was cooled to −10° C. To this was added NaHMDS (215.0 g, 1.1 eq, 1.17 mol) dropwise maintaining temperature below 0° C. The solution turned bright yellow-orange suspension. The reaction mixture was stirred at 0° C. for one hour. To this mixture, aldehyde (339.0 g, 1.0 eq, 1.06 mol) dissolved in THF (650 mL) was added slowly maintaining the temperature below 5° C. Upon addition, the reaction mixture was slowly warmed to room temperature and left stirring overnight. After 17 hours, TLC confirms total conversion by absence of aldehyde.

The mixture was diluted with water (2.0 L) and ethyl acetate (2.0 L), separated the layers, organic phase was washed with water (4×2.0 L) and brine (1.0 L), dried over anhydrous sodium sulfate, filtered, concentrated under reduced pressure to get 378 gr crude compound. Took a wide mouth cintered funnel. 9" wide and 12" Long. Filled silica gel until 9". Eluted with 5 L Heptane—No product eluted out. Eluted with 5 L 10% Ethyl acetate in heptane—No product eluted. Eluted with 10 L 10% ethyl acetate in heptane—The product eluted out. Another 5 L 10% ethyl acetate in heptane—Dark yellow eluent came out-No product. Pooled all the fractions containing product. Concentrated under reduced pressure. Dried under high vacuum and obtained 321 gr of pure product.

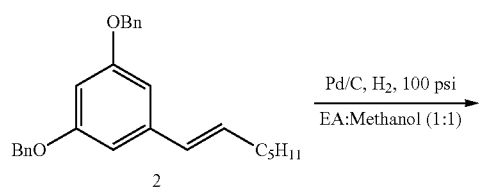

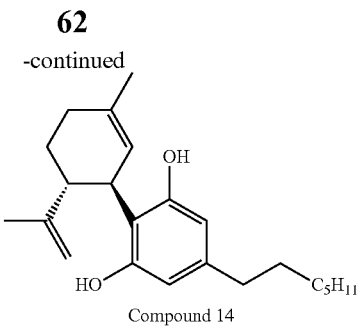

Compound 14

Process Description

To a stirred mixture of Intermediate A (82.0 g, 1.0 eq, 394.0 mmol) in toluene (3.5 L) was added (1S,4R)-1-methyl-4-(prop-1-en-2-yl)cyclohex-2-en-1-ol (65.9 g, 1.1 eq, 433.0 mmol) under nitrogen atmosphere at room temperature. Then the reaction mixture cooled to 0° C. and added PTSA (7.49 g, 0.1 eq, 39.4 mmol), and continued stirring for 20 mins at same temperature. TLC (20% ethyl acetate in heptane) confirms formation of product and some amount of starting material. LCMS also confirms the product formation ($[C_{23}H_{34}O_2+H]^+[M+H]$: 343.5) along with unwanted isomer. Quenched the reaction mixture at 0° C. with sat.aq. $NaHCO_3$. The mixture was diluted with ethyl acetate (500 mL), separated the layers, organic phase was washed with water (500 mL), brine (250 mL), dried over anhydrous sodium sulfate, filtered, concentrated under reduced pressure to get crude which was purified by combi-flash column (330 g) using heptane (0.5% triethylamine)/ethyl acetate as eluent. The pure product fractions were concentrated under reduced pressure, dried under high vacuum at rt for 16 h to get pure compound 14 (22.0 g, 16.3%) as grey color liquid.

Figure 39:
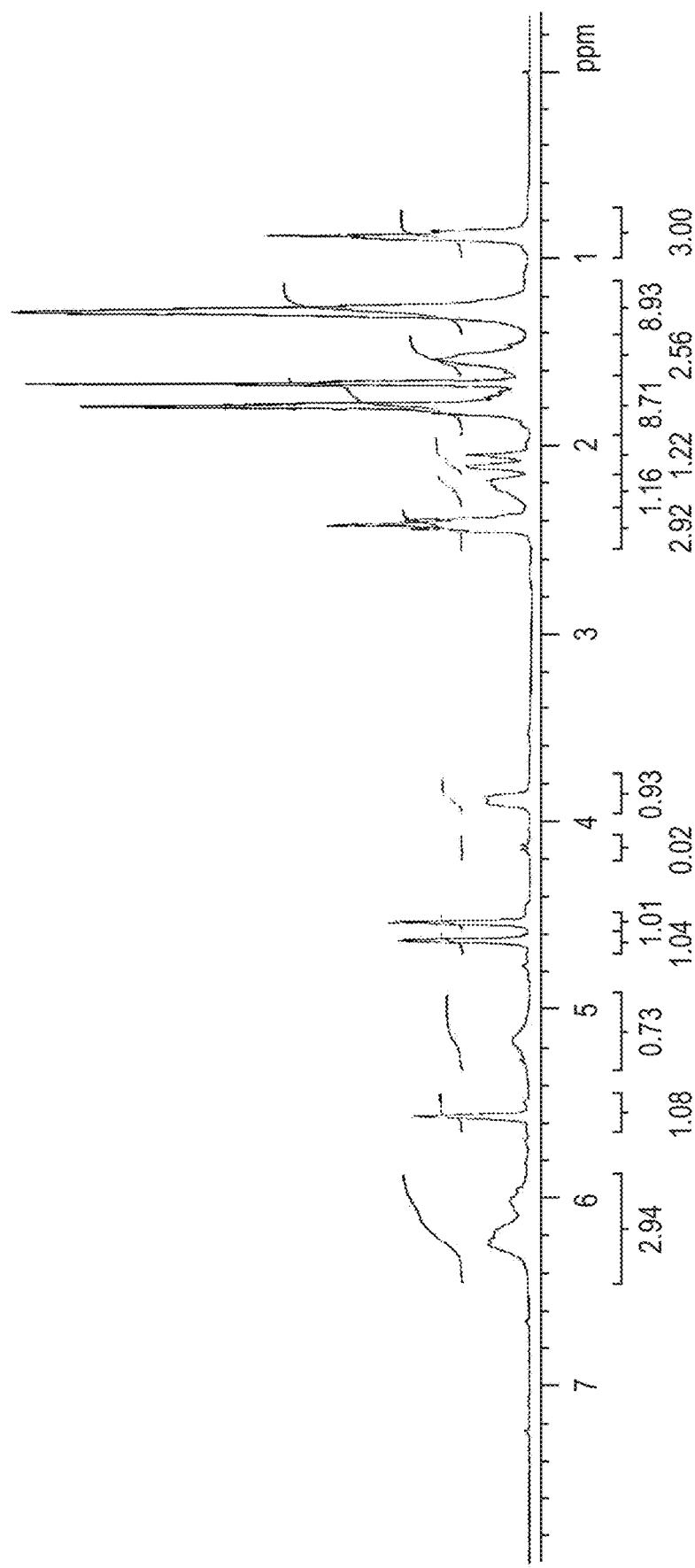
FIG. 39 shows a $^1$H NMR spectrum of Compound 14.

Compound 14: FIG. 39 shows a $^1$H NMR ($CDCl_3$) spectrum of Compound 14. $^1$H NMR spectrum was obtained 25° C. on a Merc200-mercury300 spectrometer.

Example 16. Synthesis of (1R,2R)-4'-heptyl-2',6'-dimethoxy-5-methyl-2-(prop-1-en-2-yl)-1,2,3,4-tetrahydro-1,1'-biphenyl (Compound 15)

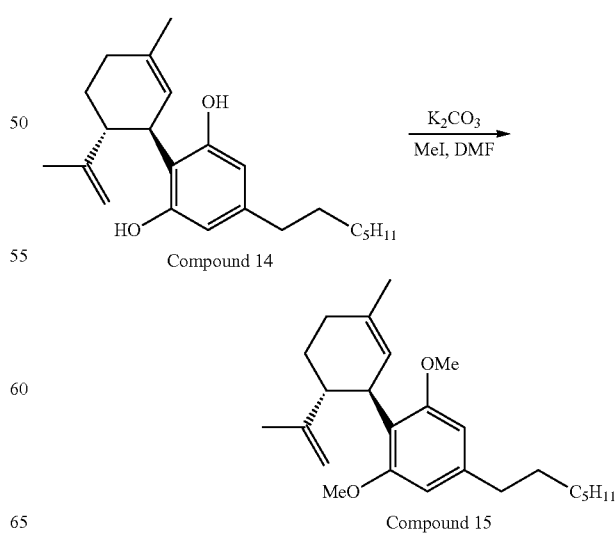

Compound 14

Compound 15

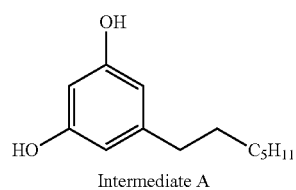

Intermediate A

To a suspension of Pd/C (20.0 g, 0.33 eq, 169.0 mmol) in DCM was added compound 2 (196.0 g, 1.0 eq, 507.1 mmol) into the 2 L autoclave. To the mixture was added methanol and ethyl acetate (1.4 L) in 1:1 ratio. The Autoclave vessel is capped tightly. The hydrogen is passed into the vessel. bubbled at 50 psi. stirred for 5 min and the pressure was vented out to remove any dissolved oxygen. This procedure was done thrice to ensure complete removal of the dissolved oxygen. The autoclave was maintained at pressure of 100 psi and stirred overnight. After completion of the reaction by TLC and LCMS solids were filtered off using a pad of celite. The pad was washed with ethyl acetate (500 mL) and the filtrate was concentrated. This reaction mixture was combined with batch SP-000095-CAR-0021. The total reaction mixture from two batches was combined and dissolved in 1.0 L DCM. To this was added 200 grams of activated carbon along with 400 grams of silica gel. The suspension was stirred overnight stirred and Silica gel/Carbon was filtered off using a pad of celite. The filtrate was concentrated. The concentrated residue triturated with heptane (1.5 L). The solids were filtered and dried and obtained 178 gr of Intermediate A. This reaction was performed as 196.0 g x1, and 200.0 g x1, using total of 396.0 g of compound 2. Yield: 178.0 g (83.4%).

Example 15. Synthesis of (1'R,2'R)-4-heptyl-5'-methyl-2'-(prop-1-en-2-yl)-1',2',3',4'-tetrahydro-[1,1'-biphenyl]-2,6-diol (Compound 14)

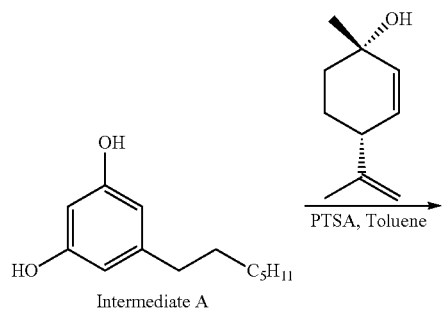

Intermediate A

To a stirring solution of Compound 14 (22.0 g, 1.0 eq, 64.2 mmol) in DMF (220 mL), K$_2$CO$_3$ (35.5 g, 4.0 eq, 257.0 mmol) was added at 0° C. Then MeI (40.37 g, 4.0 eq, 257.0 mmol) was added at 0° C. dropwise over a period of 10 min and the mixture was stirred for 30 mins at 0° C. The reaction mixture was stirred for overnight at room temperature. After completion of the reaction as indicated by TLC (10% ethyl acetate in heptane) and LCMS, the mixture was diluted with water (220 mL) extracted with ethyl acetate (2×220 mL). The organic phase was washed with water (220 mL), brine (110 mL), and dried over anhydrous sodium sulfate. The solids are filtered, and the filtrate was concentrated under reduced pressure to get crude which was purified by combi-flash column (330 g) using heptane (0.5% Et$_3$N)/ethyl acetate as eluent. The pure product fractions were pooled and concentrated under reduced pressure and dried under high vacuum for 16 h to get pure compound 15 (15 g, 63%) as light-yellow liquid.

Example 17. Synthesis of (1'R,2'R)-4-heptyl-6-methoxy-5'-methyl-2'-(prop-1-en-2-yl)-1',2',3',4'-tetrahydro-[1,1'-biphenyl]-2-ol (Compound 16)

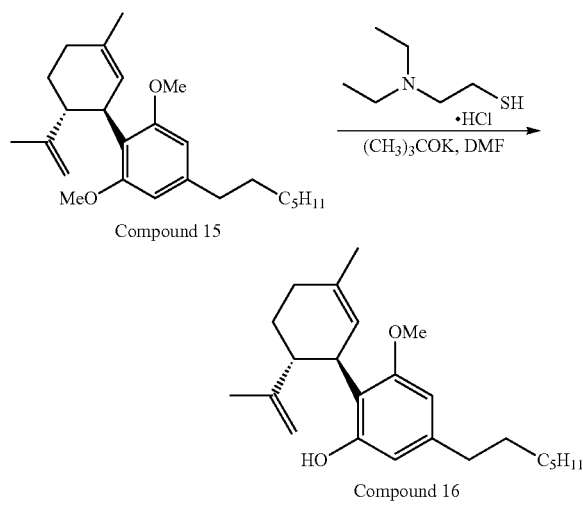

Compound 15

Compound 16

7.2 Process Description

To a stirring solution of Thiol (20.6 g, 3.0 eq, 121.0 mmol) in DMF (300 mL), KOtBu (27.3 g, 6.0 eq, 243.0 mmol) was added in three portions under 5° C. After stirring 20 min at rt, compound 15 (15.0 g, 43.5 mmol) dissolved in DMF (120 mL) was added over a period of 10 min. The resulting reaction mixture was refluxed for 2.5 h. Completion of the reaction was indicated by TLC (10% ethyl acetate in heptane) and LCMS. The reaction mixture was cooled to 0-5° C., water (250 mL) and ethyl acetate (2×300 mL) was added. Organic layer was washed with cold water (3×200 mL), brine (2×200 mL), and dried over anhydrous sodium sulfate. The solids were filtered, and the filtrate was concentrated under reduced pressure to get crude mixture. The crude mixture was purified by combi-flash column (220 g) using heptane (0.5% Et$_3$N)/ethyl acetate as eluents. The pure product fractions were concentrated under reduced pressure, dried under high vacuum at rt for 16 h to get pure Compound 16 (9.0 g, 62%) as a light-yellow liquid.

Figure 40:
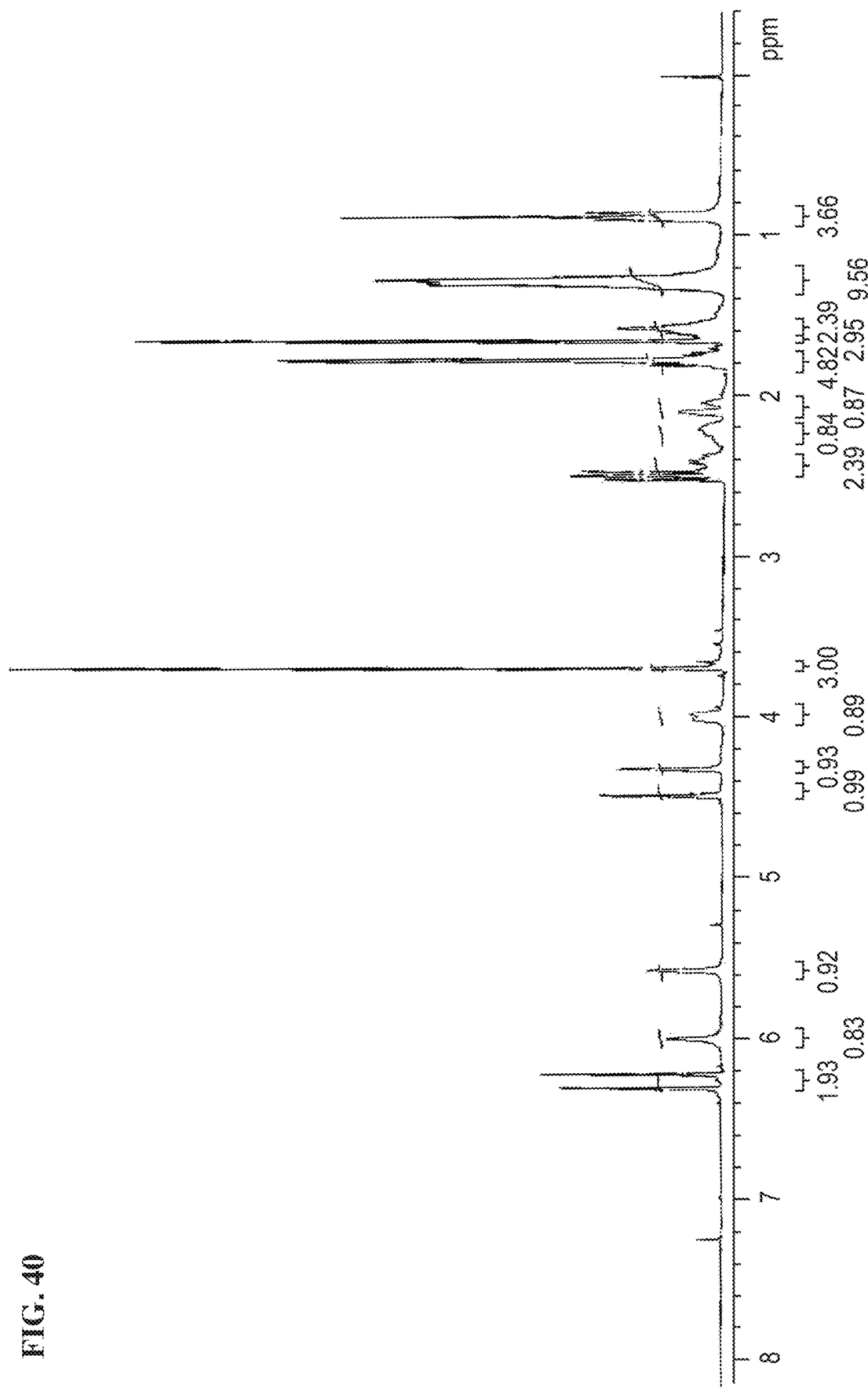
FIG. 40 shows a $^1$H NMR spectrum of Compound 16.

Compound 16: FIG. 40 shows a $^1$H NMR (CDCl$_3$) spectrum of Compound 16. $^1$H NMR spectrum was obtained 25° C. on a Merc200-mercury300 spectrometer.

Example 18. Synthesis of (E)-2-(3,7-dimethylocta-2,6-dien-1-yl)-5-heptylbenzene-1,3-diol (Compound 17)

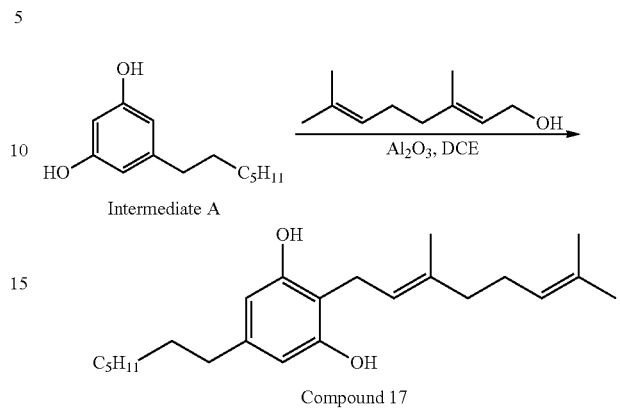

Intermediate A

Compound 17

To a stirring solution of alumina (400.0 g, 16.0 eq, 3.92 mol) in DCE (250 mL), was added Intermediate A (50.0 g, 1.0 eq, 0.24 mol) and geraniol (24.0 g, 0.66 eq, 0.16 mol) was added at room temperature. The mixture was stirred for 6 hr. at reflux temperature. After completion of the reaction as indicated by TLC (10% ethyl acetate in heptane) and LCMS, the reaction mixture was filtered and the solids were washed with DCM (300 mL). The filtrate was washed with sat. aq. NaHCO$_3$(500 mL) and with brine (250 mL) and dried over anhydrous sodium sulfate. The filtrate was concentrated under reduced pressure to get crude which was purified by combi-flash column (330 g) using heptane/ethyl acetate as eluent. The pure product fractions were concentrated under reduced pressure, dried under high vacuum at rt for 16 h to get pure Compound 17 as light brown solid.

Figure 41:
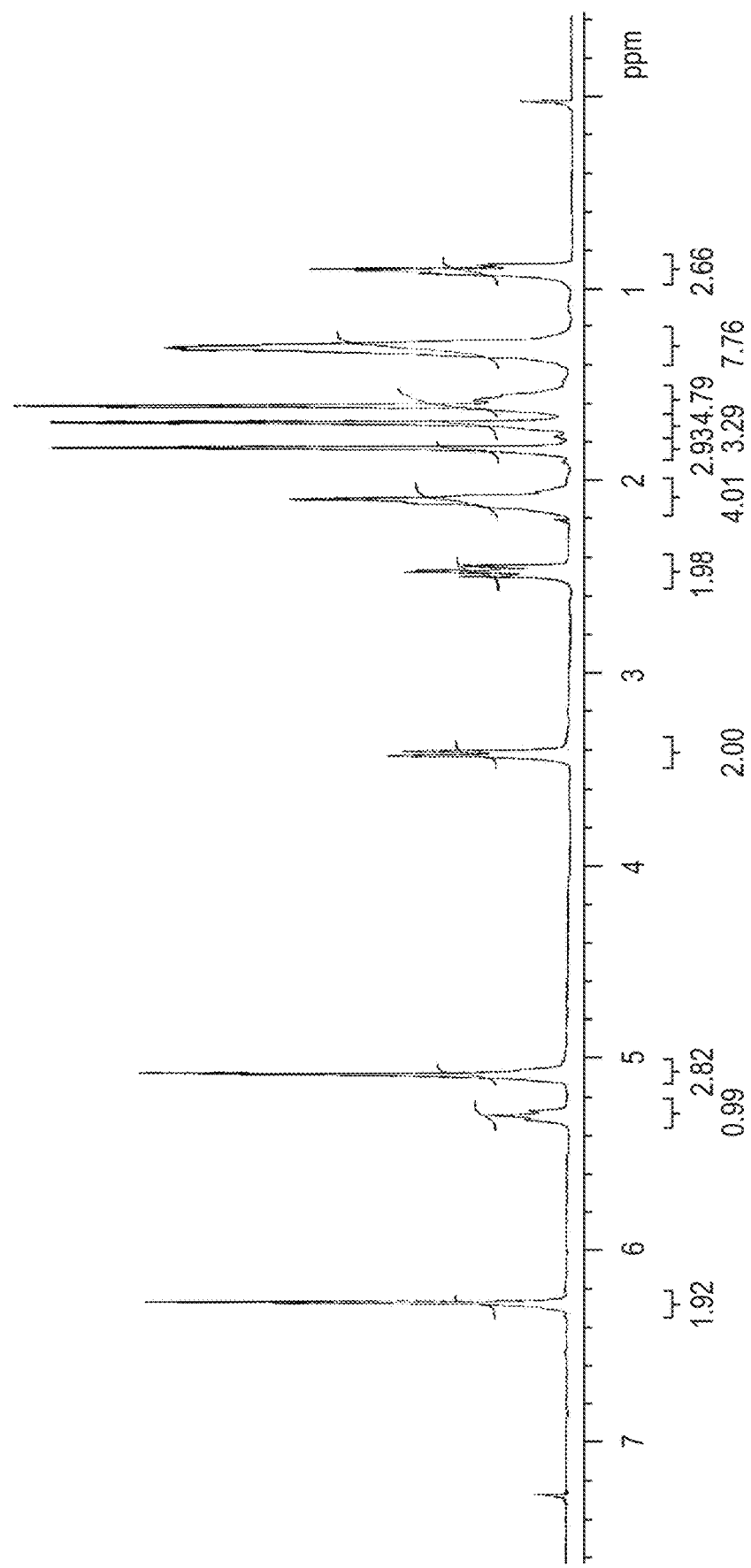
FIG. 41 shows a $^1$H NMR spectrum of Compound 17.

Compound 17: FIG. 41 shows a $^1$H NMR (CDCl$_3$) spectrum of Compound 17. $^1$H NMR spectrum was obtained 25° C. on a Merc200-mercury300 spectrometer.

Example 19. Synthesis of (E)-2-(3,7-dimethylocta-2,6-dien-1-yl)-5-heptyl-1,3-dimethoxybenzene (Compound 18)

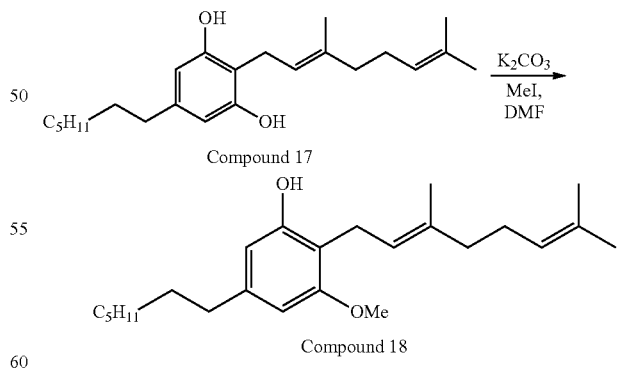

Compound 17

Compound 18

9.2 Process Description

To a stirring solution of Compound 17 (24.5 g, 1.0 eq, 71.11 mmol) in DMF (245 mL), K$_2$CO$_3$ (39.31 g, 4.0 eq, 284.4 mmol) was added at 0° C. Then MeI (40.37 g, 4.0 eq, 284.4 mmol) was added at 0° C. dropwise over a period of 10 min and the mixture was stirred for 30 mins at 0° C. The reaction mixture was stirred for overnight at room temperature. After completion of the reaction as indicated by TLC (10% ethyl acetate in heptane) and LCMS, the mixture was diluted with water (300 mL) extracted with ethyl acetate (2×250 mL). The organic phase was washed with water (300 mL), brine (100 mL), and dried over anhydrous sodium sulfate. The filtrate was concentrated under reduced pressure to get crude mixture which was purified by combi-flash column (330 g) using heptane/ethyl acetate as eluent. The pure product fractions were concentrated under reduced pressure, dried under high vacuum at rt for 16 h to get pure Compound 18 (14.0 g, 52.83%) as light yellow liquid.

Figure 42:
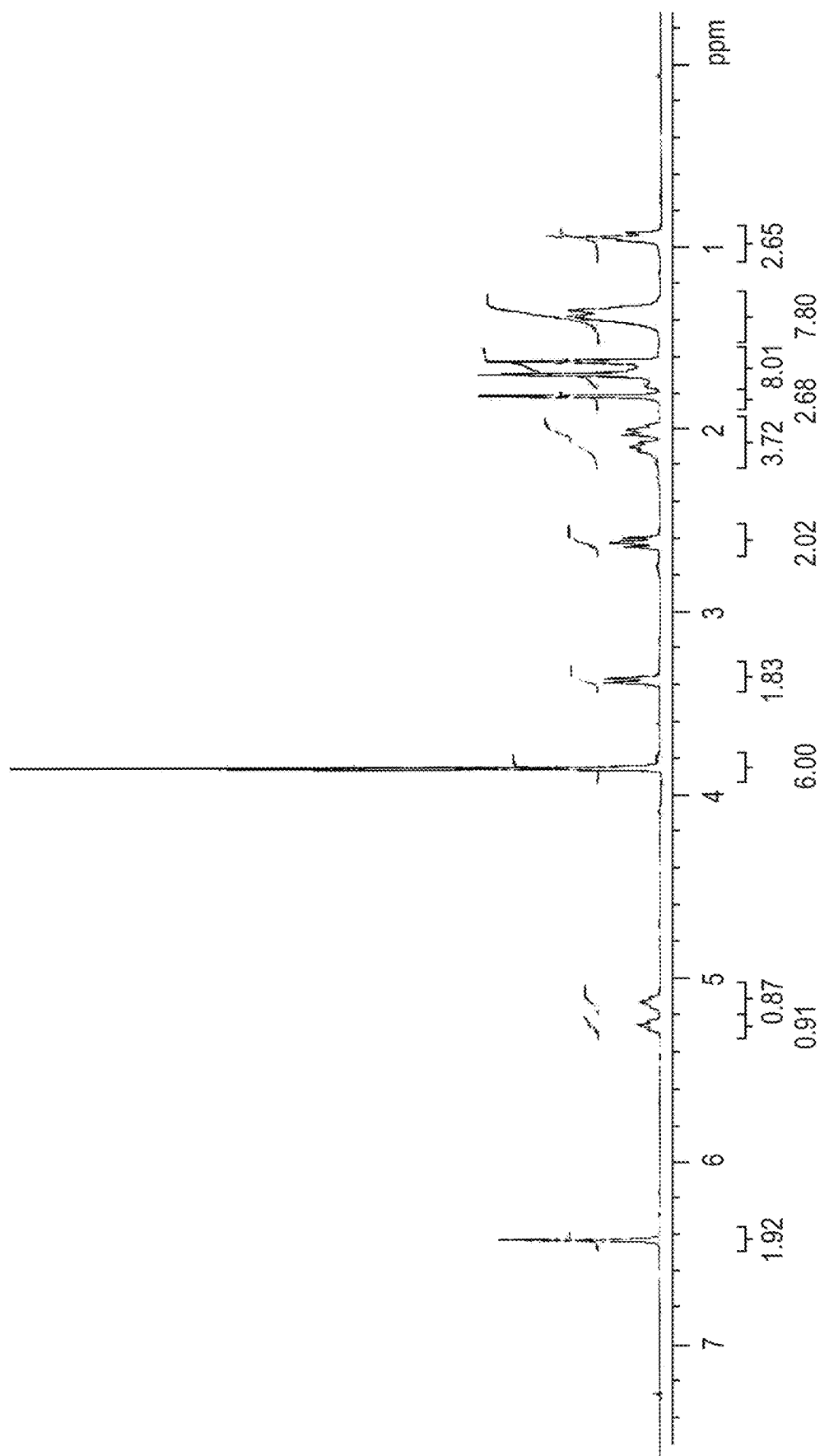
FIG. 42 shows a $^1$H NMR spectrum of Compound 18.

Compound 18: FIG. 42 shows a $^1$H NMR (CDCl$_3$) spectrum of Compound 18. $^1$H NMR spectrum was obtained 25° C. on a Merc200-mercury300 spectrometer.

Example 20. Synthesis of (E)-2-(3,7-dimethylocta-2,6-dien-1-yl)-5-heptyl-3-methoxyphenol (Compound 19)

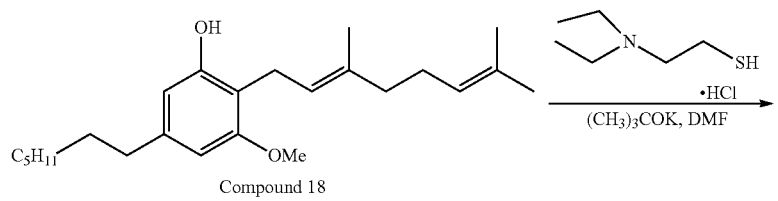

Compound 18

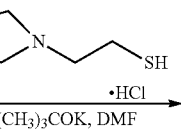

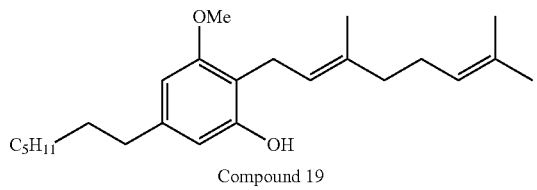

Compound 19

To a stirring solution of thiol (15.58 g, 3.0 eq, 91.79 mmol) in DMF (228 mL) KOtBu (20.60 g, 6.0 eq, 183.6 mmol) was added in three portions under 5° C. After stirring 20 min at rt, compound 18 (11.4 g, 30.6 mmol) dissolved in DMF (90 mL) was added at rt over a period of 10 min. The resulting reaction mixture was refluxed for 2.5 h. After completion of the reaction as indicated by TLC (10% ethyl acetate in heptane) and LCMS. The reaction mixture was cooled to 0-5° C., 1N HCl (380 mL) was added to adjust pH ~1. Water (200 mL) was added, extracted with ethyl acetate (500 mL), Organic layer was washed with cold water (2×250 mL), brine (300 mL), and dried over anhydrous sodium sulfate. The filtrate was concentrated under reduced pressure to get crude residue which was purified by combi-flash column (330 g) using heptane/ethyl acetate as eluent. The pure product fractions were concentrated under reduced pressure, dried under high vacuum at rt for 16 h to get pure Compound 19 as a pale-yellow oil.

Figure 43:
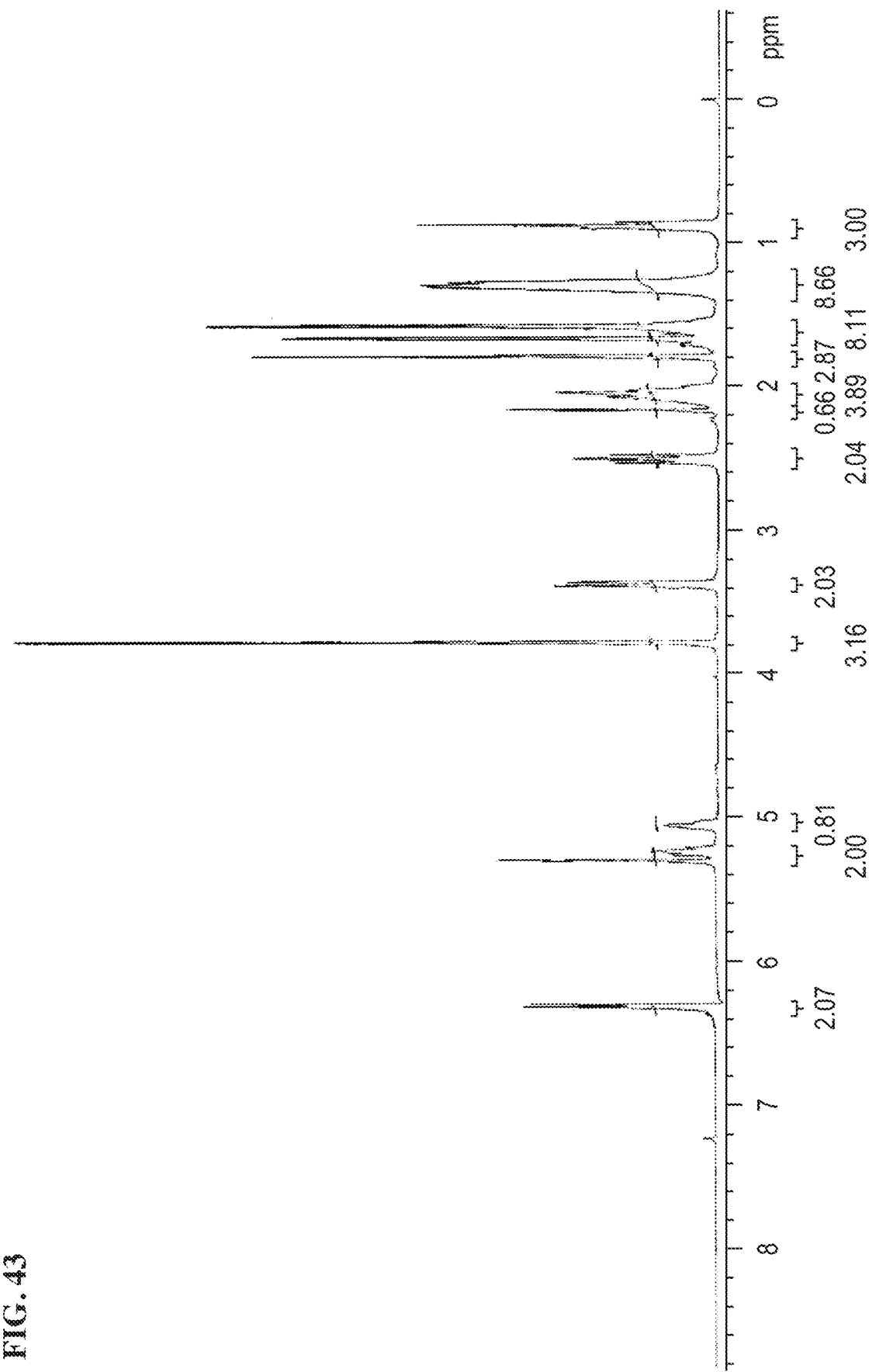
FIG. 43 shows a $^1$H NMR spectrum of Compound 19.
Figure 44:
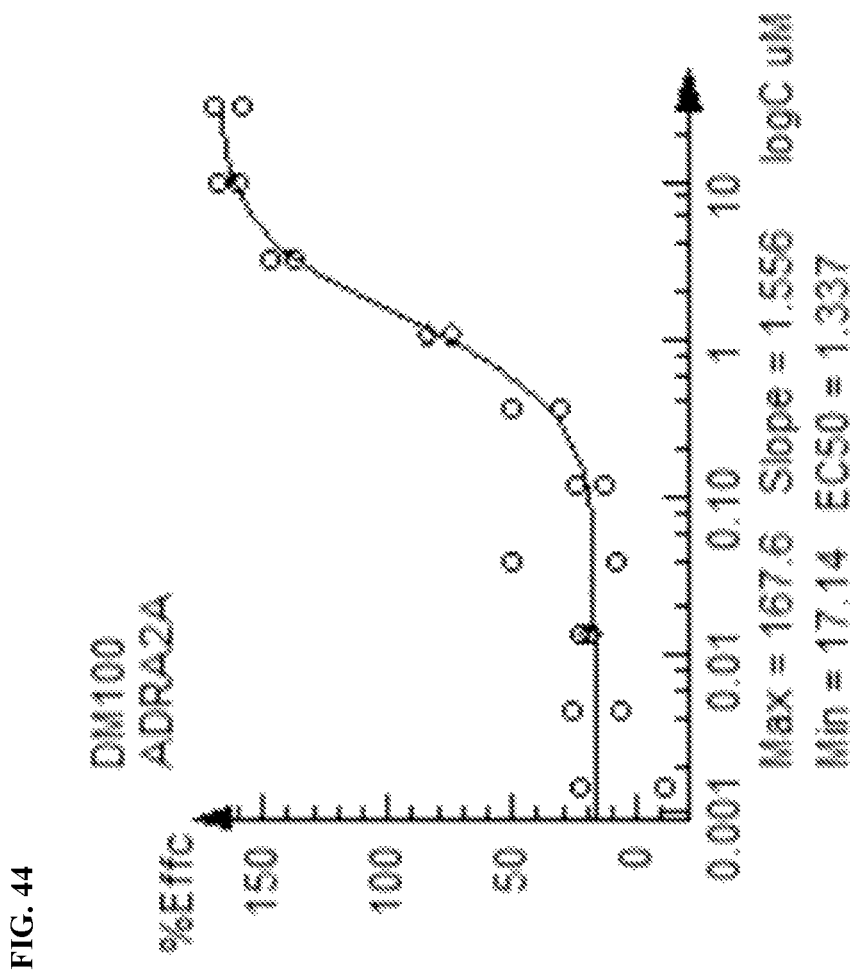
FIG. 44 shows a graph of % Effc vs Log C (uM) for CBG in an ADRA2A agonist assay.

Compound 19: FIG. 43 shows a $^1$H NMR (CDCl$_3$) spectrum of Compound 19. $^1$H NMR spectrum was obtained 25° C. on a Merc200-mercury300 spectrometer.

Example 21. Synthesis of (1'R,2'R)-6-methoxy-5'-methyl-4-pentyl-2'-(prop-1-en-2-yl)-1',2',3',4'-tetrahydro-[1,1'-biphenyl]-2-ol (Compound 3)

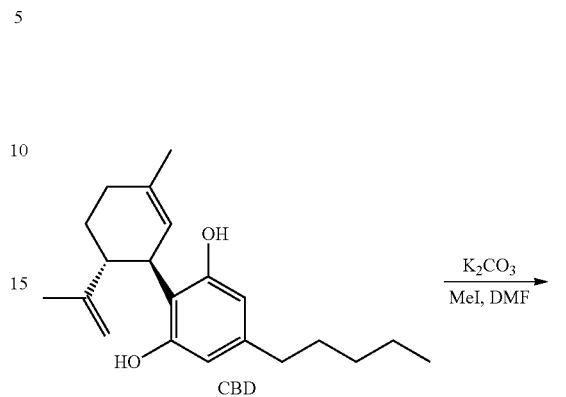

CBD

-continued

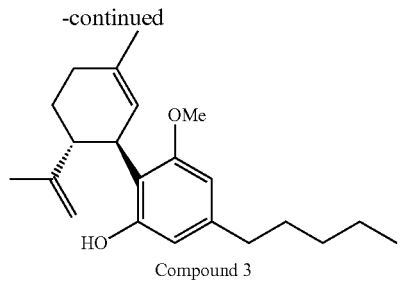

Compound 3

A 200 mL single neck round bottom flask was charged with CBD (5 g; 15.90 mmol) and K$_2$CO$_3$ (3.4 g; 23.84 mmol) and DMF (75 mL). The reaction mixture was stirred at room temperature for 30 min under nitrogen. CH$_3$I (2.71 g; 19.08 mmol) was added to the heterogeneous reaction mixture in 10 min. The reaction mixture was stirred at room temperature for 5 hours under nitrogen. The reaction was monitored by TLC (10% Ethyl acetate+hexane). TLC shows 30-40% dimethoxy CBD, 25-30% Monomethoxy CBD and 20-25% CBD. Filtered the K$_2$CO$_3$ and washed with DMF (20.0 mL). The filtrate was added to the ice-cold water (200.0 mL) and was extracted with Ethyl acetate (100 mL). Ethyl acetate layer was washed with water (2×50 mL). Ethyl acetate layer was dried over $Na_2SO_4$ and concentrated to obtain 5.2 g of crude material.

Crude material column purification (ISCO) using 1-10% Ethyl acetate in Heptane. Pure fractions were concentrated to obtained 1.2 g Compound 3 (Monomethoxy CBD) as pale yellow oil.

Figure 36:
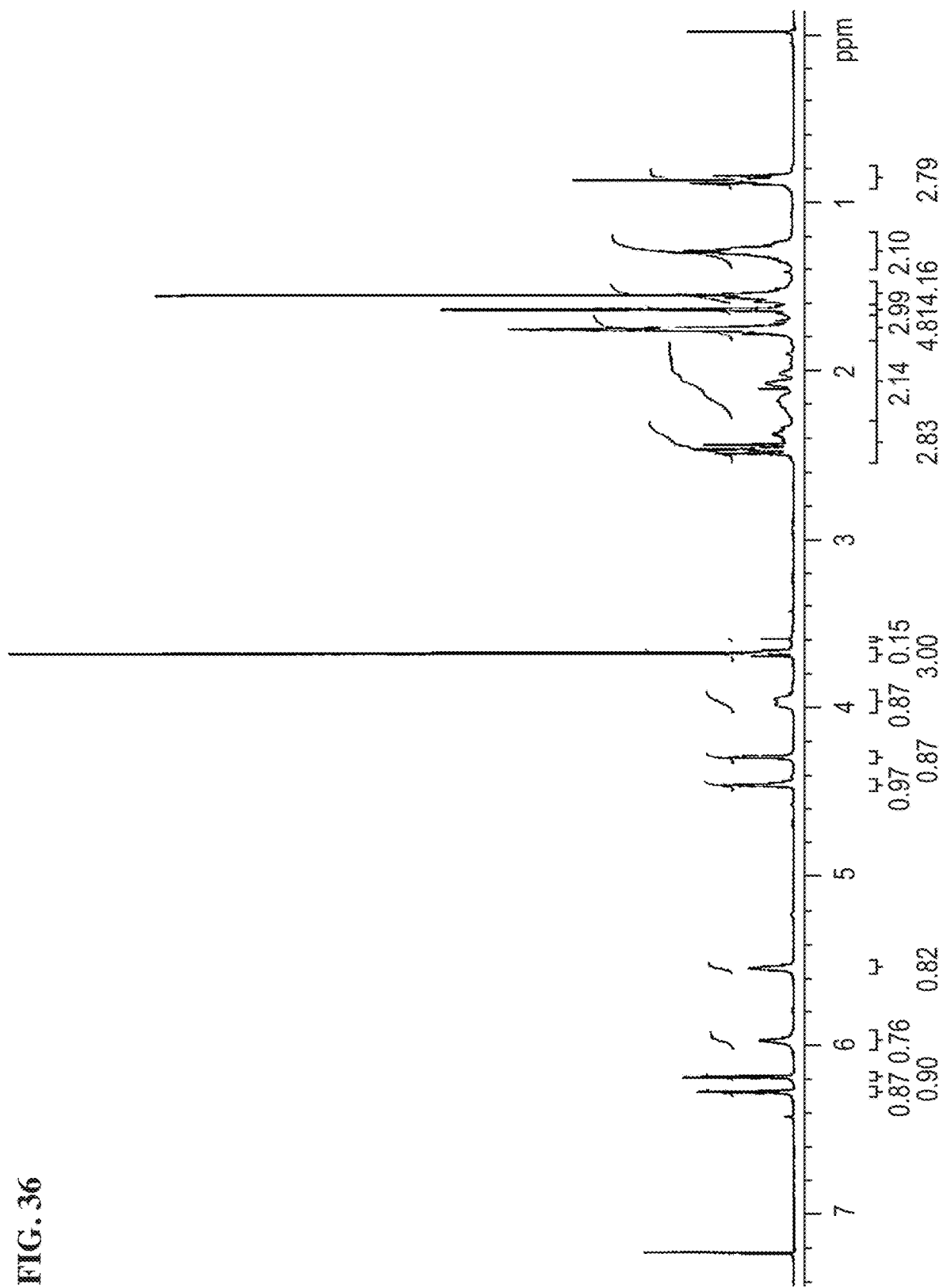
FIG. 36 shows a $^1$H NMR spectrum of Compound 3.

Compound 3: FIG. 36 shows a $^1$H NMR ($CDCl_3$) spectrum of Compound 3. $^1$H NMR spectrum was obtained 25° C. on a Merc200-mercury300 spectrometer.

Example 22. PK and Time of Maximum Plasma (Tmax) for CBD and Compound 3

Objectives and Background

The purpose of this study was to determine the pharmacokinetics and time of maximum plasma ($T_{max}$) of the test articles (TA) CBD and Compound 3 following intraperitoneal (IP) administration to male C57BL/6 mice. This method of TA delivery, dose and mouse strain was to be used in a subsequent Pentylenetetrazol (PTZ) induced seizure model for the evaluation of the TA's for anti-epileptic activity.

Other compounds of the present disclosure (e.g., one or more compounds of Formula (I), (II), (III), Table 1 or Table 2) may also be evaluated in this assay.

Study Design

| Group | N/Sex | Test Article | Dose (mg/kg) | Vehicle | Route |
|---|---|---|---|---|---|
| 1 | 27/M | CBD | 100 | 10% EtOH/ 10% Tween 80/ 80% Saline | IP |
| 2 | 27/M | Compound 3 | 100 | 10% EtOH/ 10% Tween 80/ 80% Saline | IP |

Sample Collection

| Group | Matrix | Anti-coagulant | Volume/ Time Point | Collection Times (h postdose) |
|---|---|---|---|---|
| All | Blood/Plasma | $K_2$EDTA | ~1 mL (exsanguination) | 0, 0.25, 0.5, 1, 1.5, 2, 2.5, 4, and 24 |

Results

| Data description | PK unit | Group 1 | Group 2 |
|---|---|---|---|
| AUC(0-t) (obs area) | ng-hr/mL | 6834 | 30231 |
| $C_{Max}$ | ng/mL | 2727 | 21840 |
| $T_{Max}$ | Minutes | 15 & 60 | 30 |

Compound 3 clearly demonstrated improved bioavailability over CBD with plasma PK Area Under the Curve (AUC) calculation of over 4-fold greater and a $C_{max}$ of 8-fold greater. CBD had two separate $T_{max}$ peaks, we decided to use the later 60 minute time for PTZ studies as the overall blood plasma was more consistent at that timepoint.

Example 23 Receptor Binding Assay

Compounds of the present disclosure (e.g., one or more compounds of Formula (I), (II), (III), Table 1 or Table 2) may be tested for activity in receptor binding assays using methods known in the art, to evaluate agonist, antagonist, inverse agonist and other modes of activity. For example compounds of the disclosure may be tested in a adrenoceptor alpha 2A (ADRA2A) Agonist assay as follows:

cAMP Secondary Messenger Pathway Assay Overview

Cell lines stably expressing non-tagged adrenoceptor alpha 2A (ADRA2A) that signal through cAMP were used. Agonist assays monitored by the activation of ADRA2A via Gi or Gs secondary messenger signaling in a homogenous, non-imaging assay format using a technology called Enzyme Fragment Complementation (EFC) with β-galactosidase (β-Gal) as the functional reporter.

The enzyme is split into two complementary portions: EA for Enzyme Acceptor and ED for Enzyme Donor. ED is fused to cAMP and in the assay competes with cAMP generated by cells for binding to a cAMP-specific antibody. Active β-Gal is formed by complementation of exogenous EA to any unbound ED cAMP. Active enzyme can then convert a chemiluminescent substrate, generating an output signal detectable on a standard microplate reader.

Cell Handling 1. cAMP assay ADRA2A cell lines were expanded from freezer stocks according to standard procedures.
2. Cells were seeded in a total volume of 20 μL into white walled, 384 well microplates and incubated at 37° C. for the appropriate time prior to testing
3. cAMP modulation was determined using the DiscoverX HitHunter cAMP XS+ assay Gs Agonist Format 1. For agonist determination, cells were incubated with sample to induce response.
2. Media was aspirated from cells and replaced with 15 μL 2:1 HBSS/10 mM Hepes: cAMP XS+Ab reagent.
3. Intermediate dilution of sample stocks was performed to generate 4× sample in assay buffer.
4. 5 μL of 4× sample was added to cells and incubated at 37° C. or room temperature for 30 or 60 minutes. Vehicle concentration was 1%.

Gi Agonist Format

1. For agonist determination, cells were incubated with sample in the presence of EC80 forskolin to induce response.
2. Media was aspirated from cells and replaced with 15 μL 2:1 HBSS/10 mM Hepes: cAMP XS+Ab reagent.
3. Intermediate dilution of sample stocks was performed to generate 4× sample in assay buffer containing 4× EC80 forskolin.
4. 5 μL of 4× sample was added to cells and incubated at 37° C. or room temperature for 30 or 60 minutes. Final assay vehicle concentration was 1%

Signal Detection

1. After appropriate compound incubation, assay signal was generated through incubation with 20 μL cAMP XS+ED/CL lysis cocktail for one hour followed by incubation with 20 μL cAMP XS+EA reagent for three hours at room temperature.
2. Microplates were read following signal generation with a PerkinElmer Envision™ instrument for chemiluminescent signal detection.

Data Analysis

1. Compound activity was analyzed using CBIS data analysis suite (ChemInnovation, CA)
2. For Gs agonist mode assays, percentage activity is calculated using the following formula: % Activity=100%×(mean RLU of test sample−mean RLU of vehicle control)/(mean RLU of MAX control−mean RLU of vehicle control).

3. For Gi agonist mode assays, percentage activity is calculated using the following formula:

% Activity=100%×(1−(mean *RLU* of test sample−mean *RLU* of MAX control)/(mean *RLU* of vehicle control−mean *RLU* of MAX control))

Results for ADRA2A agonist assay—CBG

| Result Type | RC50 | Unit | Hill | Curve Bottom | Curve Top | Max Response |
|---|---|---|---|---|---|---|
| EC50 | 1.337362 | uM | 1.5564 | 17.138 | 167.56 | 163.39 |

Example 24. Effects of Compounds on LPS Stimulated Human PBMCs In Vitro

The effects of compounds of the present disclosure (e.g., one or more compounds of Formula (I), (II), (III), Table 1 or Table 2) on LPS Stimulated Human PBMCs in vitro can be tested using the following protocol.

Protocol

Three separate fresh blood samples (2×10 ml per donor) were acquired from ZenBio, shipped overnight NOT frozen. Upon receipt, cells were separated into 10 ml aliquots and mixed 3:1 with RBC lysis buffer for 15 min at Room Temp (RT). Cells were then washed 2× with sterile PBS and cells from the same donor then pooled and counted using a Luna FL cell counter to obtain viable nucleated cell counts using fluorescent dyes (Acridine Orange/Propidium Iodide). Cells were diluted to 2e6 cells/ml in Complete RPMI (RPMI+10% FBS+1× Pen/Strep/Glut) and 125 ul was added to each well of 96-well flat bottom plates. 125 ul of cRPMI containing each diluted test article (compounds of the disclosure) were added to the wells at time 0 h and briefly pipet mixed. Cells were pre-treated for 1 h at 37 C/5% CO2. After 1 h cells were stimulated with 100 ng/ml LPS for an additional 24 h at 37 C/5% CO2. After a total of 25 h plates were spun down and supernatants harvested into a new 96-well plate and sealed using a foil adhesive seal and saved for Luminex cytokine analysis. Pelleted cells were moved into a new 96 deep well plates for Flow Cytometry. Replicate wells will be combined into a single well for combined analysis.

Cell and Supernatant Harvest Outline

| Type | Process For | Final Volume | Storage Condition | Disposition |
|---|---|---|---|---|
| Cells | Cell Pellets | +/−250,000 cells | Flow | Stained for Flow Cytometry |
| Supernatant | Luminex | 250 ul | −80 C. | Luminex Cytokine Analysis |

Sample Analysis

| Analysis | Sample/Tissue | |
|---|---|---|
| Flow Cytometry Phenotype | Human PBMCs | Analysis of different cell populations by Flow Cytometry. Three replicate wells pooled into a single Flow staining well. |
| Milliplex Multiplex HCYTOMAG-60K | Cell Supernatant | Human Luminex 9plex: GM-CSF, IFN-γ, IL-10, IL-12p70, IL-17A/CTLA8, IL-18, IL-1β, IL-6, TNF-α |

Example 25. BioMap Diversity Plus Panel

Background on BioMAP Technology Platform

BioMAP panels consist of human primary cell-based systems designed to model different aspects of the human body in an in vitro format. The 12 systems in the Diversity PLUS panel allow test agent characterization in an unbiased way across a broad set of systems modeling various human disease states. BioMAP systems are constructed with one or more primary cell types from healthy human donors, with stimuli (such as cytokines or growth factors) added to capture relevant signaling networks that naturally occur in human tissue or pathological conditions. For example, systems that recapitulate aspects of the systemic immune response including monocyte-driven Th1 inflammation (LPS system) or T cell stimulation (SAg system), chronic Th1 inflammation driven by macrophage activation (IMphg system) and the T cell-dependent activation of B cells that occurs in germinal centers (BT system). BioMAP is also used to predict toxicity profiles. Each test agent generates a signature BioMAP profile that is created from the changes in protein biomarker readouts within individual system environments. Biomarker readouts (7-17 per system) are selected for therapeutic and biological relevance, are predictive for disease outcomes or specific drug effects and are validated using agents with known mechanism of action (MoA). Each readout is measured quantitatively by immune-based methods that detect protein (e.g., ELISA) or functional assays that measure proliferation and viability. BioMAP readouts are diverse and include cell surface receptors, cytokines, chemokines, matrix molecules and enzymes.

Methods

Human primary cells in BioMAP systems are used at early passage (passage 4 or earlier) to minimize adaptation to cell culture conditions and preserve physiological signaling responses. All cells are from a pool of multiple donors (n=2-6), commercially purchased and handled according to the recommendations of the manufacturers. Human blood derived CD14+ monocytes are differentiated into macrophages in vitro before being added to the IMphg system. Abbreviations are used as follows: Human umbilical vein endothelial cells (HUVEC), Peripheral blood mononuclear cells (PBMC), Human neonatal dermal fibroblasts (HDFn), B cell receptor (BCR), T cell receptor (TCR) and Toll-like receptor (TLR). Cell types and stimuli used in each system are as follows: 3C system [HUVEC+(IL-1β, TNFα and IFNγ)], 4H system [HUVEC+(IL-4 and histamine)], LPS system [PBMC and HUVEC+LPS (TLR4 ligand)], SAg system [PBMC and HUVEC+TCR ligands], BT system [CD19+B cells and PBMC+(α-IgM and TCR ligands)], BF4T system [bronchial epithelial cells and HDFn+(TNFα and IL-4)], BE3C system [bronchial epithelial cells+(IL-1β, TNFα and IFNγ)], CASM3C system [coronary artery smooth muscle cells+(IL-1β, TNFα and IFNγ)], HDF3CGF system [HDFn+(IL-1β, TNFα, IFNγ, EGF, bFGF and PDGF-BB)], KF3CT system [keratinocytes and HDFn+(IL-1β, TNFα, IFNγ and TGFβ)], MyoF system [differentiated lung myofibroblasts+(TNFα and TGFβ)] and IMphg system [HUVEC and M1 macrophages+Zymosan (TLR2 ligand)]. Systems are derived from either single cell types or co-culture systems. Adherent cell types are cultured in 96 or 384-well plates until confluence, followed by the addition of PBMC (SAg and LPS systems). The BT system consists of CD19+B cells co-cultured with PBMC and stimulated with a BCR activator and low levels of TCR stimulation. Test agents prepared in either DMSO (small molecules; final concentration ≤0.1%) or PBS (biologics) are added at the indicated concentrations 1-hr before stimulation, and remain in culture for 24-hrs or as otherwise indicated (48-hrs, MyoF system; 72-hrs, BT system (soluble readouts); 168-hrs, BT system (secreted IgG)). Each plate contains drug controls (e.g., legacy control test agent colchicine at 1.1 µM), negative controls (e.g., non-stimulated conditions) and vehicle controls (e.g., 0.1% DMSO) appropriate for each system. Direct ELISA is used to measure biomarker levels of cell-associated and cell membrane targets. Soluble factors from supernatants are quantified using either HTRF® detection, bead-based multiplex immunoassay or capture ELISA. Overt adverse effects of test agents on cell proliferation and viability (cytotoxicity) are detected by sulforhodamine B (SRB) staining, for adherent cells, and alamarBlue® reduction for cells in suspension. For proliferation assays, individual cell types are cultured at subconfluence and measured at time points optimized for each system (48-hrs: 3 C and CASM3C systems; 72-hrs: BT and HDF3CGF systems; 96-hrs: SAg system). Cytotoxicity for adherent cells is measured by SRB (24-hrs: 3 C, 4H, LPS, SAg, BF4T, BE3C, CASM3C, HDF3CGF, KF3CT, and IMphg systems; 48-hrs: MyoF system), and by alamarBlue staining for cells in suspension (24-hrs: SAg system; 42-hrs: BT system) at the time points indicated.

Results/Deliverables

A Profile plot which is an overlay of the BioMAP signature of four concentrations of a particular test agent. Significant biomarker readouts are annotated, and these key activities are classified and listed into biologically relevant categories. The Profile plot is followed by an overlay of one concentration of the test agent with one concentration of a selected Reference Benchmark. In this comparison, common or differentiating biomarker activities are annotated and listed by system, along with a description of the Reference Benchmark agent. Next, the test agent is mathematically compared against the BioMAP Reference Database to identify the top 3 agents with the most similar overall biomarker signature across the 12 systems. The top match is overlayed against the test agent with annotation of common biomarker activities, description of the similarity search result and the mathematical scores comparing the two profiles. If there are 3 or more test agents, a cluster analysis is performed using pairwise correlation analysis where test agents with similar profiles are graphically linked by lines. Lastly, test agents and consensus profiles for 19 predictive models that are based on profiles from multiple compounds in a known mechanism class are displayed in a Mechanism HeatMAP Analysis.

EMBODIMENTS

1. A method of treating a chronic inflammatory disease or mental health disorder in a subject in need thereof, comprising administering a compound of Formula (I), or a pharmaceutically acceptable salt thereof

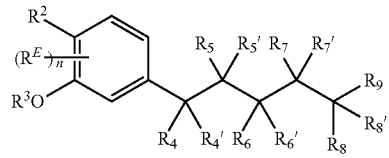

wherein:

$R^1$ and $R^3$ are independently a hydrogen or alkyl; provided that at least one of $R^1$ and $R^3$ is alkyl;

$R^2$ is or

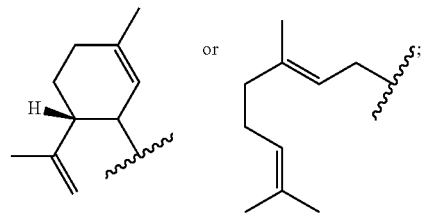 [SMILES: *C1C=C(C)CC[C@H]1C(=C)C ; *C/C=C(\C)CCC=C(C)C]

$R^E$ is hydroxy, halo, —$NR^A R^B$, cyano, nitro, alkyl, -haloalkyl, haloalkoxy and alkoxy;

$R^4$, $R^{4'}$, $R^5$, $R^{5'}$, $R^6$, $R^{6'}$, $R^7$, $R^{7'}$, $R^8$, $R^{8'}$, $R^9$ are each independently selected from the group consisting of hydrogen, —OH, alkyl, alkoxy, —$NR^A R^B$, and halogen;

$R^A$ and $R^B$ are each independently hydrogen or -alkyl; and n is 0, 1, or 2.

2. The method of embodiment 1, wherein $R^1$ is hydrogen and $R^3$ is alkyl.

3. The method of embodiment 2, wherein $R^1$ is hydrogen and $R^3$ is —$C_{1-6}$alkyl.

4. The method of embodiment 3, wherein $R^1$ is hydrogen and $R^3$ is methyl.

5. The method of embodiment 1, wherein $R^1$ and $R^3$ are alkyl.

6. The method of embodiment 5, wherein $R^1$ and $R^3$ are independently —$C_{1-6}$alkyl.

7. The method of embodiment 6, wherein $R^1$ and $R^3$ are methyl.

8. The method of any one of embodiments 1-7, wherein $R^2$ is

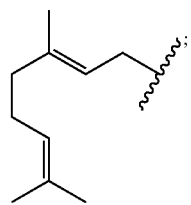 [SMILES: *C/C=C(\C)CCC=C(C)C]

9. The method of any one of embodiments 1-8, $R^4$, $R^{4'}$, $R^5$, $R^{5'}$, $R^6$, $R^{6'}$, $R^7$, $R^{7'}$, R, $R^{8'}$, $R^9$ are each hydrogen.

10. The method of any one of embodiments 1-9, wherein n is 0.

11. The method of any one of embodiments 1-10, wherein the compound is

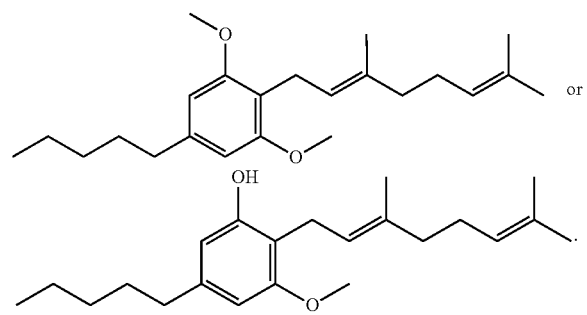

12. The method of embodiment 11, wherein the compound is

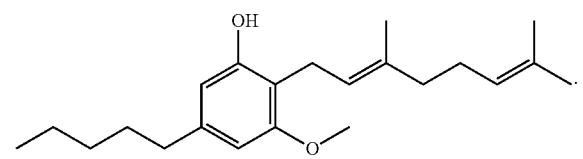 [SMILES: CCCCCc1cc(O)c(C/C=C(\C)CCC=C(C)C)c(OC)c1]

13. The method of embodiment 11, wherein the compound is

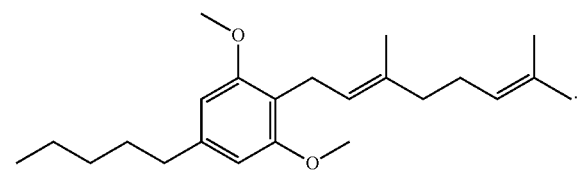 [SMILES: CCCCCc1cc(OC)c(C/C=C(\C)CCC=C(C)C)c(OC)c1]

14. The method of any one of embodiments 1-13, for treating a chronic inflammatory disease.
15. The method of embodiment 14, wherein the chronic inflammatory disease is an inflammatory bowel disease (IBD).
16. The method of embodiment 15, wherein the inflammatory bowel disease is Crohn's disease.
17. The method of embodiment 15, wherein the inflammatory bowel disease is ulcerative colitis.
18. The method of any one of embodiments 1-13, for treating a mental health disorder.
19. The method of embodiment 18, wherein the mental health disorder is anxiety.
20. The method of embodiment 18, wherein the mental health disorder is schizophrenia.
21. The method of any one of embodiments 1-20 wherein the subject is human.
22. A pharmaceutical composition comprising a compound of Formula (I):

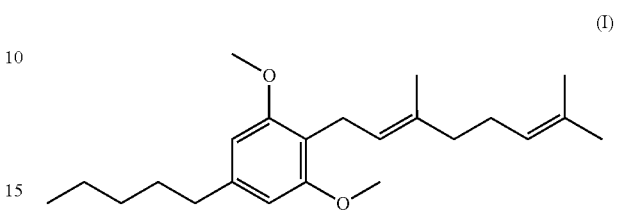

or a pharmaceutically acceptable salt thereof and a pharmaceutically acceptable carrier.

What is claimed:
1. A compound having the structure:

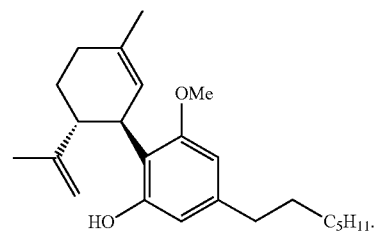

2. A pharmaceutical composition comprising the compound of claim 1, and a pharmaceutically acceptable carrier.
3. A method of treating a chronic inflammatory disease in a subject in need thereof, the method comprising administering to the subject the compound of claim 1, wherein the chronic inflammatory disease is an inflammatory bowel disease.
4. The method of claim 3 wherein the inflammatory disease is Crohn's disease.
5. The method of claim 3, wherein the inflammatory disease is ulcerative colitis.
6. The method of claim 3, wherein the compound is administered orally.
7. A method of treating epilepsy in a subject in need thereof, the method comprising administering to the subject the compound of claim 1.
8. A method of treating seizure in a subject in need thereof, the method comprising administering to the subject the compound of claim 1.

* * * * *